United States Patent
Ahmed et al.

(10) Patent No.: US 11,713,349 B2
(45) Date of Patent: Aug. 1, 2023

(54) EBOLA VIRUS ANTIBODIES AND BINDING AGENTS DERIVED THEREFROM

(71) Applicants: Emory University, Atlanta, GA (US); The Scripps Research Institute, La Jolla, CA (US)

(72) Inventors: Rafi Ahmed, Atlanta, GA (US); Carl Davis, Atlanta, GA (US); Erica Ollmann Saphire, Solana Beach, CA (US)

(73) Assignees: Emory University, Atlanta, GA (US); The Scripps Research Institute, La Jolla, CA (US)

( * ) Notice: Subject to any disclaimer, the term of this patent is extended or adjusted under 35 U.S.C. 154(b) by 200 days.

(21) Appl. No.: 17/196,418

(22) Filed: Mar. 9, 2021

(65) Prior Publication Data

US 2021/0221872 A1 Jul. 22, 2021

Related U.S. Application Data

(63) Continuation of application No. 16/319,775, filed as application No. PCT/US2017/043305 on Jul. 21, 2017, now abandoned.

(60) Provisional application No. 62/364,986, filed on Jul. 21, 2016.

(51) Int. Cl.
- *C07K 16/10* (2006.01)
- *C12Q 1/70* (2006.01)
- *A61P 31/14* (2006.01)

(52) U.S. Cl.
CPC .............. *C07K 16/10* (2013.01); *A61P 31/14* (2018.01); *C12Q 1/701* (2013.01); *C07K 2317/21* (2013.01); *C07K 2317/24* (2013.01); *C07K 2317/524* (2013.01); *C07K 2317/71* (2013.01); *C07K 2317/72* (2013.01); *C07K 2317/76* (2013.01); *C07K 2317/92* (2013.01)

(58) Field of Classification Search
CPC ........................ C07K 16/10; C07K 2317/21; C07K 2317/71; C07K 2317/72; C07K 2317/76; A61K 2039/505
See application file for complete search history.

(56) References Cited

U.S. PATENT DOCUMENTS

| | | |
|---|---|---|
| 2008/0069822 A1 | 3/2008 | Jensen |
| 2015/0125455 A1 | 5/2015 | Green |
| 2015/0344546 A1 | 12/2015 | Jones |
| 2016/0215040 A1 | 7/2016 | Kyratsous |

FOREIGN PATENT DOCUMENTS

| | | |
|---|---|---|
| WO | 2001016183 | 3/2001 |
| WO | 2016075546 | 5/2016 |
| WO | 2021150829 | 7/2021 |

OTHER PUBLICATIONS

Brown et al. Tolerance to Single, but Not Multiple, Amino Acid Replacements in Antibody VH, CDR2, Journal of Immunology, 1996, 156: 3285-3291.
Casset et al. A peptide mimetic of an anti-CD4 monoclonal antibody by rational design, Biochemical and Biophysical Research Communications 307 (2003) 198-205.
Corti et al. Protective monotherapy against lethal Ebola virus infection by a potently neutralizing antibody, Science, 2016, vol. 351 Issue 6279.
Davidson et al. Mechanism of Binding to Ebola Virus Glycoprotein by the ZMapp, ZMAb, and MB-003 Cocktail Antibodies, J Virol, 2015, 89:10982-10992.
Davis et al. Longitudinal Analysis of the Human B Cell Response to Ebola Virus Infection, Cell, 2019, 177 (6):1566-1582.e17.
Flyak et al. Cross-Reactive and Potent Neutralizing Antibody Responses in Human Survivors of Natural Ebolavirus Infection, Cell, 2016, 164(3): 392-405.
Furuyama et al. Discovery of an antibody for pan ebolavirus therapy, Sci Rep. 2016, 6: 20514.
Geisbert et al. Ebola therapy protects severely ill monkeys, Nature. 2014, 514(7520): 41-43.
Geisbert et al. Considerations in the Use of Nonhuman Primate Models of Ebola Virus and Marburg Virus Infection, J Infect Dis, 2015, 212 Suppl 2(Suppl 2):S91-7.
Gregory et al. Structure and function of the complete internal fusion loop from Ebolavirus glycoprotein 2, PNAS, 2011, vol. 108, No. 27, 11211-11216.
Hernandez et al. Development and Characterization of Broadly Cross-reactive Monoclonal Antibodies Against All Known Ebolavirus Species, J Infect Dis, 2015, 212 Suppl 2(Suppl 2):S410-3.
Hoenen et al. Current Ebola vaccines, Expert Opin Biol Ther, 2012, 12(7): 859-872.
Holtsberg et al. Pan-ebolavirus and Pan-filovirus Mouse Monoclonal Antibodies: Protection against Ebola and Sudan Viruses, 2016, J Virol, 90:266-278.
Keck et al., Macaque Monoclonal Antibodies Targeting Novel Conserved Epitopes within Filovirus Glycoprotein, J Virol, 2016, 90:279-291.
Maccallum et al. Antibody-antigen Interactions: Contact Analysis and Binding Site Topography, J. Mol. Biol. (1996) 262, 732-745.
Martinez et al. Impact of Ebola Mucin-Like Domain on Antiglycoprotein Antibody Responses Induced by Ebola Virus-Like Particles, J Infect Dis, 2011, 204 Suppl 3(Suppl 3):S825-32.
Mcelroy et al. Human Ebola virus infection results in substantial immune activation, Proc Natl Acad Sci U S A, 2015, 112(15):4719-24.
Mohan et al. Less is More: Ebola Virus Surface Glycoprotein Expression Levels Regulate Virus Production and Infectivity, J Virol, 2015, 89:1205-1217.
Moller et al. Ebola Virus Entry: A Curious and Complex Series of Events, PLoS Pathog, 2015, 11(4): e1004731.

(Continued)

*Primary Examiner* — Bao Q Li
(74) *Attorney, Agent, or Firm* — Emory Patent Group

(57) ABSTRACT

This disclosure relates to antibodies and antigen binding fragments that specifically bind Ebola virus particles. In certain embodiments, the antibodies and fragments are capable of treating or preventing an Ebola viral infection. In certain embodiments, the antibodies and antigen binding fragments are also contemplated for diagnostic methods and compositions related thereto.

20 Claims, 8 Drawing Sheets

Specification includes a Sequence Listing.

(56) References Cited

OTHER PUBLICATIONS

Murin et al. Structures of protective antibodies reveal sites of vulnerability on Ebola virus, Proc Natl Acad Sci U S A, 2014, 111 48): 17182-17187.

Pascal et al. Development of Clinical-Stage Human Monoclonal Antibodies That Treat Advanced Ebola Virus Disease in Nonhuman Primates, The Journal of Infectious Diseases, 2018;218(S5):S612-26.

Pascalis et al. Grafting of "Abbreviated" Complementarity-Determining Regions Containing Specificity-Determining Residues Essential for Ligand Contact to Engineer a Less Immunogenic Humanized Monoclonal Antibody, Journal of Immunology, 2002, 169: 3076-3084.

Riechmann et al. Reshaping human antibodies for therapy, Nature, 1988, 332(6162):323-7.

Vajdos et al. Comprehensive Functional Maps of the Antigen binding Site of an Anti-ErbB2 Antibody Obtained with Shotgun Scanning Mutagenesis, J. Mol. Biol (2002) 320, 415-428.

Zhang et al. Potent neutralizing monoclonal antibodies against Ebola virus infection, Sci Rep, 2016, 6, 25856.

| Antibody name | cell source | VH nucleotide sequence | VL nucleotide sequence | VH amino acid sequence | VL amino acid sequence | original isotype |
|---|---|---|---|---|---|---|
| 3.1.1083 | bulk GP negative plasmablast | GAGGTGCAGCTGGTGGAGTCTGGGGGAGGCTTGGTACAGCCTGGGGGGTCCCTGAGACTCTCCTGTGCAGCCTCTGGATTCACCTTCAGAAGCTACGACATGCACTGGGTCCGCCAAGCTACAGGAAAAGGTCTGGAGTGGGTCTCAGCTATTGGTACTGCTGGTGACACATACTATCCAGGCTCCGTGAAGGGCCGATTCACCATCTCCAGAGAAAATGCCAAGAACTCCTTGTATCTTCAAATGAACAGCCTGAGAGCCGAGGACACGGCCGTGTATTACTGTGCAAGAGTCCGTTTCGGGGATACAGCCGTTGACTACTGGGGCCAGGGAACCCTGGTCACCGTCTCCTCAGC SEQ ID NO: 52 | GACATCCAGATGACCCAGTCTCCATCCTCCCTGTCTGCATCTGTAGGAGACAGAGTCACCATCACTTGCCGGGCAAGTCAGAGCATTAGCAGCTTTTTAAATTGGCATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAATTTACTACTGTCAACAGAGTTACATTTCCCCATTCACTTTCGGCCCTGGGACCAAAGTGGATATCAAA SEQ ID NO: 51 | EVQLVESGGGLVQPGGSLRLSCAASGFTFRSYDMHWVRQATGKGLESRENAKNSLYLQMNSLRAEDTAVYYCARVRFGDTAVDYWGQGTLVTVSS SEQ ID NO: 2 | DIQMTQSPSSLSASVGDRVTITCRASQSISSFLNWHQQKPGKAPKLLIYAASSLQSGVPSRFSGSGSGTDFTLTISSLQPEDFAIYYCQQSYISPFTFGPGTKVDIK SEQ ID NO: 1 | IgG1, kappa |
| 3.6.1A02 | GP binding B cells | GAGGTGCAGCTGGTGGAGTCAGGAGGAGGCTTGATCCAGCCTGGGGGGTCCCTGAGACTCTCCTGTGCAGCCTCTGGTTTCGCCGTCAGGAGCAACTACTTGAGCTGGGTCCGCCAGGCTCCTGGGAAGGGGCTGGAGTGGGTCTCACTTATTTATAGTGGTGGTCTCACAGCCTACGCAGACTCCGTGGAGGGCCGGTTCACCATCTCCAGAGACAATTCTAAGAACACACTATATCTTCAAATGAACAGCCTGAGAGTCGAGGACACGGCCCTATATTACTGTGCGAGAGTCGCATCATCGGCTGGAACCTTCTACTACGGTATGGACGTCTGGGGCCAAGGGACCACGGTCACCGTCTCCTCAGC SEQ ID NO: 54 | GATATTGTGATGACTCAGTCTCCACGCTCCCTGTCCGTCACCCCTGGAGAGCCGGCCTCCATCTCCTGCAGGTCTAGTCAGAGCCTCCTGCATAGAAATGGATATAACTATTTGGATTGGTATCTGCAGAAGCCAGGGCAGTCTCCACAGCTCCTGATCTATTTGGGTTCTAATCGGGCCTCCGGGGTCCCTGACAGGTTCAGTGGCAGTGGATCAGGCACAGATTTTACACTGAAAATCAGCAGAGTGGAGGCTGAAGATGTTGGGGTTTATTACTGCATGCAAGCTCTACAAACTCCCTCGTGGACGTTCGGCCAAGGGACCAAGGTGGAAATCAAA SEQ ID NO: 53 | EVQLVESGGGLIQPGGSLRLSCAASGFAVRSNYLSWVRQAPGKGLEWVSLIYSGGLTAYADSVEGRFTISRDNSKNTLYLQMNSLRVEDTALYYCARVASSAGTFYYGMDVWGQGTTVTVSS SEQ ID NO: 4 | DIVMTQSPRSLSVTPGEPASISCRSSQSLLHRNGYNYLDWYLQKPGQSPQLLIYLGSNRASGVPDRFSGSGSGTDFTLKISRVEAEDVGVYYCMQALQTPSWTFGQGTKVEIK SEQ ID NO: 3 | IgG1, kappa |

FIG. 2

| | | | | | | |
|---|---|---|---|---|---|---|
| 2.1.1D05 | GP binding B cells | GAGGTGCAGCTGGTGGAG TCTGGGGGAGGCTTGGTA AAACCTGGGGGGTCCCTTA GACTCTCCTGTGCAGCCTC TGGATTCACTTTCAGTAAC GCCTGGATGAACTGGGTCC GCCAGGCTCCAGGGAAGG GCTGGAGTGGGTTGGCC GTATTAAGAGCAAAACTG ATGGTGGGGCTGCAGACT ACGCTGCACCCGTGAAGG GCAGATTCACCATCTCAAG AGATGATTCAAAAAACAC GCTGTATCTGCAAATGAAC AGCCTGAAAACCGAGGAC ACAGCCGTGTATTTCTGTA CCACAGTCTACAGATACAA CTATGATTCCGTCTGGGGC CAGGGAACCCTGGTCACCG TCTCCTCAGC SEQ ID NO: 56 | CAGTCTGTGCTGACGCAGC CGCCCTCAGTGTCTGGGGC CCCAGGGCAGAGGGTCAC CATCTCCTGCACTGGGAGC AGTTCCAACATCGGGGCA GGTTATGATGTATACTGGT ACCAGCAGCTTCCAGGAAC AGCCCCCAAACTCCTCATC TATGGTAACAGCAATCGG CCCTCAGGGGTCCCTGACC GATTCTCTGGCTCCAAGTC TGGCACCTCAGCCTCCCTG GCCATCACTGGGCTCCAGG CTGAGGATGAGGCTGATT ACTACTGCCAGTCCTTTGA CAGCAGCCTGAGAGATTCT TGGGTGTTCGGCGGAGGG ACCAAGCTGACCGTCCTA SEQ ID NO: 55 | EVQLVESGGGL VKPGGSLRLSCA ASGFTFSNAWM NWVRQAPGKG LEWVGRIKSKT DGGAADYAAP VKGRFTISRDDS KNTLYLQMNSL KTEDTAVYFCTT VYRYNYDSVW GQGTLVTVSS SEQ ID NO: 6 | QSVLTQPPSVSG APGQRVTISCTGS SSNIGAGYDVY WYQQLPGTAPK LLIYGNSNRPSG VPDRFSGSKSGTS ASLAITGLQAED EADYYCQSFDSS LRDSWVFGGGT KLTVL SEQ ID NO: 5 | IgG1, lambda |
| 2.1.1D07 | GP binding B cells | GAGGTGCAGCTGTTGGAG TCTGGGGGAGGCTTGGTA CAGCCTGGGGGGTCCCTGA GACTCTCCTGTGCAGCCTC TGGATTCACCTTTAGCACC TATGGCATGAGCTGGGTCC GCCAGGCTCCAGGGAAGG GCTGGAGTGGGTCTCAG GTATTAGTGGTAGTGGTG GTATCACATACTACGCAGA CTCCGTGAGGGGCCGGTTC ACCATCTCCAGAGACAATT CCAAGAACACGCTGTATCT GCAATGAACAGCCTGAG AGCCGAGGACACGGCCGT ATATTACTGTGCGAAAGT GGGGGAGTATTACGATTT TTGGAGTGGTTATCCCCC TTTGAATACTGGGGCCAG GGAACCCTGGTCACCGTCT CCTCAGC SEQ ID NO: 58 | GAAATTGTGTTGACGCAG TCTCCAGGCACCCTGTCTTT GTCTCCAGGGGAAAGAGC CACCCTCTCCTGCAGGGCC AGTCAGAGTGTTAGCAGC AGCTACTTAGCCTGGTACC AGCAGAAACCTGGCCAGG CTCCCAGGCTCCTCATCTA TGGTGCATTTAACAGGGCC ACTGGCATCCCAGACAGGT TCAGTGGCAGTGGGTCTG GGACAGACTTCACTCTCAC CATCAGCAGACTGGAGCCT GAAGATTTTGCAGTGTATT ACTGTCAGCTGTATGGTAG CTCACCGTGGACGTTCGGC CAAGGGACCAAGGTGGAA ATCAAA SEQ ID NO: 57 | EVQLLESGGGL VQPGGSLRLSCA ASGFTFSTYGMS WVRQAPGKGLE WVSGISGSGGIT YYADSVRGRFTI SRDNSKNTLYLR MNSLRAEDTAV YYCAKVGEYYD FWSGYSPFEYW GQGTL SEQ ID NO: 8 | EIVLTQSPGTLSL SPGERATLSCRAS QSVSSSYLAWYQ QKPGQAPRLLIY GAFNRATGIPDR FSGSGSGTDFTLT ISRLEPEDFAVYY CQLYGSSPWTFG QGTKVEIK SEQ ID NO: 7 | IgG1, kappa |

FIG. 3

| mAb name | Heavy chain nucleotide sequence | Light chain nucleotide sequence |
|---|---|---|
| 2.1.1B02 | GAGGTGCAGCTGGTGCAGTCTGGGGCTGAGGTGAAGAAG CCTGGGGCCTCAGTGAAGGTTTCCTGCAAGGCATCTGGAT ACACCTTCACCAGCTACTATATGCACTGGGTGCGACAGGC CCCTGGACAAGGGCTTGAGTGGATGGGAATAATCAACCCT AGTGGTGGTAGCACAAGCTACGCACAGAAGTTCCAGGGC AGAGTCACCATGACCAGGGACACGTCCACGAGCACAGTCT ACATGGAGCTGAGCAGCCTGAGATCTGAGGACACGGCCG TGTATTACTGTGCTAGGCATGATAGTAGTGGTTATGATGCT TTTGATATCTGGGGCCAAGGGACAATGGTCACCGTCTCTTC A SEQ ID NO: 197 | TCCTATGAGCTGACACAGCCACCCTCGGTGTCAGTGTCCC CAGGACAGACGGCCAGGATCACCTGCTCTGGAGATGCA TTGCCAAAGCAATATGCTTATTGGTACCAGCAGAAGCCA GGCCAGGCCCCTGTGCCGGTGATATATAAAGACAGTGA GAGGCCCTCAGGGATCCCTGAGCGATTCTCTGGCTCCAG CTCAGGGACAACAGTCACGTTGACCATCAGTGGAGTCCA GGCAGAAGACGAGGCTGACTATTACTGTCAATCATCAGA CAGCAGTGGTACTTATGTGGTATTCGGCGGAGGGACCAA GCTGACCGTCCTA SEQ ID NO: 198 |
| 5.24.1C11 | CAGGTGCAACTGGTGCAGTCAGGGGCTGAGGTGAAGAAG CCTGGGGCCTCAGTGAAGGTTTCCTGCAGGACATCTGGAT ACACATTCTCCAGCTACAATATACATTGGGTGCGACAGGC CCCTGGACAAGGTCTTGAGTGGATGGGAGTTATTAATCCTT ATGGCCGTAGTACCACACTTTACGCACGGAGGTTCCGGGA CAGAGTCACCATGACCAGGGACACGTCCACGAGCACAGTT TACATGGAACTGAGCAGCCTGAGATCCGAGGACACGGCC GTATACTTCTGTGGAAGGCTTTACAGTGGTGCACCCTATGG TTTGGACGTCTGGGGCCAAGGGAGCACGGTCACCGTCTCT TCA SEQ ID NO: 199 | GATATTGTGATGACTCAGTCTCCACTCTCCCTGCCCGTCA CCCCTGGAGAGCCGGCCTCCATCTCCTGCAGGTCTAGTC AGAGCCTCCTGCATAGTAATGGATACAACTATGTGGATT GGTACCTGCAGAAGCCAGGGCAGTCTCCACAGCTCCTGA TCTATTTGGGTTCTAGTCGGGCCTCCGGGGTCCCTGACAG GTTCAGTGGCAGTGGATCAGGCACAGATTTTACACTGAA AATCAGCAGAGTGGAGACTGAGGATGTTGGCATTTATTA CTGCATGCAAGGTCTACAAACTCCCCTCACTTTCGGCGG AGGGACCAAGGTGGAGATCAAA SEQ ID NO: 200 |
| 9.20.1C03 | CAGGTGCAGCTGGTGCAGTCTGGGGCTGAAGTGAAGAAG CCTGGGTCCTCGGTGAAGGTCGCCTGCAAGGTTTCTGGAG GCACCTTCAGCAGCTATACTATTAGTTGGGTGCGACAGGC CCCTGGACAAGGGCTTGAGTGGATGGGAGGGATCATCCCT TCCTTTGGTGTGGGACACTACTCACAGAAGTTCCGGGACA GAGTCACGCTAACCGCGGACAAATCCACGACCACAGCCTT CTTGGAACTGAGCAGCGTGAGATCTGAAGACACGGCCCTA TATTACTGTGCGATACTGGGGACTTTTAACTGGAAGTCCGG GGGCAACTACTTCGGCCCCTGGGGCCAGGGGACCCTGGTC ACCGTCTCTTCA SEQ ID NO: 201 | GACATCGTGCTGACCCAGTCTCCAGACTCCCTGGCTGCGT CTCTGGGCGAGAGGGCCACCATCAGCTGCAAGTCCAGCC ACAGTGTTTTATACAGCTCCAACAATAAGGACTTCTTTGC CTGGTACCAGCAGAAACCAGGACAGCCTCCCAAACTGCT CATTTCCTGGGCATCTACCCGGGAATCCGGGGTCCCTGTC CGATTCAATGGCGGCGGGTCTGGGACACATTTCACTCTC ACCATCAGCAGCCTGCAGGCTGAAGATGTGGCAGTTTAC TACTGTCAGCAATATTTTAGTTCTCCGATCACCTTCGGCC AAGGGACACGACTGGAGATTAAA SEQ ID NO: 202 |

FIG. 8

| mAb name | Heavy chain nucleotide sequence | Light chain nucleotide sequence |
|---|---|---|
| 5.24.1 B03 | CAGGTGCAGCTGCAGGAGTCGGGCCCAGGACTGGTGAAGCCTTCGGAGAGCCTGTCCCTCACATGCACTATCTCTGGCGGCTCCATAAGGGACTATTACTGGAGCTGGATTCGGCAGGCCCCAGGGAAGGGACTGGAGTGGATCGGATATAAGTATCACGCTGCGCGCGGCAACTCCAATCCCTCCCTCGAGAGTCGAGTCACCATGTCCATCGACACGTCCAGGAGCGAGTTCTCCCTGAGGCTGACTTCTGTGACCGCTGCGGACACGGCCGTCTATTATTGTGCGAGAGTTCAATACGGTCCTGGGGGCGGTTACTATTCGGGGAACTGGTTGGACCTCTGGGGCCAGGGAACCCTGGTCACCGTCTCTTCA SEQ ID NO: 203 | GAAATTGTGTTGACACAGTCTCCAAACACCCTGTCTTTGTCTCCAGGGGAAAGAGCCACCCTCTCCTGCAGGGCCAGTCAGAGTCTTCGTACCAACCAGTTAGCCTGGTACCAGCAAAAACCTGGCCAGGCTCCCAGGCTCCTCATCCATACATCCACCAGGGCCACTGGCATCCCAGACAGGTTCAGTGGCAGTGGGTCTGGGACAGACTTCACTCTCACCATCAGCGGACTGGAGGCTGAAGACTTTGCAGTGTATTACTGTCAGGCGTCTGATACCTCATCGCTCACTTTCGGCGGAGGGACCAAGTTAGAGATCAGA SEQ ID NO: 204 |
| 9.20.1 D09 | CAGCTGCAGCTGCAGGAGTCGGGCCCAGGACTGGTGAAGCCTTCGGAGACCCTGTCCCTCACCTGCACTGTCTCTGGTGGCTCCGTCGCCAGTAGTAATGACTACTGGGGCTGGATCCGCCAGCCCCAGGGAAGGGGCCGGAGTGGATTGGGACTATCTTTTATAGAGGGACCACCGACTACAACCCGTCCCTCAAGAGTCGACTCACTATGTCCGTGGACACGTCCAGGAACCAGTTCTCCCTGAAGCTGAGCTCTGTGACCGCCGCAGACACGGCTGTCTATTACTGTGCGAGACTGCCCCTATGGTTCAGTGAGTTAGGTCATGACTACTGGGGCCAGGGAACCCTGGTCACCGTCTCCTCA SEQ ID NO: 205 | GAAATAGTGATGACGCAGTCTCCAGCCACCCTGTCTCTGTCTCCAGGAGAAAGAGCCTCCCTGTCCTGCAGGGCCAGTCAGAGTATTGCCACCAACTTAGCCTGGTACCAGCAAAAACCTGGCCAGCCTCCCAGGGTCCTCATCTATGGTGCATCCACAAGGGCAACTGGTATCCCAACCAGGTTCAGTGGCAGTGGATCTGGGACAGAGTTCACTCTCACCATCAGCAGCCTGCAGTCTGAAGATTTTGCAATTTATTACTGTCACCAGTATCATAGCTGGCGGACGTTCGGCCAAGGGACCAAGGTAGAAATGAAA SEQ ID NO: 206 |
| 5.24.2 A03 | CAGGTGCAGCTGCATGAGTCGGGCCCAGGGCTGGTGCAGCCTTCGGAGACCCTGTCCCTCACCTGCACTGTCTCTGGTGACTCCATCACTAATTACTACTGGAGCTGGATCCGGCAGCCCCCAGGGAAGGGACTGGAGTGGATTGGATATATGTATTACAGTGCGAGCGCCCACTACAATCCCTCCCTCCAGAGTCgAGTCACCATTTCAGTGGACACGTCCAAGAACCAGTTCTCCCTGAAACTGAGCTCTGTGACCGCTGCGGACACGGCCGTGTATTTCTGTGCGAGAGTGGACTACAGTTCGAGTAGTTATTATTCGGGAAACTGGTTCGACCCCTGGGGCCAGGGAACCCTTGTCACCGTCTCCTCA SEQ ID NO: 207 | CAGTCTGCCCTGACTCAGCCTCCCTCCGCGTCCGGGTCTCTGGACAGTCAGTCACCATCTCCTGCACTGGAACCAGCAGTGACGTTGGTGTTTATAATTCTGTCTCCTGGTACCGACAGCACCCAGGCAAAGTCCCCAAACTCATGATTTATGAGGTCAGTAAGCGGCCCTCAGGGGTCCCTGATCGCTTCTCTGGCTCCAAGTCCGGCAACACGGCCTCCCTGACCGTCTCTGGGCTCCAGGCTGACGATGAGGGTGATTATTACTGCTGCTCATGTTCAGGCACCAACAGCCTCTGTGTCTTCGGAACTGGGACCAAGGTCACCGTCCTG SEQ ID NO: 208 |

FIG. 9

| mAb name | Heavy chain nucleotide sequence | Light chain nucleotide sequence |
|---|---|---|
| 9.20.1 A02 | GAGGTGCAGCTGGTGGAGTCTGGGGGAGACTTAGTACAG CCTGGGGGGTCCCTCAGACTCTCCTGTGCAGCCTCTGGAAT CACCTTGAGTGGAGTTTGGATGAACTGGGTCCGCCAGGCT CCAGGGAAGGGGCTGGAGTGGATTGGCCGTATTAAAAGC ACAAGTGACGGTGGGAGAGCAGACTTCGCCGCACCCGCG AGAGGCAGATTCACCATGTCAAGAGATGAGTCAAAGAAT AAGCTGTTTCTGCAAATGAACAACCTGGGAATCGAAGACA CAGGCATGTATTATTGTTTCACGAGAGTCCAAAGAGACGG AACTAAAGATGACTTCTGGGGCCGGGGAACCCTGGTCACC GTCTCTTCA SEQ ID NO: 209 | CAGTCTGTGCTGACGCAGCCGCCCTCAGTGTCTGGGGCC CCAGGGCAGACGGTCACCATCTCCTGCACTGGGAGCTAC TCCAACATCGGGGCAGGTTATGATGTACAGTGGTACCAG CACCTTCCTGGAACAGCCCCCAAACTCCTCATTTATGATA ATGTCCATCGGCCCTCAGGGGTCCCTGACCGATTCTCTGG CTCCAAGTCTGGCACCTCAGCCTCCCTGGCCATCACTGGG CTCCAGACTGAAGATGAGGCTGATTATTATTGCCAGTCCT ATGACAGCAGACTGAGGGATCAATGGGTGTTCGGCGGA GGGACCAAGCTGACCGTCCTA SEQ ID NO: 210 |
| 5.24.2 C05 | CAGGAGCAGCTGCAAGAGTCGGGCCCAGGACTGGTGAAG CCTTCGGGGACCCTGTCCCTCACCTGCACTGTCTCCGGCGT CTCCGTCAGTGGGAGTTACTTCTGGAATTGGGTCCGCCAGC CCCCAGGGAAGGGACTGGAGTGGCTTGGATTTATTCATAG CACTGGGAGCACCAACACCAACCCCTCCCTCAAGAGTCGA GTCACCATTTCAGTAGACACGTCCAAGAACCAGTTCTCCCT GAGGCTGACTTCTGTGAGCGCTGCGGACACGGCCGTTTATT ACTGTGCGAGAGCCGCTTGGTTAGTAGGGGGGAGTACTA CAACTACGGTATGGACCTTTGGGGCCAAGGGACCACGGTT ACCGTCTCCTCA SEQ ID NO: 211 | CAGTCTGCCCTGACTCAGCCCGCCTCCGTTTCTGGGTCTC CTGGACAGTCGATCACCCTCTCCTGCACTGTAGGCGGTA ATAAGTTTGTCTCTTGGTATCAACAACACCCAGGCAAAG CCCCCAAACTCATTATTTCTGATTTCACTGATCGGCCCTC AGGGGTCTCTAGTCGCTTCTCTGGCTCCAAGTCTGGCAAC ACGGCCTCCCTGACCATCTCTGGGCTCCAGCCTGACGAC GAGGCTACTTATTTCTGCAGTTCTTACGCAAGCACCAGCA CTTCTCTTTGGGTCTTCGGCGGGGGGACCAAGCTGACCGT CCTA SEQ ID NO: 212 |
| 5.24.2 B07 | CAGGTGCAGCTGGTGGAATCTGGGGGAGGCGTGGTCCAG CCTGGGAGGTCCCTGAGACTCTCCTGTGTAGCGTCTGGATT CACCTTCAGTAGTTATGGCATGCACTGGGTCCGCCAGGCTC CAGGCAAGGGGCTGGAGTGGGTGGCATTTATATGGTATGA TGGAACTATTCAATACTATGGAGACTCCGTGAAGGGCCGA TTCATCATCTCCAGAGACAATTCCAGGAATACGCTGTATCT ACAAATGAACAGCCTGAGAGCCGAGGACACGGCTGTGTA TTACTGTGCGAGCACTCTTTACCGAAACGGTGACTACGGGT CAGGGTCCCGGACCCCGGACGACTACTGGGGCCAGGGAA CCCTGGTCACCGTCTCTTCA SEQ ID NO: 213 | GGCATCCAGTTGACCCAGTCTCCATCCTTCCTGTCTGCAT CTGTAGGAGACAGAGTCACCATCACTTGCCGGGCCAGTC AGGGCATTTACACTTATTTAGCCTGGTATCAGCAAAAAC CAGGGAAAGCCCCTAAGCTCCTGGTCTATGTTGCATCCA CTTTGCAAAGTGGGGTCCCATCAAGGTTCAGCGGCAGTG GATCTGGGACAGAATTCACTCTCACAATCAGCAGCCTGC AGCCTGAAGATTTTGCAACTTATTACTGTCAACAGCTTAA TAGTTACCCTCTCACTTTTGGCCAGGGGACCAAGCTGGA GATCAAA SEQ ID NO: 214 |

FIG. 10

EBOLA VIRUS ANTIBODIES AND BINDING AGENTS DERIVED THEREFROM

CROSS-REFERENCE TO RELATED APPLICATIONS

This application is a continuation of U.S. application Ser. No. 16/319,775 filed Jan. 22, 2019, which is the National Stage of International Application No. PCT/US2017/043305 filed Jul. 21, 2017, which claims the benefit of U.S. Provisional Application No. 62/364,986 filed Jul. 21, 2016. The entirety of each of these applications is hereby incorporated by reference for all purposes.

STATEMENT REGARDING FEDERALLY SPONSORED RESEARCH OR DEVELOPMENT

This invention was made with government support under W3194Q-14-1-0010 awarded by DARPA and AI109762 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 16008USCON_ST25.txt. The text file is 103 KB, was created on Mar. 8, 2021, and is being submitted electronically via EFS-Web.

BACKGROUND

Ebolaviruses are in the family Filoviridae that cause severe fevers that typically leads to fatalities in humans. Thus, there is a need to identify improved therapeutic methods for treating or preventing Ebola virus infections.

ZMapp is a combination of monoclonal antibodies in testing for the treatment for Ebola virus disease. Qiu et al., Nature, 2014, 514 (7520): 47-53. See also WO2001/016183.

Martinez et al. report an Ebola mucin-like domain effect antiglycoprotein antibody responses induced by Ebola virus-like particles. J Infect Dis. 2011, 204 Suppl 3:S825-32.

Murin et al. report structures of protective antibodies reveal sites of vulnerability on Ebola virus. Proc Natl Acad Sci USA. 2014, 111(48):17182-7.

Flyak et al. report cross-reactive and potent neutralizing antibody responses in human survivors of natural ebolavirus infection. Cell. 2016, 164(3):392-405

Furuyama et al. report an antibody for pan-Ebolavirus therapy. Sci Rep. 2016, 6:20514.

References cited herein are not an admission of prior art.

SUMMARY

This disclosure relates to antibodies and antigen binding fragments that specifically bind Ebola virus particles. In certain embodiments, the antibodies and fragments are capable of treating or preventing an Ebola viral infection. In certain embodiments, the antibodies and antigen binding fragments are also contemplated for diagnostic methods and compositions related thereto. In certain embodiments, the antibodies are non-naturally occurring chimeric antibodies.

In certain embodiments, this disclosure relates to antibodies or antigen binding fragments comprising six complementarity determining regions (CDRs) or consensus sequences thereof, wherein the CDRs comprise the three light chain CDRs derived from an antibody selected from 5.1.10B3, 5.6.1A02, 2.1.1D05, 2.1.1D07, 9.6.3D06, 2.1.7G07, 9.6.3A06, 5.1.13G03, 5.6.c2618, 2.10.1E06, 9.6.1A09, 5.1.7D03 and wherein the CDRs comprise the three heavy chain CDRs derived from an antibody selected from 5.1.10B3, 5.6.1A02, 2.1.1D05, 2.1.1D07, 9.6.3D06, 2.1.7G07, 9.6.3A06, 5.1.13G03, 5.6.c2618, 2.10.1E06, 9.6.1A09, 5.1.7D03, and wherein the antibody or antigen binding fragment thereof specifically or immunospecifically binds to an epitope expressed in an Ebola virus particle.

In certain embodiments, the CDRs comprise
the three light chain CDRs of antibody 5.1.10B3 within

```
                                      SEQ ID NO: 1
DIQMTQSPSSLSASVGDRVTITCRASQSISSFLNWHQQKPGKAPKLLIYA

ASSLQSGVPSRFSGSGSGTDFTLTISSLQPEDFAIYYCQQSYISPFTFGP

GTKVDIK;

CDR 1
                                     (SEQ ID NO: 11)
RASQSISSFLN;

CDR2
                                     (SEQ ID NO: 12)
AASSLQS;
and

CDR3
                                     (SEQ ID NO: 13)
QQSYISPFT;
``` and
the three heavy chain CDRs of antibody 5.1.10B3 within

```
                                      SEQ ID NO: 2
EVQLVESGGGLVQPGGSLRLSCAASGFTFRSYDMHWVRQATGKGLEWVSA

IGTAGDTYYPGSVKGRFTISRENAKNSLYLQMNSLRAEDTAVYYCARVRF

GDTAVDYWGQGTLVTVSS;

CDR 1
                                     (SEQ ID NO: 14)
FTFRSYDMH;

CDR 2
                                     (SEQ ID NO: 15)
IGTAGDTYYP;
and

CDR 3
                                     (SEQ ID NO: 16)
VRFGDTAVDY.
```

In certain embodiments, the CDRs comprise
the three light chain CDRs of antibody 5.6.1A02 within

```
                                      SEQ ID NO: 3
DIVMTQSPRSLSVTPGEPASISCRSSQSLLHRNGYNYLDWYLQKPGQSPQ

LLIYLGSNRASGVPDRFSGSGSGTDFTLKISRVEAEDVGVYYCMQALQTP

SWTFGQGTKVEIK;

CDR 1
                                     (SEQ ID NO: 17)
RSSQSLLHRNGYNYLD;
```

CDR 2
(SEQ ID NO: 18)
LGSNRAS;
and

CDR 3
(SEQ ID NO: 19)
MQALQTPSWT;
and the three heavy chain CDRs of antibody 5.6.1A02 within SEQ ID NO: 4
EVQLVESGGGLIQPGGSLRLSCAASGFAVRSNYLSWVRQAPGKGLEWVSL
IYSGGLTAYADSVEGRFTISRDNSKNTLYLQMNSLRVEDTALYYCARVAS
SAGTFYYGMDVWGQGTTVTVSS;

CDR 1
(SEQ ID NO: 20)
FAVRSNYLS;

CDR 2
(SEQ ID NO: 21)
LIYSGGLTAYADSVEG;
and

CDR 3
(SEQ ID NO: 22)
VASSAGTFYYGMDV.

In certain embodiments, the CDRs comprise the three light chain CDRs of antibody 2.1.1D05 within SEQ ID NO: 5
QSVLTQPPSVSGAPGQRVTISCTGSSSNIGAGYDVYWYQQLPGTAPKLLI
YGNSNRPSGVPDRFSGSKSGTSASLAITGLQAEDEADYYCQSFDSSLRDS
WVFGGGTKLTVL;

CDR 1
(SEQ ID NO: 23)
TGSSSNIGAGYDVY;

CDR 2
(SEQ ID NO: 24)
GNSNRPS;
and

CDR 3
(SEQ ID NO: 25)
QSFDSSLRDSWV,
and the three heavy chain CDRs of antibody 2.1.1D05 within SEQ ID NO: 6
EVQLVESGGGLVKPGGSLRLSCAASGFTFSNAWMNWVRQAPGKGLEWVGR
IKSKTDGGAADYAAPVKGRFTISRDDSKNTLYLQMNSLKTEDTAVYFCTT
VYRYNYDSVWGQGTLVTVSS;

CDR 1
(SEQ ID NO: 26)
FTFSNAWMN;

CDR 2
(SEQ ID NO: 27)
RIKSKTDGGAADYAAPVKG;
and

CDR 3
(SEQ ID NO: 28)
VYRYNYDSV.

In certain embodiments, the CDRs comprise the three light chain CDRs of antibody 2.1.1D07 within SEQ ID NO: 7
EIVLTQSPGTLSLSPGERATLSCRASQSVSSSYLAWYQQKPGQAPRLLIY
GAFNRATGIPDRFSGSGSGTDFTLTISRLEPEDFAVYYCQLYGSSPWTFG
QGTKVEIK;

CDR 1
(SEQ ID NO: 29)
RASQSVSSSYLA;

CDR 2
(SEQ ID NO: 30)
GAFNRAT;
and

CDR 3
(SEQ ID NO: 31)
QLYGSSPWT,
and the three heavy chain CDRs of antibody 2.1.1D07 within SEQ ID NO: 8
EVQLLESGGGLVQPGGSLRLSCAASGFTFSTYGMSWVRQAPGKGLEWVSG
ISGSGGITYYADSVRGRFTISRDNSKNTLYLRMNSLRAEDTAVYYCAKVG
EYYDFWSGYSPFEYWGQGTL;

CDR 1
(SEQ ID NO: 32)
FTFSTYGMS;

CDR 2
(SEQ ID NO: 33)
GISGSGGITYYADSVRG;
and

CDR 3
(SEQ ID NO: 34)
VGEYYDFWSGYSPFEY.

In certain embodiments, the CDRs comprise the three light chain CDRs of antibody 9.6.3D06 within SEQ ID NO: 9
DIQMTQSPSTLSASVGDRVTITCRASQRINNLVAWYQQKPGKAPKVMIYD
ASSLKSGVPSRFSGSGSGTEFTLTISSLQPDDFATYFCQQYDTDSGWTFG
QGTKVEIK;

CDR 1
(SEQ ID NO: 35)
RASQRINNLVA;

CDR 2
(SEQ ID NO: 36)
DASSLKS;

CDR 3
(SEQ ID NO: 37)
QQYDTDSGWT,
and the three heavy chain CDRs of antibody 9.6.3D06 within SEQ ID NO: 10
EVQLLESGGGLVQPGGSLRLSCAASGFTFSKYAMIWVRQAPGKGLQWVAG INKSGGRTYYADSVRGRFTISRDNSKNTLYLQMKSLRADDTAMYYCAKEG SPLSDVLLVAAPFGWFDPWGQGTLVTVSS;

CDR 1
(SEQ ID NO: 38)
FTFSKYAMI;

CDR 2
(SEQ ID NO: 39)
GINKSGGRTYYADSVRG;
and

CDR 3
(SEQ ID NO: 40)
EGSPLSDVLLVAAPFGWFDP.

In certain embodiments, the CDRs comprise the three light chain CDRs of antibody 2.1.7G07 within SEQ ID NO: 69
EIVLTQSPGTLSLSPGERATLSCRASQSVSSSYLAWYQQKPGQAPRLLIY GAFNRATGIPDRFSGSGSGTDFTLTISRLEPEDFAVYYCQQYGRSPFTFG PGTKVDIK;

CDR 1
(SEQ ID NO: 70)
QSVSSSY;

CDR2
(SEQ ID NO: 71)
GAFNRAT;
and

CDR3
(SEQ ID NO: 72)
QQYGRSPFT;
and
the three heavy chain CDRs of antibody 2.1.7G07 within SEQ ID NO: 73
EVQLVESGGGLVQPGGSLRLSCAASGFAFSTYAMSWVRQAPGKGLEWVSA ITGSGYSTYYADSVKGRFTISGDNSKNTLYLQMNSLRAEDTALYYCAKVG EYYDFWSGYSPFDSWGQGTLVTVSS;

CDR 1
(SEQ ID NO: 74)
GFAFSTYA;

CDR 2
(SEQ ID NO: 75)
ITGSGYST;
and

CDR 3
(SEQ ID NO: 76)
AKVGEYYDFWSGYSPFDS.

In certain embodiments, the CDRs comprise the three light chain CDRs of antibody 9.6.3A06 within SEQ ID NO: 77
DIVMTQTPLSSAVTLGQPASISCRSSQRLVHSDGNTYLSWLHQRPGQPPR LLIYKVSLRFSGVPDRFSGSGAGTDFTLKISRVEAEDVGIYYCMQATQFP LTFGGGTKVEIK;

CDR 1
(SEQ ID NO: 78)
QRLVHSDGNTY;

CDR 2
(SEQ ID NO: 79)
KVSLRFS;
and

CDR 3
(SEQ ID NO 80)
MQATQFPLT;
and the three heavy chain CDRs of antibody 9.6.3A06 within SEQ ID NO: 81
EVQLLESGGGLVKPGGSLRLSCAASGFTFNEYMMNWVRQPPGKGLEWVSS ISGTSTYINYADSVKGRFTISRDNAKNSLYLQMNSLRSDDTAMYYCARGS TGGYWGQGTLITVSS;

CDR 1
(SEQ ID NO: 82)
GFTFNEYM;

CDR 2
(SEQ ID NO: 83)
ISGTSTYI;
and

CDR 3
(SEQ ID NO: 84)
GSTGGY.

In certain embodiments, the CDRs comprise the three light chain CDRs of antibody 5.1.13G03 within SEQ ID NO: 85
DIQMTQSPSSLSASVGDRVTITCRASQSISSYLNWYQQKPGKAPKVLIYS AFSLQNGVPSRFSGSGSGTDFTLTISSLQPEDFATYYC QQSYSTPRT F GQGTKVEIK;

CDR 1
(SEQ ID NO: 86)
QSISSYLN;

CDR 2
(SEQ ID NO: 87)
SAFSLQN;
and

CDR 3
(SEQ ID NO: 88)
QQSYSTPRT;
and the three heavy chain CDRs of antibody 5.1.13G03 within SEQ ID NO: 89
QVQLQESGPGLVKPSGTLSLTCAVSGGSISSTNWWSWVRQPPGKGLEWIG
EIYHSGSTNYNPSLKSRVTISLDKSKDQFSLKLSSVTAADTAVYYCAYSN
TWTGGWGQGTLVTVSS;

CDR 1
(SEQ ID NO: 90)
GSISSTNWWS;

CDR 2
(SEQ ID NO: 91)
HSGSTN;
and

CDR 3
(SEQ ID NO: 92)
SNTWTGG.

In certain embodiments, the CDRs comprise the three light chain CDRs of antibody 5.6.c2618 within SEQ ID NO: 93
EVVLTQSPVTLSLSPGERATLSCRASQSVSGYLAWYQQKPGQVPRLLIYD
TSNRATGIPARFSGSGSGTDFTLTISTIEPEDFAVYYCQQRSKWGVTFGG
GTKVDIK;

CDR 1
(SEQ ID NO: 94)
QSVSGYLA;

CDR 2
(SEQ ID NO: 95)
DTSNRAT;
and

CDR 3
(SEQ ID NO: 96)
QQRSKWGVT;
and the three heavy chain CDRs of antibody 5.6.c2618 within SEQ ID NO: 97
QVQLVQSGAEVKKPGASVNLSCKGSGYSFRTYYIHWVRQAPGQGLEWMGI
INSSGGGTTYAQKFQGRVTMTRDTSTSTVYMELRSLKYEDTAMYYCARDR
FPTVSGEPFAMDVWGQGTTVTVSS;

CDR 1
(SEQ ID NO: 98)
GYSFRTYYIH;

CDR 2
(SEQ ID NO: 99)
INSSGGGTTY;
and

CDR 3
(SEQ ID NO: 100)
DRFPTVSGEPFAMDV.

In certain embodiments, the CDRs comprise the three light chain CDRs of antibody 2.10.1E06 within SEQ ID NO: 101
EIVLTQSPGTLSLSPGERATLSCRASQSVTSNYLAWYQQKPGQAPRVLIY
GASSRATGIPDRFSGSGSGTDFTLTISRLEPEDFAVYYCQQFGASPPYSF
GQGTKVEIK;

CDR 1
(SEQ ID NO: 102)
QSVTSNYLA;

CDR 2
(SEQ ID NO: 103)
GASSRAT;
and

CDR 3
(SEQ ID NO: 104)
QQFGASPPYS;
and the three heavy chain CDRs of antibody 2.10.1E06 within SEQ ID NO: 105
EVQLVESGGGLIQPGGSLRLSCTASGFTFSKFAMSWVRQAPGRGLEWISY
ISGGSKTKYYADSVRGRFTISRDNAKGSLFLQMNSLRAEDTAIYFCAKKG
WQSTFLGMDYFYGMDVWGKGTTVTVSS;

CDR 1
(SEQ ID NO: 106)
GFTFSKFAMS;

CDR 2
(SEQ ID NO: 107)
ISGGSKTKY;
and

CDR 3
(SEQ ID NO: 108)
AKKGWQSTFLGMDYFYGMDV.

In certain embodiments, the CDRs comprise the three light chain CDRs of antibody 9.6.1A09 within SEQ ID NO: 109
DIVMTQSPDSLAVSLGERASINCKSSQSVLSSSNTKNYLAWYQHKPGQPP
KLLIYWASTRESGVPDRFSGSGSGTDFTLTISSLQPEDVAVYYCQQYYGA
PYTFGQGTKVEIK;

CDR 1
(SEQ ID NO: 110)
QSVLSSSNTKNY;

CDR 2
(SEQ ID NO: 111)
WASTRES;
and

CDR 3
(SEQ ID NO: 112)
QQYYGAPYT;
and the three heavy chain CDRs of antibody 9.6.1A09 within

```
                                           SEQ ID NO: 113
EVQLVESGGGLVQPGGSLRLSCAASGFTFRSYDMDWFRQSTGKGLEWVSA

IGSAGDTYYTDSVKGRFTISRENGKNSLYLQMNSLRAGDTAVYYCARARF

GDNVFDLWGRGTLVTVSS;

CDR 1
                                           (SEQ ID NO: 114)
FTFRSYDMD;

CDR 2
                                           (SEQ ID NO: 115)
IGSAGDT;
and

CDR 3
                                           (SEQ ID NO: 116)
ARFGDNVFDL.
```

In certain embodiments, the CDRs comprise
the three light chain CDRs of antibody 5.1.7D03 within

```
                                           SEQ ID NO: 117
EIVLTQSPGTLSLSPGERAALSCRASQSVSGNYFAWYQQKSGQAPRLLIS

AASSRATGVPDRFSASGSGTDFTLTISRLEPEDSAVYYCQQYGSSPLTFG

QGTKVEIK;

CDR 1
                                           (SEQ ID NO: 118)
SVSGNYFA;

CDR 2
                                           (SEQ ID NO: 119)
AASSRAT;
and

CDR 3
                                           (SEQ ID NO: 120)
QQYGSSPLT;
and
``` the three heavy chain CDRs of antibody 5.1.7D03 within

```
                                           SEQ ID NO: 121
EVQLVQSGGGLAQPGGSLRLSCAASGFTFRSYDMHWVRQVTGKGLEWVSA

IGTAGDTYYTGSVKGRFTISRENDKSSLYLQMSSLRGEDTAVYYCARAAF

GSHYFDYWGQGTLVTVSS;

CDR 1
                                           (SEQ ID NO: 122)
FTFRSYDMH;

CDR 2
                                           (SEQ ID NO: 123)
IGTAGDTYYT;
and CDR 3
                                           (SEQ ID NO: 124)
AAFGSHYFDY.
```

In certain embodiments, an antibody or antigen binding fragment thereof comprises a light chain variable region comprising the amino acid sequence of SEQ ID NO: 1, 3, 5, 7, 9, 69, 77, 85, 93, 101, 109, or 117 having at least 80, 85, 90, 95, 98, 99%, or more sequence identity or similarity thereto.

In certain embodiments, an antibody or antigen binding fragment thereof comprises a heavy chain variable region comprising the amino acid sequence of SEQ ID NO: 2, 4, 6, 8, 10, 73, 81, 89, 97, 105, 113, or 121 having at least 80, 85, 90, 95, 98, 99%, or more sequence identity or similarity thereto.

In certain embodiments, the antibody or antigen binding fragment has CDRs of SEQ ID NO: 11, 12, 13, 14, 15, and 16, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 17, 18, 19, 20, 21, and 22, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 23, 24, 25, 26, 27, and 28, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 29, 30, 31, 32, 33, and 34, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 35, 36, 37, 38, 39, and 40, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 70, 71, 72, 74, 75, and 76, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 78, 79, 80, 82, 83, and 84, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 86, 87, 88, 90, 91 and 92, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 94, 95, 96, 98, 99, and 100, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 102, 103, 104, 106, 107, and 108, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 110, 111, 112, 114, 115, and 116, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 118, 119, 120, 122, 123, and 124, wherein one, two, three, four, five, or all of the CDRs contain one, two, three, or four amino acid substitutions. In certain embodiments, the substitutions are conservative substitutions.

In certain embodiments, this disclosure relates to antibodies or antigen binding fragments comprising six complementarity determining regions (CDRs) or consensus sequences thereof, wherein the CDRs comprise the three light chain CDRs derived from an antibody selected from 2.1.1B02, 5.24.1C11, 9.20.1C03, 5.24.1B03, 9.20.1D09, 5.24.2A03, 9.20.1A02, 5.24.2C05, 5.24.2B07 and wherein the CDRs comprise the three heavy chain CDRs derived from an antibody selected from 2.1.1B02, 5.24.1C11, 9.20.1C03, 5.24.1B03, 9.20.1D09, 5.24.2A03, 9.20.1A02, 5.24.2C05, 5.24.2B07, and wherein the antibody or antigen binding fragment thereof specifically or immunospecifically binds to an epitope expressed in an Ebola virus particle.

In certain embodiments, the CDRs comprise the three light chain CDRs of antibody 2.1.1B02 within

SEQ ID NO: 125
SYELTQPPSVSVSPGQTARITCSGDALPKQYAYWYQQKPGQAPVPVIYKD

SERPSGIPERFSGSSSGTTVTLTISGVQAEDEADYYCQSSDSSGTYVVFG

GGTKLTVL;

CDR 1
(SEQ ID NO: 126)
ALPKQY;

CDR2
(SEQ ID NO: 127)
KDSE;
and

CDR3
(SEQ ID NO: 128)
QSSDSSGTYVV;
and the three heavy chain CDRs of antibody 2.1.1B02 within

SEQ ID NO: 129
EVQLVQSGAEVKKPGASVKVSCKASGYTFTSYYMHWVRQAPGQGLEWMGI

INPSGGSTSYAQKFQGRVTMTRDTSTSTVYMELSSLRSEDTAVYYCARHD

SSGYDAFDIWGQGTMVTVSS;

CDR 1
(SEQ ID NO: 130)
GYTFTSYY;

CDR 2
(SEQ ID NO: 131)
INPSGGST;
and

CDR 3
(SEQ ID NO: 132)
ARHDSSGYDAFDI.

In certain embodiments, the CDRs comprise the three light chain CDRs of antibody 5.24.1C11 within

SEQ ID NO: 133
DIVMTQSPLSLPVTPGEPASISCRSSQSLLHSNGYNYVDWYLQKPGQSPQ

LLIYLGSSRASGVPDRFSGSGSGTDFTLKISRVETEDVGIYYCMQGLQTP

LTFGGGTKVEIK;

CDR 1
(SEQ ID NO: 134)
QSLLHSNGYNY;

CDR2
(SEQ ID NO: 135)
LGSS;
and

CDR3
(SEQ ID NO: 136)
MQGLQTPLT;
and the three heavy chain CDRs of antibody 5.24.1C11 within

SEQ ID NO: 137
QVQLVQSGAEVKKPGASVKVSCRTSGYTFSSYNIHWVRQAPGQGLEWMGV

INPYGRSTTLYARRFRDRVTMTRDTSTSTVYMELSSLRSEDTAVYFCGRL

YSGAPYGLDVWGQGSTVTVSS;

CDR 1
(SEQ ID NO: 138)
GYTFSSYNIH;

CDR 2
(SEQ ID NO: 139)
PYGRSTT,
and

CDR 3
(SEQ ID NO: 140)
GRLYSGAPYGLDV.

In certain embodiments, the CDRs comprise the three light chain CDRs of antibody 9.20.1C03 within

SEQ ID NO: 141
DIVLTQSPDSLAASLGERATISCKSSHSVLYSSNNKDFFAWYQQKPGQPP

KLLISWASTRESGVPVRFNGGGSGTHFTLTISSLQAEDVAVYYCQQYFSS

PITFGQGTRLEIK;

CDR 1
(SEQ ID NO: 142)
HSVLYSSNNKDF;

CDR2
(SEQ ID NO: 143)
WAST;
and

CDR3
(SEQ ID NO: 144)
QQYFSSPIT;
and the three heavy chain CDRs of antibody 9.20.1C03 within

SEQ ID NO: 145
QVQLVQSGAEVKKPGSSVKVACKVSGGTFSSYTISWVRQAPGQGLEWMGG

IIPSFGVGHYSQKFRDRVTLTADKSTTTAFLELSSVRSEDTALYYCAILG

TFNWKSGGNYFGPWGQGTLVTVSS;

CDR1
(SEQ ID NO: 146)
GGTFSSYT;

CDR 2
(SEQ ID NO: 147)
IIPSFGVG;
and

CDR 3
(SEQ ID NO: 148)
AILGTFNWKSGGNYFGP.

In certain embodiments, the CDRs comprise the three light chain CDRs of antibody 5.24.1B03 within

SEQ ID NO: 149
ETVLTQSPNTLSLSPGERATLSCRASQSLRTNQLAWYQQKPGQAPRLLIH

TSTRATGIPDRFSGSGSGTDFTLTISGLEAEDFAVYYCQASDTSSLTFGG

GTKLEIR;

CDR 1
(SEQ ID NO: 150)
QSLRTN;

CDR2
(SEQ ID NO: 151)
HTST;
and

CDR3
(SEQ ID NO: 152)
QASDTSSLT;

and
the three heavy chain CDRs of antibody 5.24.1B03 within

SEQ ID NO: 153
QVQLQESGPGLVKPSESLSLTCTISGGSIRDYYWSWIRQAPGKGLEWIGY

KYHAARGNSNPSLESRVTMSIDTSRSEFSLRLTSVTAADTAVYYCARVQY

GPGGGYYSGNWLDLWGQGTLVTVSS;

CDR 1
(SEQ ID NO: 154)
GGSIRDYY;

CDR 2
(SEQ ID NO: 155)
KYHAARG;
and

CDR 3
(SEQ ID NO: 156)
ARVQYGPGGGYYSGNWLDL.

In certain embodiments, the CDRs comprise the three light chain CDRs of antibody 9.20.1D09 within

SEQ ID NO: 157
ETVMTQSPATLSLSPGERASLSCRASQSIATNLAWYQQKPGQPPRVLIYG

ASTRATGIPTRFSGSGSGTEFTLTISSLQSEDFAIYYCHQYHSWRTFGQG

TKVEMK;

CDR 1
(SEQ ID NO:158)
QSIATN;

CDR2
(SEQ ID NO: 159)
GAST;
and

CDR3
(SEQ ID NO: 160)
HQYHSWRT;

and
the three heavy chain CDRs of antibody 9.20.1D09 within

SEQ ID NO: 161
QLQLQESGPGLVKPSETLSLTCTVSGGSVASSNDYWGWIRQPPGKGPEWI

GTIFYRGTTDYNPSLKSRLTMSVDTSRNQFSLKLSSVTAADTAVYYCARL

PLWFSELGHDYWGQGTLVTVSS;

CDR 1
(SEQ ID NO: 162)
GGSVASSNDY;

CDR 2
(SEQ ID NO: 163)
IFYRGTT;
and

CDR 3
(SEQ ID NO: 164)
ARLPLWFSELGHDY.

In certain embodiments, the CDRs comprise the three light chain CDRs of antibody 5.24.2A03 within

SEQ ID NO: 165
QSALTQPPSASGSPGQSVTISCTGTSSDVGVYNSVSWYRQHPGKVPKLMI

YEVSKRPSGVPDRFSGSKSGNTASLTVSGLQADDEGDYYCCSCSGTNSLC

VFGTGTKVTVL;

CDR 1
(SEQ ID NO: 166)
SSDVGVYNS;

CDR2
(SEQ ID NO: 167)
EVSK;
and

CDR3
(SEQ ID NO: 168)
CSCSGTNSLCV;
and the three heavy chain CDRs of antibody 5.24.2A03 within SEQ ID NO: 169
QVQLHESGPGLVQPSETLSLTCTVSGDSITNYYWSWIRQPPGKGLEWIGY
MYYSASAHYNPSLQSRVTISVDTSKNQFSLKLSSVTAADTAVYFCARVDY
SSSSYYSGNWFDPWGQGTLVTVSS;

CDR 1
(SEQ ID NO: 170)
GDSITNYY;

CDR 2
(SEQ ID NO: 171)
MYYSASA;
and

CDR 3
(SEQ ID NO: 172)
ARVDYSSSSYYSGNWFDP

In certain embodiments, the CDRs comprise the three light chain CDRs of antibody 9.20.1A02 within SEQ ID NO: 173
QSVLTQPPSVSGAPGQTVTISCTGSYSNIGAGYDVQWYQHLPGTAPKLLI
YDNVHRPSGVPDRFSGSKSGTSASLAITGLQTEDEADYYCQSYDSRLRDQ
WVFGGGTKLTVL;

CDR 1
(SEQ ID NO: 174)
YSNIGAGYD;

CDR2
(SEQ ID NO: 175)
DNVH;
and

CDR3
(SEQ ID NO: 176)
QSYDSRLRDQWV;
and the three heavy chain CDRs of antibody 9.20.1A02 within SEQ ID NO: 177
EVQLVESGGDLVQPGGSLRLSCAASGITLSGVWMNWVRQAPGKGLEWIGR
IKSTSDGGRADFAAPARGRFTMSRDESKNKLFLQMNNLGIEDTGMYYCFT
RVQRDGTKDDFWGRGTLVTVSS;

CDR 1
(SEQ ID NO: 178)
GITLSGVW;

CDR 2
(SEQ ID NO: 179)
IKSTSDGGRA;
and

CDR 3
(SEQ ID NO: 180)
FTRVQRDGTKDDF.

In certain embodiments, the CDRs comprise the three light chain CDRs of antibody 5.24.2C05 within SEQ ID NO: 181
QSALTQPASVSGSPGQSITLSCTVGGNKFVSWYQQHPGKAPKLIISDFTD
RPSGVSSRFSGSKSGNTASLTISGLQPDDEATYFCSSYASTSTSLWVFGG
GTKLTVL;

CDR 1
(SEQ ID NO: 182)
CTVGGNKF;

CDR2
(SEQ ID NO: 183)
DFTD;
and

CDR3
(SEQ ID NO: 184)
SSYASTSTSLWV;
and the three heavy chain CDRs of antibody 5.24.2C05 within SEQ ID NO: 185
QEQLQESGPGLVKPSGTLSLTCTVSGVSVSGSYFWNWVRQPPGKGLEWLG
FIHSTGSTNTNPSLKSRVTISVDTSKNQFSLRLTSVSAADTAVYYCARAA
WLVGGEYYNYGMDLWGQGTTVTVSS;

CDR 1
(SEQ ID NO: 186)
GVSVSGSYF;

CDR 2
(SEQ ID NO: 187)
IHSTGST;

CDR 3
(SEQ ID NO: 188)
ARAAWLVGGEYYNYGMDL.

In certain embodiments, the CDRs comprise the three light chain CDRs of antibody 5.24.2B07 within SEQ ID NO: 189
GIQLTQSPSFLSASVGDRVTITCRASQGIYTYLAWYQQKPGKAPKLLVYV
ASTLQSGVPSRFSGSGSGTEFTLTISSLQPEDFATYYCQQLNSYPLTFGQ
GTKLEIK;

CDR 1
(SEQ ID NO: 190)
QGIYTY;

CDR2
(SEQ ID NO: 191)
VAST;
and

CDR3
(SEQ ID NO: 192)
QQLNSYPLT;

and
the three heavy chain CDRs of antibody 5.24.2B07 within

```
                                  SEQ ID NO: 193
QVQLVESGGGVVQPGRSLRLSCVASGFTFSSYGMHWVRQAPGKGLEWVAF

IWYDGTIQYYGDSVKGRFIISRDNSRNTLYLQMNSLRAEDTAVYYCASTL

YRNGDYGSGSRTPDDYWGQGTLVTVSS;

CDR 1
                                  (SEQ ID NO: 194)
GFTFSSYG;

CDR 2
                                  (SEQ ID NO: 195)
IWYDGTIQ;
and

CDR 3
                                  (SEQ ID NO: 196)
ASTLYRNGDYGSGSRTPDDY.
```

In certain embodiments, an antibody or antigen binding fragment thereof comprises a light chain variable region comprising the amino acid sequence of SEQ ID NO: 125, 133, 141, 149, 157, 165, 173, 181 or 189 having at least 80, 85, 90, 95, 98, 99%, or more sequence identity or similarity thereto.

In certain embodiments, an antibody or antigen binding fragment thereof comprises a heavy chain variable region comprising the amino acid sequence of SEQ ID NO: 129, 137, 145, 153, 161, 169, 177, 185, or 193 having at least 80, 85, 90, 95, 98, 99%, or more sequence identity or similarity thereto.

In certain embodiments, the antibody or antigen binding fragment has CDRs of SEQ ID NO: 126, 127, 128, 130, 131, and 132, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 134, 135, 136, 138, 139, and 140, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 142, 143, 144, 146, 147, and 148, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 150, 151, 152, 154, 155, 156, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 158 159 160, 162, 163, 164, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 166, 167, 168, 170, 171, 172, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 174, 175, 176, 178, 179, 180 wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 182, 183, 184, 186, 187, 188, wherein one, two, three, four, five, or all of the CDRs contain one, two, three, or four amino acid substitutions. In certain embodiments, the substitutions are conservative substitutions.

In certain embodiments, the antibody or antigen binding fragment has CDRs of SEQ ID NO: 190, 191, 192, 194, 195, 196, wherein one, two, three, four, five, or all of the CDRs contain one, two, three, or four amino acid substitutions. In certain embodiments, the substitutions are conservative substitutions.

In certain embodiments, the antibody, antigen binding fragment, the light chain, or the heavy chain comprises a non-naturally occurring chimeric amino acid sequence such that there is at least one mutation that is not present in naturally occurring antibodies comprising the six CDRs.

In certain embodiments, the antibody, antigen binding fragment, or heavy chain, comprises a human constant domain from an immunoglobulin constant region (Fc) having one, two, three, four, five, six, or more of the following mutations G236A, S239D, A330L, I332E, S267E, L328F, P238D, H268F, S324T, S228P, G236R, L328R, L234A, L235A, M252Y, S254T, T256E, M428L, N434S, A330L, N297A, N297Q.

In certain embodiments, this disclosure relates to antibodies comprising the triple mutation M252Y/S254T/T256E or the quadruple mutation of G236A/S239D/A330L/I332E.

In certain embodiments, antigen binding fragments disclosed herein comprises a human constant domain from an immunoglobulin constant region (Fc). In certain embodiments, the antibody or antigen fragment disclosed herein, comprising at least one amino acid substitution in the heavy chain constant region that is not present in naturally occurring antibodies comprising the six CDRs. In certain embodiments, the heavy chain comprises a sequence in a constant region that is different from any sequences present in naturally derived antibodies for which the light chain variable region comprise the three light chain CDRs and the heavy chain variable region comprise the three light chain CDRs or consensus sequences thereof.

In certain embodiments, the epitope expressed on an Ebola virus particle is arrayed on a surface, expressed on the surface of a cell, or expressed at an endogenous or transfected concentration, and the antibody or antigen binding fragment is bound to the epitope.

In certain embodiments, the antibody or antigen binding fragment is capable inducing an immune response to the Ebola virus or capable of neutralizing an of Ebola virus from replicating.

In certain embodiments, the disclosure relates to nucleic acids encoding an antibody or antigen binding fragment disclosed herein or a vector or expression system comprising such a nucleic acid. In certain embodiments, the disclosure relates to nucleic acids disclosed herein and variants which are synonymous mutations and non-synonymous mutations, e.g., codon optimized mutations.

In certain embodiments, the antibody or antigen binding fragment thereof is detectably labeled or comprises a conjugated toxin, drug, receptor, enzyme, receptor ligand.

In certain embodiments, the disclosure relates to pharmaceutical compositions comprising the antibody or antigen binding fragment thereof disclosed herein, and a physiologically acceptable carrier or excipient.

In certain embodiments, the disclosure relates to methods of detection Ebola virus infection, comprising: (a) assaying the expression of Ebola virus epitope in cells or in a tissue sample of a subject using the antibody or antigen binding fragment thereof disclosed herein and (b) comparing the level of the Ebola virus epitope with a control level, wherein an increase in the assayed level of Ebola virus compared to the control level is indicative of the infection.

In certain embodiments, the expression of Ebola virus epitope is assayed by enzyme linked immunosorbent assay (ELISA), radioimmunoassay (RIA), or fluorescence-activated cell sorting (FACS).

In certain embodiments, the disclosure relates to methods of preventing or treating an Ebola virus infection comprising administering an effective amount of a pharmaceutical composition disclosed herein to a subject in need thereof. In certain embodiments, the subject is at risk of, exhibiting symptoms of, or diagnosed with an Ebola virus infection.

BRIEF DESCRIPTION OF THE DRAWINGS

FIG. 2 illustrates nucleic acid sequences encoding and amino acid sequences for the heavy (right) and light (left) variable regions of antibodies 5.1.10B3 and 5.6.1A02.

FIG. 3 illustrates nucleic acid sequences encoding and amino acid sequences for the heavy (right) and light (left) variable regions of antibodies 2.1.1D05 and 2.1.1D07.

FIG. 8 illustrates nucleic acid sequences for the heavy (right) and light (left) variable regions of antibodies 2.1.1B02, 5.24.1C11 and 9.20.1CB3.

FIG. 9 illustrates nucleic acid sequences for the heavy (right) and light (left) variable regions of antibodies 5.24.1B3, 9.20.1D09 and 5.24.2A03.

FIG. 10 illustrates nucleic acid sequences for the heavy (right) and light (left) variable regions of antibodies 9.20.1A02, 5.24.2C05 and 5.24.2B07.

DETAILED DESCRIPTION

Figure 1:
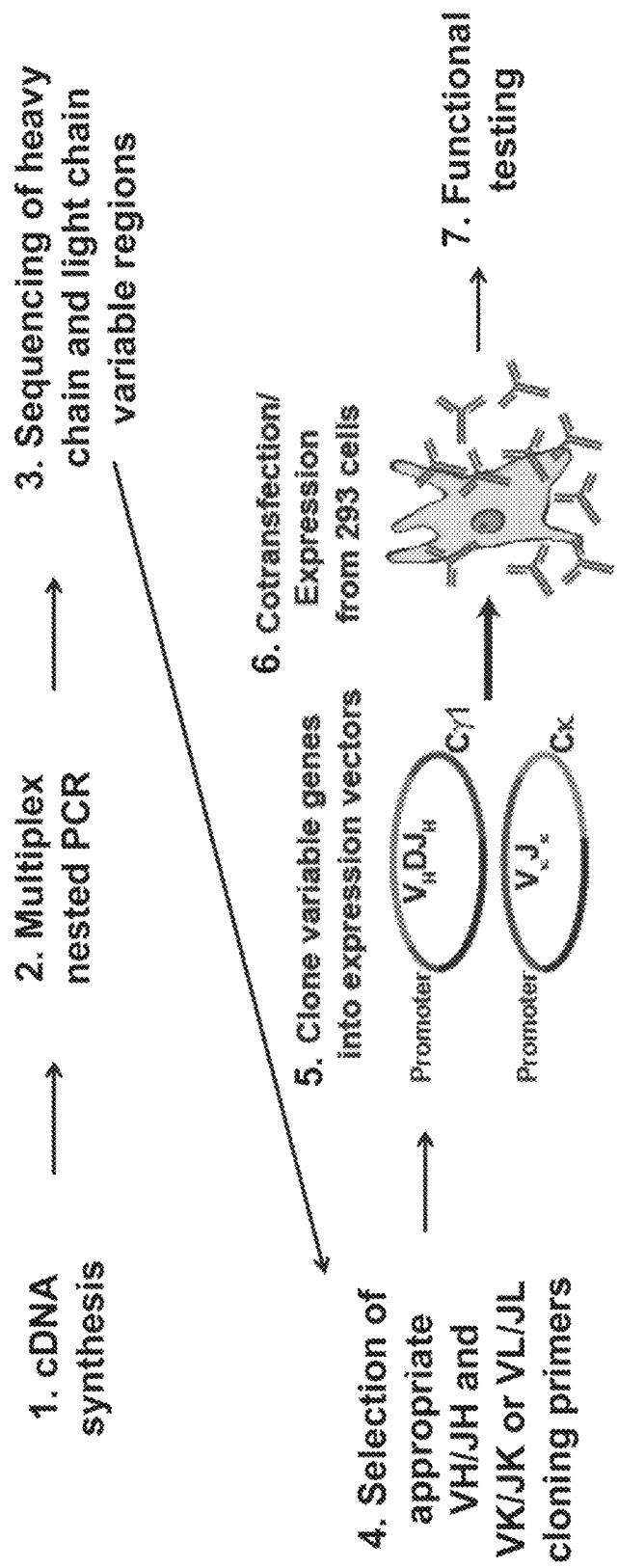
FIG. 1 illustrates a method of isolating variable antibody sequences from cells and grafting them to human constant regions.
Figures 4, 5:
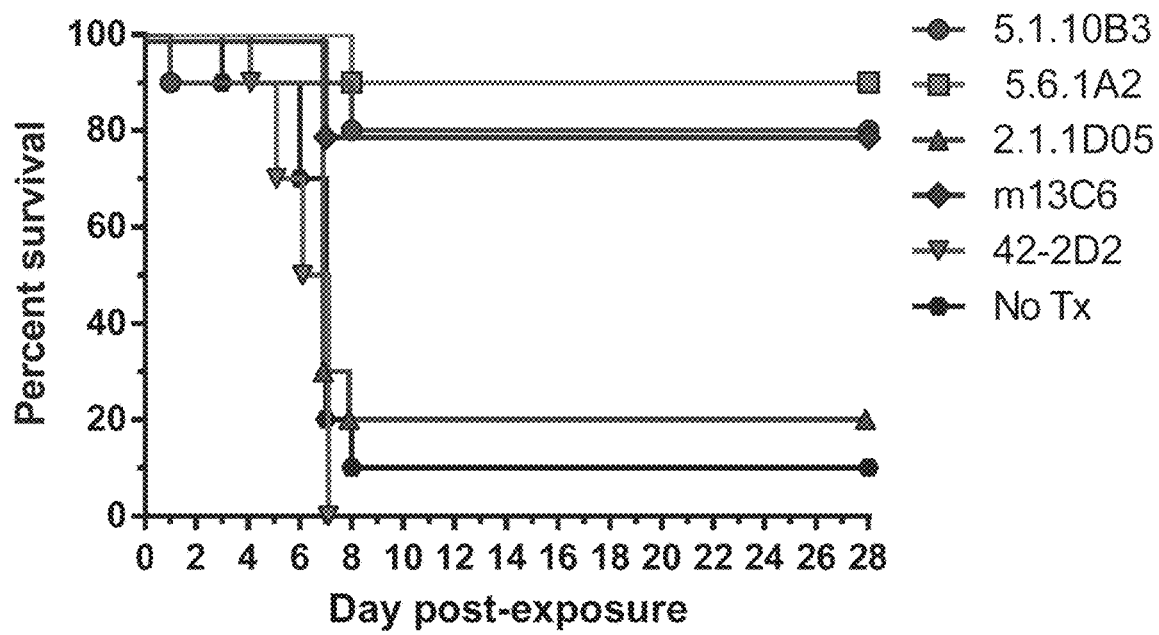
FIG. 4 illustrates nucleic acid sequences encoding and amino acid sequences for the heavy (right) and light (left) variable regions of antibody 9.6.3D06.
FIG. 5 shows data on antibodies against maEVOV in BALB/c mice. Mice were given 100 ug of the indicated mAbs 24 hours prior to challenge with 100 pfu of Ebola Zaire (Mayinga strain). Note: C13C6 is a previously described antibody and component of Zmapp that was included as a control. 42-2D2 is an influenza specific negative control mAb made at Emory.
Figure 6:
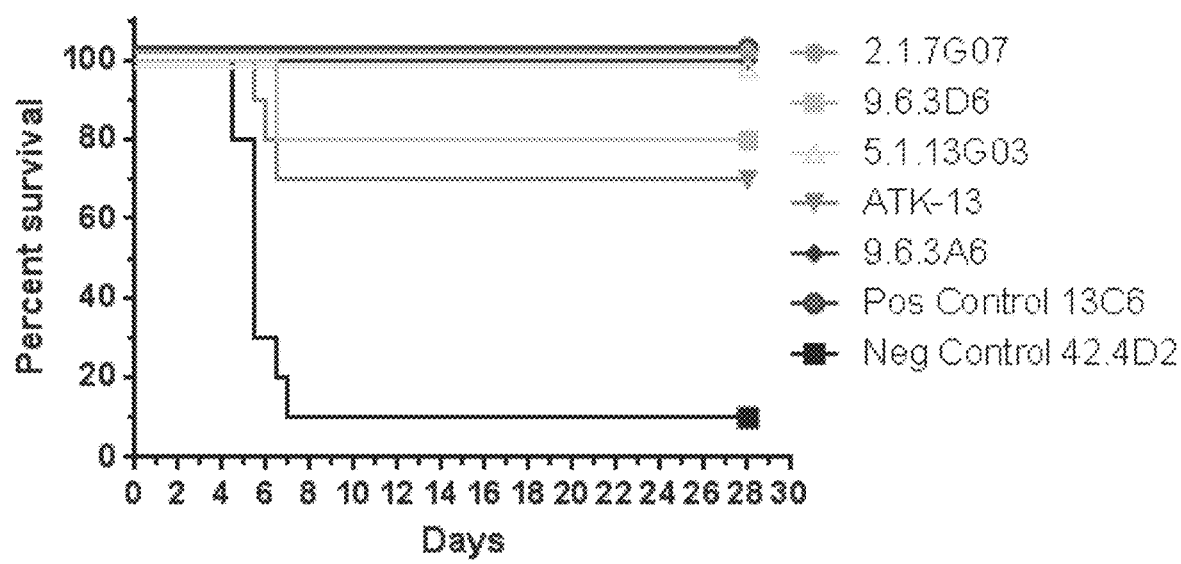
FIG. 6 shows data on antibodies. Mice were given 100 ug of the indicated mAbs 24 hours prior to challenge with 100 pfu of Ebola Zaire (Mayinga strain). Note: ATK-13 is the same as 5.6.c2618.
Figure 7:
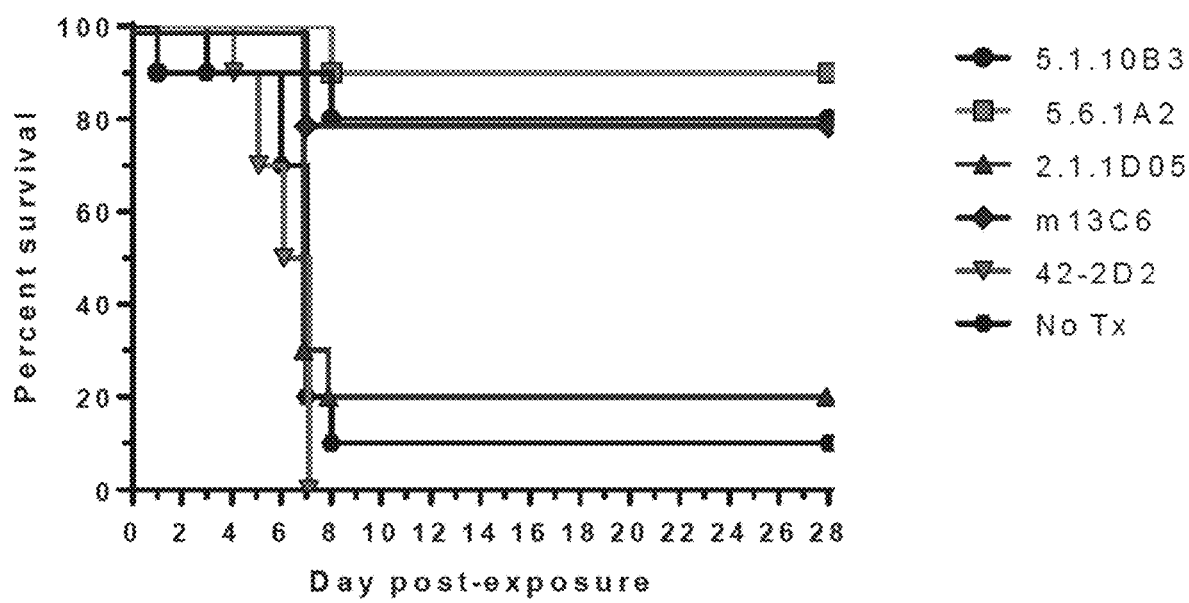
FIG. 7 shows data on antibodies against maEBOV in BALB/c Mice. Mice were given 100 ug of the indicated mAbs 24 hours prior to challenge with 100 pfu of Ebola Zaire (Mayinga strain). Note: C13C6 is a previously described antibody and component of Zmapp that was included as a control. 42-2D2 is an influenza specific negative control mAb made at Emory.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In the claims appended hereto, the term "a" or "an" is intended to mean "one or more," and the term "comprise" and variations thereof such as "comprises" and "comprising," when preceding the recitation of a step or an element, are intended to mean that the addition of further steps or elements is optional and not excluded.

As used herein, the terms "treat," "treating," "treatment" and "therapeutic use" refer to the elimination, reduction or amelioration of one or more symptoms of a disease or disorder that would benefit from an increased or decreased immune response. As used herein, a "therapeutically effective amount" refers to that amount of a therapeutic agent sufficient to mediate an altered immune response, and more preferably, a clinically relevant altered immune response, sufficient to mediate a reduction or amelioration of a symptom. An effect is clinically relevant if its magnitude is sufficient to impact the health or prognosis of a recipient subject. A therapeutically effective amount refers to the amount of the therapeutic agent that provides a therapeutic benefit in the treatment.

The term "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human patient.

The term "sample" refers to any mixture of biological materials derived from a subject, e.g., bodily fluids, whole blood, serum, plasma, tissue, skin, saliva, urine, stool, tears, amniotic fluid, breast milk etc. Biological samples may be obtained from animals (including humans) and encompass fluids, solids, tissues, and gases.

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

The term "substantially," as used in the context of binding or exhibited effect, is intended to denote that the observed effect is physiologically or therapeutically relevant. Thus, for example, a molecule is able to substantially block an activity of an Ebola virus if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5′ phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferaseI (galT), feedback-insensitive a subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as 35S or 131I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to antibodies and antigen binding fragments comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to vectors comprising a nucleic acid encoding an antibody or antigen binding fragment disclosed herein or chimeric protein thereof.

In certain embodiments, the vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides

GGGGGG (SEQ ID NO: 215)

and

GGGGT (SEQ ID NO: 216)

have a sequence identity of 4 out of 5 or 80%. For example, the polypeptides

GGGPPP (SEQ ID NO: 217)

and

GGGAPPP (SEQ ID NO: 218)

have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

As used herein, the term "combination with" when used to describe administration with an additional treatment means that the agent may be administered prior to, together with, or after the additional treatment, or a combination thereof.

Ebola Virus

Ebola is a deadly disease caused by infection with one of the Ebola virus species. The disease is spread through direct contact with bodily fluids, contaminated objects, infected fruit bats or primates, or from sexual contact. In a period from 3-21 days, Ebola virus causes symptoms such as fever, muscle pain, and vomiting, and can also lead to unexplained hemorrhage and, if left untreated, eventually death. Although it is considered a rare disease, in 2014, the largest Ebola outbreak in history nucleated in West Africa (Guinea) and was thought to be caused by a new Ebola virus strain.

Ebola viruses are categorized in the family Filoviridae and typically cause severe hemorrhagic fevers and fatalities in humans. Ebola viruses include Zaire Ebola virus (EBOV), Sudan virus (SUDV), Tai forest virus (TAFV), Bundibugyo virus (BDBV), and Reston virus (RESTV). The Ebolavirus virion core consists of the negative-sense RNA genome. The core is surrounded by a lipid envelope with surface projections that are comprised of a glycoprotein (GP).

Ebola viruses are RNA viruses that are thread-like in appearance and consist of seven structural proteins including glycoprotein, matrix proteins, and nucleocapsid proteins. Virus particles are surrounded by a host cell-derived membrane in which the surface glycoprotein GP is embedded.

Typically, survival from an Ebola viral infection depends on access to adequate healthcare early in disease progression. Treatment consists of providing fluids, maintaining oxygen and blood pressure, and treating other infections. Survivors do develop antibodies against Ebola virus that may persist for up to 10 years.

Ebola virus infections typically result in with onset of fever and chills, but low-grade fever and malaise may also precede the development of more severe symptoms. Watery diarrhea nausea, vomiting, and abdominal pain are common. Gastrointestinal bleeding, blood in the stool, and mucosal bleeding may occur. Blurred vision, photophobia, blindness may occur during the acute phase of illness. A diffuse erythematous, nonpruritic maculopapular rash may develop. The rash usually involves the face, neck, trunk, and arms, and can desquamate. Multi-organ failure with death typically occurring in the second week.

The presence of the Ebola virus can be done by the detection of viral RNA, e.g. by RT-PCR, and/or by detection of Ebola antigen by a specific Antigen detection test, and/or by detection of immunoglobulin M (IgM) antibodies directed against Ebola.

Antibody and Antigen Binding Fragments

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to the disclosed B7-H5 antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind an antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, non-naturally occurring chimeric or humanized derivatives of anti-Ebola virus antibodies are particularly preferred for in vivo use in humans, however, murine antibodies or antibodies of other species may be advantageously employed for many uses (for example, in vitro or in situ detection assays, acute in vivo use, etc.). A humanized antibody may comprise amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of an Ebola virus polypeptide.

Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such that the entire molecule is not naturally occurring. Examples of chimeric antibodies include those having a variable region derived from a non-human antibody and a human immunoglobulin constant region. The term is also intended to include antibodies having a variable region derived from one human antibody grafted to an immunoglobulin constant region of a predetermined sequences or the constant region from another human for which there are allotypic differences residing in the constant regions of any naturally occurring antibody having the variable regions, e.g., CDRs 1, 2, and 3 of the light and heavy chain. Human heavy chain genes exhibit structural polymorphism (allotypes) that are inherited as a haplotype. The serologically defined allotypes differ within and between population groups. See Jefferis et al. mAb, 1 (2009), pp. 332-338.

Smith et al. report a protocol for the production of antigen-specific chimeric human monoclonal antibodies (hmAbs) wherein antibody-secreting cells (ASCs) are isolated from whole blood collected after vaccination and sorted by flow cytometry into single cell plates. Nat Protoc. 2009; 4(3):372-84. The antibody genes of the ASCs are then amplified by RT-PCR and nested PCR, cloned into expression vectors and transfected into a human cell line. Meijer et al. report methods for isolation of human antibody repertoires with preservation of the natural heavy and light chain pairing. J Mol Biol. 2006 May 5; 358(3):764-72. Wrammert et al. report using immunoglobulin variable regions isolated from sorted single ASCs to produce human monoclonal antibodies (mAbs) that bound with high affinity. Nature. 2008 May 29; 453(7195): 667-671.

Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an Fc RIIB polypeptide, that has been altered by the introduction of amino acid residue substitutions, deletions or additions (i.e., mutations).

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "Structural Determinants In the Sequences of Immunoglobulin Variable Domain," J. Mol. Biol. 278: 457-479 for a listing of human framework regions).

A humanized or non-naturally occurring chimeric Ebola virus antibody can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, an Ebola virus antibody also includes at least a portion of an immunoglobulin constant region (Fc), typically that of a human immunoglobulin. The constant domains of the Ebola virus antibodies may be selected with respect to the proposed function of the antibody, in particular the effector function which may be required. In some embodiments, the constant domains of the Ebola virus antibodies are (or comprise) human IgA, IgD, IgE, IgG or IgM domains. In a specific embodiment, human IgG constant domains, especially of the IgG1 and IgG3 isotypes are used, when the humanized Ebola virus antibodies is intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the Ebola virus antibody is intended for therapeutic purposes and antibody effector function is not required. The disclosure encompasses Fc constant domains comprising one or more amino acid modifications which alter antibody effector functions such as those disclosed in U.S. Patent Application Publication Nos. 2005/0037000 and 2005/0064514.

In some embodiments, the Ebola virus antibody contains both the light chain as well as at least the variable domain of a heavy chain. In other embodiments, the Ebola virus antibody may further include one or more of the CH1, hinge, CH2, CH3, and CH4 regions of the heavy chain. The antibody can be selected from any class of immunoglobulins, including IgM, IgG, IgD, IgA and IgE, and any isotype, including IgG1, IgG2, IgG3 and IgG4. In some embodiments, the constant domain is a complement fixing constant domain where it is desired that the antibody exhibit cytotoxic activity, and the class is typically IgG1. In other embodiments, where such cytotoxic activity is not desirable, the constant domain may be of the IgG2 class. The Ebola virus antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc. Natl. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

The antibodies used in the methods of the present disclosure may be monospecific. Also of interest are bispecific antibodies, trispecific antibodies or antibodies of greater multispecificity that exhibit specificity to different targets in the Ebola virus.

The antibodies of the present disclosure may be produced by any method known in the art useful for the production of polypeptides, e.g., in vitro synthesis, recombinant DNA production, and the like. Preferably, the antibodies are produced by recombinant DNA technology. The Ebola virus antibodies may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

Host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant Ebola virus antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the antibodies disclosed herein can be used to generate antiidiotype antibodies using techniques well known to those skilled in the art (see, e.g., Greenspan, N. S. et al. (1989) "Idiotypes: Structure and Immunogenicity," FASEB J. 7:437-444; and Nisinoff, A. (1991) "Idiotypes: Concepts and Applications," J. Immunol. 147(8):2429-2438).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present disclosure include those disclosed in Brinkman, U. et al. (1995) "Phage Display Of Disulfide-Stabilized Fv Fragments," J. Immunol. Methods, 182:41-50, 1995; Ames, R. S. et al. (1995) "Conversion Of Murine Fabs Isolated From A Combinatorial Phage Display Library To Full Length Immunoglobulins," J. Immunol. Methods, 184:177-186; Kettleborough, C. A. et al. (1994) "Isolation Of Tumor Cell-Specific Single-Chain Fv From Immunized Mice Using Phage-Antibody Libraries And The Re-Construction Of Whole Antibodies From These Antibody Fragments," Eur. J. Immunol., 24:952-958, 1994; Persic, L. et al. (1997) "An Integrated Vector System For The Eukaryotic Expression Of Antibodies Or Their Fragments After Selection From Phage Display Libraries," Gene, 187:9-18; Burton, D. R. et al. (1994) "Human Antibodies From Combinatorial Libraries," Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art (such as those disclosed in PCT Publication WO 92/22324; Mullinax, R. L. et al. (1992) "Expression Of A Heterodimeric Fab Antibody Protein In One Cloning Step," BioTechniques, 12(6):864-869; and Sawai et al. (1995) "Direct Production Of The Fab Fragment Derived From The Sperm Immobilizing Antibody Using Polymerase Chain Reaction And cDNA Expression Vectors," Am. J. Reprod. Immunol. 34:26-34; and Better, M. et al. (1988) "*Escherichia coli* Secretion of an Active Chimeric Antibody Fragment," Science 240:1041-1043). Examples of techniques which can be used to produce single-chain Fvs and antibodies include those described in U.S. Pat. Nos. 4,946,778 and 5,258,498; Huston, J. S. et al. (1991) "Protein Engineering of Single-Chain Fv Analogs and Fusion Proteins," Methods in Enzymology 203:46-88; Shu, L. et al., "Secretion of a Single-Gene-Encoded Immunoglobulin from Myeloma Cells," Proc. Natl. Acad. Sci. (USA) 90:7995-7999; and Skerra. A. et al. (1988) "Assembly of a Functional Immunoglobulin Fv Fragment in *Escherichia coli*," Science 240:1038-1040.

Phage display technology can be used to increase the affinity of an antibody for Ebola virus. This technique would be useful in obtaining high affinity antibodies that could be used in the disclosed combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "Antibody Engineering by Codon-Based Mutagenesis in a Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "Stepwise In Vitro Affinity Maturation Of Vitaxin, An Alphav Beta3-Specific Humanized Mab," Proc. Natl. Acad. Sci. (USA) 95(11): 6037-6042; Yelton, D. E. et al. (1995) "Affinity Maturation Of The BR96 Anti-Carcinoma Antibody By Codon-Based Mutagenesis," J. Immunol. 155:1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567).

The disclosure contemplates the use of random mutagenesis to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see, Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155: 1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567).

Methods for accomplishing such affinity maturation are described for example in: Krause, J. C. et al. (2011) "An Insertion Mutation that Distorts Antibody Binding Site Architecture Enhances Function of a Human Antibody," MBio. 2(1) pii: e00345-10. doi: 10.1128/mBio.00345-10; Kuan, C. T. et al. (2010) "Affinity-Matured Anti-Glycoprotein NMB Recombinant Immunotoxins Targeting Malignant Gliomas and Melanomas," Int. J. Cancer 10.1002/ijc.25645; Hackel, B. J. et al. (2010) "Stability and CDR Composition Biases Enrich Binder Functionality Landscapes," J. Mol. Biol. 401(1):84-96; Montgomery, D. L. et al. (2009) "Affinity Maturation and Characterization of a Human Monoclonal Antibody Against HIV-1 gp41," MAbs 1(5):462-474; Gustchina, E. et al. (2009) "Affinity Maturation By Targeted Diversification of the CDR-H2 Loop of a Monoclonal Fab Derived From A Synthetic Naive Human Antibody Library And Directed Against The Internal Trimeric Coiled-Coil Of Gp41 Yields A Set Of Fabs With Improved HIV-1 Neutralization Potency And Breadth," Virology 393(1):112-119; Finlay, W. J. et al. (2009) "Affinity Maturation of a Humanized Rat Antibody ror Anti-RAGE Therapy: Comprehensive Mutagenesis Reveals a High Level of Mutational Plasticity Both Inside and Outside the Complementarity-Determining Regions," J. Mol. Biol. 388(3):541-558; Bostrom, J. et al. (2009) "Improving Antibody Binding Affinity and Specificity for Therapeutic Development," Methods Mol. Biol. 525:353-376; Steidl, S. et al. (2008) "In Vitro Affinity Maturation of Human GM-CSF Antibodies by Targeted CDR-Diversification," Mol. Immunol. 46(1):135-144; and Barderas, R. et al. (2008) "Affinity Maturation of Antibodies Assisted by in Silico Modeling," Proc. Natl. Acad. Sci. (USA) 105(26):9029-9034.

In certain embodiments, the antibody, antigen binding fragment, the light chain, or the heavy chain comprises a non-naturally occurring chimeric amino acid sequence such that there is at least one mutation that is not present in naturally occurring antibodies comprising the six CDRs. In certain embodiments, the antibody, antigen binding fragment, or heavy chain, comprises a human constant domain from an immunoglobulin constant region (Fc) having one, two, three, four, five, six, or more of the following mutations G236A, S239D, A330L, I332E, S267E, L328F, P238D, H268F, S324T, S228P, G236R, L328R, L234A, L235A, M252Y, S254T, T256E, M428L, N434S. With regard to IgG-1 Fc mutations reported herein the sequences are in reference to following amino acid sequence (SEQ ID NO: 50) starting at amino acid 119:

```
STKGPSVFP LAPSSKSTSG GTAALGCLVK DYFPEPVTVS WNSGALTSGV HTFPAVLQSS 178

GLYSLSSVVT VPSSSLGTQT YICNVNHKPS NTKVDKKVEP KSCDKTHTCP PCPAPELLGG 238

PSVFLFPPKP KDTLMISRTP EVTCVVVDVS HEDPEVKFNW YVDGVEVHNAKTKPREEQYN 298

STYRVVSVLT VLHQDWLNGK EYKCKVSNKA LPAPIEKTIS KAKGQPREPQ VYTLPPSRDE 358

LTKNQVSLTC LVKGFYPSDI AVEWESNGQP ENNYKTTPPV LDSDGSFFLY SKLTVDKSRW 418

QQGNVFSCSV MHEALHNHYT QKSLSLSPG.
```

In certain embodiments, In certain embodiments, this disclosure relates to antibodies reported wherein the constant region comprises a mutation that activates immune responses such as those selected from the constant region comprises as least one, two, three, or more mutations in the Fc domain selected from S239D, I332E, G236A, A330L, or combinations thereof.

FcgRIIb has immunosuppressive function. In certain embodiments, this disclosure relates to antibodies reported wherein the constant region comprises a mutation that suppressed immune responses those selected from the constant region comprises as least one, two, three, or more mutations in the Fc domain selected from S267E, L328F, P238D, or combinations thereof.

Antibodies interact with the complement cascade through C1q binding enabling antibodies to activate complement-dependent cytotoxicity (CDC). In certain embodiments, this disclosure relates to antibodies reported wherein the constant region comprises a mutation that effectively active complement-dependent cytotoxicity such as those selected from S267E, H268F, S324T, and combinations thereof.

In certain embodiment interaction with the immune system through Fc receptors may be unnecessary or undesirable, i.e., immune-silent antibodies. In certain embodiments, this disclosure relates to antibodies reported wherein the constant region comprises a mutation that bind the antigen but do not bind to FcgRs such as those selected from S228P, G236R, L328R, L234A, L235A, or combinations thereof.

In certain embodiments, is may be desirable to have antibodies wherein constant region of the Fc has been to increase or decrease antibody half-life. In certain embodiments, this disclosure relates to antibodies reported wherein the constant region comprises a mutation that increases or decreases the antibodies half-life such as those selected from M252Y, S254T, T256E, M428L, N434S or combinations thereof.

The disclosure particularly contemplates the production and use of "derivatives" of any of the above-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies, as well as variants having altered CH1, hinge, CH2, CH3 or CH4 regions, so as to form, for example antibodies, etc., having variant Fc regions that exhibit enhanced or impaired effector or binding characteristics.

The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "Lack of Fucose on Human IgG N-Linked Oligosaccharide Improves Binding to Human Fcgamma RIII and Antibody-Dependent Cellular Toxicity," J. Biol. Chem. 277(30): 26733-26740; Davies J. et al. (2001) "Expression of GnTIII in a Recombinant Anti-CD20 CHO Production Cell Line: Expression of Antibodies with Altered Glycoforms Leads to an Increase In ADCC Through Higher Affinity For FC Gamma RIII," Biotechnology & Bioengineering 74(4): 288-294). Methods of altering carbohydrate contents are known to those skilled in the art, see, e.g., Wallick, S. C. et al. (1988) "Glycosylation of a VH Residue of a Monoclonal Antibody Against Alpha (1-6) Dextran Increases its Affinity for Antigen," J. Exp. Med. 168(3): 1099-1109; Tao, M. H. et al. (1989) "Studies of Aglycosylated Chimeric Mouse-Human IgG. Role of Carbohydrate in the Structure and Effector Functions Mediated by the Human IgG Constant Region," J. Immunol. 143(8): 2595-2601; Routledge, E. G. et al. (1995) "The Effect of Aglycosylation on the Immunogenicity of a Humanized Therapeutic CD3 Monoclonal Antibody," Transplantation 60(8):847-53; Elliott, S. et al. (2003) "Enhancement of Therapeutic Protein in Vivo Activities Through Glycoengineering," Nature Biotechnol. 21:414-21; Shields, R. L. et al. (2002) "Lack of Fucose on Human IgG N-Linked Oligosaccharide Improves Binding to Human Fcgamma RIII and Antibody-Dependent Cellular Toxicity," J. Biol. Chem. 277(30): 26733-26740).

In some embodiments, a humanized antibody is a derivative. Such a humanized antibody comprises amino acid residue substitutions, deletions or additions in one or more CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present disclosure or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The Ebola virus antibodies can be engineered to increase biological half-lives (see, e.g. U.S. Pat. No. 6,277,375). For example, Ebola virus antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The Ebola virus antibodies may also be modified by the methods and coupling agents described by Davis et al. (See U.S. Pat. No. 4,179,337) in order to provide compositions that can be injected into the mammalian circulatory system with substantially no immunogenic response.

One embodiment encompasses modification of framework residues of the Ebola virus antibodies. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "Reshaping Human Antibodies for Therapy," Nature 332:323-327).

Yet another embodiment encompasses Ebola virus antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., alpha-interferon, beta-interferon), nerve growth factor, platelet derived growth factor, tissue plasminogen activator, or an apoptotic agent (e.g., tumor necrosis factor-alpha, tumor necrosis factor-bet.)), biological response modifiers (such as, for example, alymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU™ (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or antimitotic agents (e.g., vincristine and vinblastine).

Techniques for conjugating such therapeutic moieties to antibodies are well known; see, e.g., Arnon et al., "Monoclonal Antibodies for Immunotargeting of Drugs in Cancer Therapy", in MONOCLONAL ANTIBODIES AND CANCER THERAPY, Reisfeld et al. (eds.), 1985, pp. 243-56, Alan R. Liss, Inc.); Hellstrom et al., "Antibodies for Drug Delivery", in CONTROLLED DRUG DELIVERY (2nd Ed.), Robinson et al. (eds.), 1987, pp. 623-53, Marcel Dekker, Inc.); Thorpe, "Antibody Carriers of Cytotoxic Agents in Cancer Therapy: A Review", in MONOCLONAL ANTIBODIES '84: BIOLOGICAL AND CLINICAL APPLICATIONS, Pinchera et al. (eds.), 1985, pp. 475-506); "Analysis, Results, and Future Prospective of the Therapeutic Use of Radiolabeled Antibody in Cancer Therapy", in MONOCLONAL ANTIBODIES FOR CANCER DETECTION AND THERAPY, Baldwin et al. (eds.), 1985, pp. 303-16, Academic Press; and Thorpe et al. (1982) "The Preparation and Cytotoxic Properties of Antibody-Toxin Conjugates," Immunol. Rev. 62:119-158.

In one embodiment, the Ebola virus antibodies or Ebola virus fusion molecules include an Fc portion. The Fc portion of such molecules may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "Humanized Porcine VCAM-Specific Monoclonal Antibodies with Chimeric IgG2/G4 Constant Regions Block Human Leukocyte Binding to Porcine Endothelial Cells," Mol. Immun 34(6):441-452, Swann, P. G. (2008) "Considerations for the Development of Therapeutic Monoclonal Antibodies," Curr. Opin. Immun. 20:493-499 (2008), and Presta, L. G. (2008) "Molecular Engineering and Design of Therapeutic Antibodies," Curr. Opin. Immun 20:460-470. In some embodiments, the Fc region is the native IgG1, IgG2, or IgG4 Fc region. In some embodiments, the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn, and IgG4 with serine at amino acid resident #228 in the hinge region changed to proline (S228P) to enhance stability. The Fc region may include the entire hinge region, or less than the entire hinge region.

Another embodiment includes IgG2-4 hybrids and IgG4 mutants that have reduced binding to FcR which increase their half-life. Representative IG2-4 hybrids and IgG4 mutants are described in Angal, S. et al. (1993) "A Single Amino Acid Substitution Abolishes the Heterogeneity of Chimeric Mouse/Human (IgG4) Antibody," Molec. Immunol. 30(1):105-108; Mueller, J. P. et al. (1997) "Humanized Porcine VCAM-Specific Monoclonal Antibodies With Chimeric IgG2/G4 Constant Regions Block Human Leukocyte Binding To Porcine Endothelial Cells," Mol. Immun 34(6):441-452; and U.S. Pat. No. 6,982,323. In some embodiments the IgG1 and/or IgG2 domain is deleted for example, Angal, s. et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

Substitutions, additions or deletions in the derivatized antibodies may be in the Fc region of the antibody and may thereby serve to modify the binding affinity of the antibody to one or more Fc R. Methods for modifying antibodies with modified binding to one or more Fc R are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1 q binding activity, an altered complement-dependent cytotoxicity activity (CDC), a phagocytic activity, or any combination thereof.

In some embodiments, the disclosure encompasses antibodies whose Fc region will have been modified so that the molecule will exhibit altered Fc receptor (FcR) binding activity, for example to exhibit decreased activity toward activating receptors such as FcgammaRIIA or FcgammaRIIIA, or increased activity toward inhibitory receptors such as FcgammaRIIB. Preferably, such antibodies will exhibit decreased antibody-dependent cell-mediated cytotoxicity (ADCC) or complement dependent cytotoxicity (CDC) activities (relative to a wild-type Fc receptor).

Modifications that affect Fc-mediated effector function are well known in the art (see U.S. Pat. No. 6,194,551, and WO 00/42072; Stavenhagen, J. B. et al. (2007) "Fc Optimization Of Therapeutic Antibodies Enhances Their Ability To Kill Tumor Cells In Vitro And Controls Tumor Expansion In Vivo Via Low-Affinity Activating Fcgamma Receptors," Cancer Res. 57(18):8882-8890; Shields, R. L. et al. (2001) "High Resolution Mapping of the Binding Site on Human IgG1 for FcgammaRI, FcgammaRII, FcgammaRIII, and FcRn and Design of IgG1 Variants with Improved Binding to the Fc.gamma.R," J. Biol. Chem. 276(9):6591-6604). Exemplary variants of human IgG1 Fc domains with reduced binding to FcgammaRIIA or FcgammaRIIIA, but unchanged or enhanced binding to FcgammaRIIB, include S239A, H268A, S267G, E269A, E293A, E293D, Y296F, R301A, V303A, A327G, K322A, E333A, K334A, K338A, A339A, D376A.

In some embodiments, the disclosure encompasses antibodies whose Fc region will have been deleted (for example, an Fab or F(ab)$_2$, etc.).

Any of the molecules of the present disclosure can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "The Structure Of An Antigenic Determinant In A Protein," Cell, 37:767-778) and the "flag" tag (Knappik, A. et al. (1994) "An Improved Affinity Tag Based On The FLAG Peptide For The Detection And Purification Of Recombinant Antibody Fragments," Biotechniques 17(4):754-761).

In some embodiments, the antigen binding fragments may comprise one, two, or more of the CDRs or variable regions, e.g., a light chain variable region having a flexible linker such as a polyglycine, linked to the heavy chain variable region which is further fused to a polypeptide having a signal-transduction component of a T-cell antigen receptor domain, e.g., constant Fc domain or CD3-zeta. In certain embodiments, the signal-transduction component of the T-cell antigen receptor is a peptide with an immunoreceptor tyrosine-based activation motif with the consensus sequence YXXL(X)$_n$YXXL (SEQ ID NO: 61) wherein X is any amino acid L is leucine or isoleucine, wherein n is 6, 7, or 8. For example, the immunoreceptor tyrosine-based activation motif (underlined) is in the partial CD3-zeta sequences:

(SEQ ID NO: 62)
AQLPITEAQSFGLLDPKLCYLLDGILFIYGVILTALFLRVKFSRSADAPA

YQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPR or (SEQ ID NO: 63)
AQLPITEAQSFGLLDPKLCYLLDGILFIYGVILTALFLRVKFSRSADAPA

YQQGQNQLYNELNLGRREEYDVLDKRRGRDPEMGGKPQRRKNPQEGL

YNELQKDKMAEAYSEIGMKGERRRGKGHDGLYQGLSTATKDTYDALHMQA

LPPR or (SEQ ID NO: 64)
AQLPITEAQSFGLLDPKLCYLLDGILFIYGVILTALFLRVKFSRSAEPPA

YQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPRAQLPITEAQSFGLLDPK or fragments or variants, e.g. having 1, 2, or 3 amino acid deletion, addition, or substitution variants, or a sequence with greater than 50, 60, 70, 80, 90, 95% or greater identity thereto.

In certain embodiments, the signal-transduction component of the T-cell antigen receptor is a peptide with a immunoreceptor tyrosine-based activation motif (underlined) with the sequence of immunoglobulin epsilon receptor subunit gamma precursor (SEQ ID NO: 65)
EPQLCYILDAILFLYGIVLTLLYCRLKIQVRKAAITSYEKSDGV

YTGLSTRNQETYETLKHE fragments or variants thereof variants or a sequence with greater than 50, 60, 70, 80, 90, 95% or greater identity thereto.

The present disclosure also encompasses antibodies or their antigen-binding fragments that are conjugated to a diagnostic or therapeutic agent or any other molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present disclosure.

Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In) iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium (103Pd), phosphorous ($^{32}$P), praseodymium ($^{142}$Pr), promethium, ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$YB, $^{175}$Yb) yttrium ($^{90}$Y), zinc ($^{65}$Zn); positron emitting metals using various positron emission tomographies, and nonradioactive paramagnetic metal ions.

The molecules of the present disclosure can be conjugated to a second antibody to form an antibody heteroconjugate as described by Segal in U.S. Pat. No. 4,676,980. Such heteroconjugate antibodies may additionally bind to haptens (such as fluorescein, etc.), or to cellular markers (e.g., PD-1, 4-1-BB, B7-H4, B7-H5, CD4, CD8, CD14, CD25, CD27, CD28, CD40, CD68, CD163, CTLA4, GITR, LAG-3, OX40, TIM3, TIM4, TLR2, LIGHT, etc.) or to cytokines (e.g., IL-7, IL-15, IL-12, IL-4 TGF-beta, IL-10, IL-17, IFNg, Flt3, BLys) or chemokines (e.g., CCL21), etc.

The molecules of the present disclosure may be attached to solid supports, which are particularly useful for immunoassays or purification of the target antigen or of other molecules that are capable of binding to target antigen that has been immobilized to the support via binding to an antibody or antigen-binding fragment of the present disclosure. Such solid supports include, but are not limited to, glass, cellulose, polyacrylamide, nylon, polystyrene, polyvinyl chloride or polypropylene.

The present disclosure additionally includes nucleic acid molecules (DNA or RNA) that encode any such antibodies, fusion proteins or fragments, as well as vector molecules (such as plasmids) that are capable of transmitting or of replication such nucleic acid molecules and expressing such antibodies, fusion proteins or fragments in a cell line. The nucleic acids can be single-stranded, double-stranded, may contain both single-stranded and double-stranded portions.

Consensus Sequences

In certain embodiments, the disclosure relates to antibodies or fragments comprising six CDRs having consensus sequences.

Light chain CDR is of antibodies disclosed herein:

```
CDR 1
                                     (SEQ ID NO: 11)
RASQSISSFLN,

CDR 1
                                     (SEQ ID NO: 17)
RSSQSLLHRNGYNYLD,

CDR 1
                                     (SEQ ID NO: 29)
RASQSVSSSYLA,
```

```
-continued
CDR 1
                                     (SEQ ID NO: 35)
RASQRINNLVA.
```

Consensus sequences for light chain CDR 1:

```
CDR 1
                                     (SEQ ID NO: 41)
RX¹SQXIX²,
``` wherein $X^1$ is A, S, or any amino acid and $X^2$ is S, R, or any amino acid and

```
CDR 1
                                     (SEQ ID NO: 42)
RX¹SQSX²,
``` wherein $X^1$ is A, S, or any amino acid and $X^2$ is I, L, V, or any amino acid.

Light chain CDR 2s of antibodies disclosed herein:

```
CDR 2
                                     (SEQ ID NO: 12)
AASSLQS,

CDR 2
                                     (SEQ ID NO: 36)
DASSLKS,

CDR 2
                                     (SEQ ID NO: 18)
LGSNRAS,

CDR 2
                                     (SEQ ID NO: 24)
GNSNRPS,

CDR 2
                                     (SEQ ID NO: 30)
GAFNRAT.
```

Consensus sequences for light chain CDR 2s:

```
CDR 2
                                     (SEQ ID NO: 43)
ASSLX¹S,
``` wherein $X^1$ is a Q, K, or any amino acid and

```
CDR 2
                                     (SEQ ID NO: 44)
X¹SNRX²S,
``` wherein $X^1$ is G, L, or any amino acid, and X is A, P, or any amino acid.

Light chain CDR 3s of antibodies disclosed herein:

```
CDR 3
                                     (SEQ ID NO: 13)
Q Q S Y I S P F T,

CDR 3
                                     (SEQ ID NO: 31)
Q L Y G S S P W T,

CDR 3
                                     (SEQ ID NO: 37)
Q Q Y D T D S G W T.
```

Consensus sequences for light chain CDR 3s:

CDR 3 (SEQ ID NO: 45)
QX$^1$X$^2$X$^3$X$^4$SPX$^5$T, wherein X$^1$ is Q, L, Y or any amino acid, X$^2$ is S, Y, D or any amino acid, X$^3$ is Y, G, T or any amino acid, X$^4$ is I, S, D or any amino acid, and X$^5$ is F, W or any amino acid.

Heavy Chain CDR is of antibodies disclosed herein:

CDR 1 (SEQ ID NO: 14)
FTFRSYDMH,

CDR 1 (SEQ ID NO: 20)
FAVRSNYLS,

CDR 1 (SEQ ID NO: 26)
FTFSNAWMN,

CDR 1 (SEQ ID NO: 32)
FTFSTYGMS,

CDR 1 (SEQ ID NO: 38)
FTFSKYAMI.

Consensus sequences for heavy chain CDR 1:

CDR 1 (SEQ ID NO: 46)
FX$^1$X$^2$RSX$^3$ wherein X$^1$ is T, A, or any amino acid, X$^2$ is F, V, or any amino acid, and X$^3$ is Y, N, A or any amino acid and

CDR 1 (SEQ ID NO: 47)
FTFX$^1$X$^2$YX$^3$M, wherein X$^1$ is R, S, or any amino acid, X$^2$ is S, N, T, K, or any amino acid, X3 D, Y, W, G, A, or any amino acid.

Heavy Chain CDR 2s of antibodies disclosed herein:

CDR 2 (SEQ ID NO: 15)
IGTAGDTYYPGSVKG,

CDR 2 (SEQ ID NO: 21)
LIYSGGLTAYADSVEG,

CDR 2 (SEQ ID NO: 27)
RIKSKTDGGAADYAAPVKG,

CDR 2 (SEQ ID NO: 33)
GISGSGGITYYADSVRG,

CDR 2 (SEQ ID NO: 39)
GINKSGGRTYYADSVRG.

Consensus sequences for heavy chain CDR 2:

CDR 2 (SEQ ID NO: 48)
GX$^1$X$^2$X$^3$YX$^4$X$^5$SVX$^6$G, wherein X$^1$ is D, L, A, I, R, or any amino acid, X$^2$ is T, A, or any amino acid, X$^3$ is Y, A, D, or any amino acid, X$^4$ is P, A, or any amino acid, X$^5$ is K, E, R, or any amino acid and Heavy Chain CDR 3s of antibodies disclosed herein:

CDR 3 (SEQ ID NO: 16)
VRFGDTAVDY
and

CDR 3 (SEQ ID NO: 22)
VASSAGTFYYGMDV

Consensus sequences for heavy chain CDR 3:

CDR 3 (SEQ ID NO: 49)
VX$^1$X$^2$X$^3$X$^4$X$^5$X$^6$X$^7$X$^8$Y

Wherein X$^1$ is R, A, or any amino acid, X$^2$ is F, S or any amino acid, X$^3$ is G, S, or any amino acid, X$^4$ is D, A, or any amino acid, X$^5$ is T, G, or any amino acid, X$^6$ is A, T, or any amino acid, X$^7$ is V, F, or any amino acid, X$^8$ is D, Y, or any amino acid.

In certain embodiments, the disclosure relates to antibodies or fragments comprising six CDRs having the consensus sequences. With regard to the consensus sequences any of the amino acid positions may be desirable to substitute an amino acid that corresponds to the sequence in any antibody disclosed herein.

In certain embodiments, the disclosure relates to antibodies or fragments wherein the light chain comprises
a) a light chain CDR 1 selected from

CDR 1 (SEQ ID NO: 41)
RX$^1$SQXIX$^2$, wherein X$^1$ is A, S, or any amino acid and X$^2$ is S, R, or any amino acid and

CDR 1 (SEQ ID NO: 42)
RX$^1$QSX$^2$, wherein X$^1$ is A, S, or any amino acid and X$^2$ is I, L, V, or any amino acid;
b) a light chain CDR 2 selected from:

CDR 2 (SEQ ID NO: 43)
ASSLX$^1$S, wherein X$^1$ is a Q, K, or any amino acid and

CDR 2 (SEQ ID NO: 44)
X$^1$SNRX$^2$S, wherein X$^1$ is G, L, or any amino acid, and X is A, P, or any amino acid; and c) a light chain CDR 3 comprising

QX$^1$X$^2$X$^3$X$^4$SPX$^5$T, (SEQ ID NO: 45)

wherein X$^1$ is Q, L, Y or any amino acid, X$^2$ is S, Y, D or any amino acid, X$^3$ is Y, G, T or any amino acid, X$^4$ is I, S, D or any amino acid, and X$^5$ is F, W or any amino acid.

In certain embodiments, the disclosure relates to antibodies or fragments wherein the heavy chain comprises, a) a heavy chain CDR 1 selected from

FX$^1$X$^2$RSX$^3$ (SEQ ID NO: 46)

wherein X$^1$ is T, A, or any amino acid, X$^2$ is F, V, or any amino acid, and X$^3$ is Y, N, A or any amino acid and CDR 1

FTFX$^1$X$^2$YX$^3$M, (SEQ ID NO: 47)

wherein X$^1$ is R, S, or any amino acid, X$^2$ is S, N, T, K, or any amino acid, X3 D, Y, W, G, A, or any amino acid;

b) a heavy chain CDR 2 having

GX$^1$X$^2$X$^3$YX$^4$X$^5$SVX$^6$G, (SEQ ID NO: 48)

wherein X$^1$ is D, L, A, I, R, or any amino acid, X$^2$ is T, A, or any amino acid, X$^3$ is Y, A, D, or any amino acid, X$^4$ is P, A, or any amino acid, X$^5$ is K, E, R, or any amino acid; and c) a heavy chain CDR 3 having

VX$^1$X$^2$X$^3$X$^4$X$^5$X$^6$X$^7$X$^8$Y, (SEQ ID NO: 49)

wherein X$^1$ is R, A, or any amino acid, X$^2$ is F, S or any amino acid, X$^3$ is G, S, or any amino acid, X$^4$ is D, A, or any amino acid, X$^5$ is T, G, or any amino acid, X$^6$ is A, T, or any amino acid, X$^7$ is V, F, or any amino acid, X$^8$ is D, Y, or any amino acid.

In certain embodiments, the disclosure relates to antibodies or fragments wherein the light chain comprises a CDR 1 having

CDR 1
RX$^1$SQXIX$^2$, (SEQ ID NO: 41)

wherein X$^1$ is A, S, or any amino acid and X$^2$ is S, R, or any amino acid, a CDR 2 having

CDR 2
ASSLX$^1$S, (SEQ ID NO: 43)

wherein X$^1$ is a Q, K, or any amino acid, and a

CDR 3
QX$^1$X$^2$X$^3$X$^4$SPX$^5$T, (SEQ ID NO: 45)

wherein X$^1$ is Q, L, Y or any amino acid, X$^2$ is S, Y, D or any amino acid, X$^3$ is Y, G, T or any amino acid, X$^4$ is I, S, D or any amino acid, and X$^5$ is F, W or any amino acid, and
the heavy chain comprises
a

CDR 1
FX$^1$X$^2$RSX$^3$ (SEQ ID NO: 46)

wherein X$^1$ is T, A, or any amino acid, X$^2$ is F, V, or any amino acid, and X$^3$ is Y, N, A or any amino acid,
a

CDR 2
GX$^1$X$^2$X$^3$YX$^4$X$^5$SVX$^6$G, (SEQ ID NO: 48)

wherein X$^1$ is D, L, A, I, R, or any amino acid, X$^2$ is T, A, or any amino acid, X$^3$ is Y, A, D, or any amino acid, X$^4$ is P, A, or any amino acid, X$^5$ is K, E, R, or any amino acid; and
a

CDR 3
VX$^1$X$^2$X$^3$X$^4$X$^5$X$^6$X$^7$X$^8$Y, (SEQ ID NO: 49)

wherein X$^1$ is R, A, or any amino acid, X$^2$ is F, S or any amino acid, X$^3$ is G, S, or any amino acid, X$^4$ is D, A, or any amino acid, X$^5$ is T, G, or any amino acid, X$^6$ is A, T, or any amino acid, X$^7$ is V, F, or any amino acid, X$^8$ is D, Y, or any amino acid.

Therapeutic Methods

In certain embodiments, the disclosure relates to methods of preventing or treating an Ebola virus infection comprising administering an effective amount of a pharmaceutical composition comprising an antibody or antigen binding fragment disclosed herein to a subject in need thereof. Treatment of a subject with a therapeutically or prophylactically effective amount of antibody or antibody binding fragment can include a single treatment or, preferably, can include a series of treatments. In certain embodiments, the subject is at risk of, exhibiting symptoms of, or diagnosed with an Ebola virus infection.

In certain embodiments, the antibody or antigen binding fragment is administered in combination with another or second therapeutic agent or antiviral agent. In certain embodiments, the antiviral agent(s) is abacavir, acyclovir, acyclovir, adefovir, amantadine, amprenavir, ampligen, arbidol, atazanavir, atripla, boceprevir, cidofovir, combivir, complera, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, stribild, tenofovir, tenofovir disoproxil, tenofovir alafenamide fumarate, tipranavir, trifluridine, trizivir, tromantadine, truvada, valaciclovir, valganciclovir, vicriviroc, vidarabine, viramidine, zalcitabine, zanamivir, or zidovudine, and combinations thereof.

In certain embodiments, the other or second therapeutic agent may be monoclonal antibodies (mabs) targeting the Ebola virus surface glycoprotein (GP) such as ZMAb (MAbs 2G4, 4G7, and 1H3) or MB-003 (MAbs 13C6, 6D8, and 13F6) or human chimera thereof. See Zeitlin et al., Enhanced potency of a fucose-free monoclonal antibody being developed as an Ebola virus immunoprotectant. Proc. Natl. Acad. Sci. U.S.A. 108, 20690-20694 (2011). The original murine 13F6 variable regions were deimmunized and were subsequently chimerized with human constant regions, containing an alanine at N297 of the human IgG heavy-chain constant region (h-13F6agly) to eliminate Fc glycosylation entirely. In certain embodiments, the disclosure contemplates that N297 may be substituted to any other nucleic acid such as G, A, S T, C, V, L, I, M, F, Y, P, W, D, E, H, K, or R. Other contemplated agents include interfering RNA (siRNA) or antisense oligonucleotides molecules, e.g., phosphorodiamidate morpholino oligomers (PMOs), that target Ebola mRNA.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity, the route of administration, as well as age, body weight, response, and the past medical history of the patient. Suitable regimens can be selected by one skilled in the art by considering such factors and by following, for example, dosages reported in the literature and recommended in the Physician's Desk Reference (56th Ed., 2002).

Various delivery systems are known and can be used to administer the therapeutic or prophylactic compositions, e.g., encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

Methods of administering antibodies and antigen binding fragments include, but are not limited to, parenteral administration (e.g., intradermal, intramuscular, intraperitoneal, intravenous and subcutaneous), epidural, and mucosal (e.g., intranasal and oral routes). In a specific embodiment, the antibodies or fusion proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934, 272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

In some embodiments, the antibodies or antigen binding fragments are formulated in liposomes for targeted delivery of the antibodies or fusion proteins. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 can be used to make liposomes-antibody compositions. Preferred liposomes are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces opsonization with serum components and reduces recognition by MPS. Sterically stabilized liposomes are preferably prepared using polyethylene glycol. For preparation of liposomes and sterically stabilized liposome, see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the disclosed compositions and methods can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody, e.g., F(ab'), may be conjugated to the liposomes using previously described methods, see, e.g., Martin et al., 1982, J. Biol. Chem. 257: 286-288.

The antibodies, or antigen binding fragments may also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, Stealth Liposomes, Boca Rotan: CRC Press, 233-44; Hansen et al., 1995, Biochim. Biophys. Acta, 1239: 133-144. In most preferred embodiments, immunoliposomes for use in the disclosed methods and compositions are further sterically stabilized. Preferably, the antibodies or antigen binding fragments are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phosphatidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, Biochemistry, 35: 1100-1105; Loughrey et al., 1987, Biochim. Biophys. Acta, 901: 157-160; Martin et al., 1982, J. Biol. Chem. 257: 286-288; Martin et al., 1981, Biochemistry, 20: 4429-38. Although not intending to be bound by a particular mechanism of action, immunoliposomal formulations including an antibody or fusion protein are particularly effective as therapeutic agents, since they deliver the antibody or fusion protein to the cytoplasm of the target cell, i.e., the cell comprising the receptor to which the antibody or fusion protein binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions include one or more vesicle forming lipids, an antibody or a fragment or derivative thereof or a fusion protein, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations are known to one skilled in the art and encompassed within the invention. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al., 1994, Immunomethods, 4: 259-72; Maruyama, 2000, Biol. Pharm. Bull. 23(7): 791-799; Abra et al., 2002, Journal of Liposome Research, 12(1&2): 1-3; Park, 2002, Bioscience Reports, 22(2): 267-281; Bendas et al., 2001 BioDrugs, 14(4): 215-224, J. Thomas August, ed., 1997, Gene Therapy: Advances in Pharmacology, Volume 40, Academic Press, San Diego, Calif., p. 399-435.

The antibodies and antigen binding fragments can be packaged in a hermetically sealed container, such as an ampoule or sachette, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies or fusion proteins are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies or antigen binding fragments should be stored at between 2 and 8 degrees C. in their original container and the antibodies should be administered within 12 hours, preferably within 6 hours, within 5 hours, within 3 hours, or within 1 hour after being reconstituted. In an alternative embodiment, antibodies or fusion proteins are supplied in liquid form in a hermetically sealed container indicating the quantity and concentration of the antibody, fusion protein, or conjugated molecule. Preferably, the liquid form of the antibodies or fusion proteins are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies of fusion proteins.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof, or fusion proteins may be reduced by enhancing uptake and tissue penetration of the antibodies or fusion proteins by modifications such as, for example, lipidation.

In certain embodiments, the therapeutic or prophylactic composition is a nucleic acid encoding an Ebola antibody or an antigen-binding fragment thereof. The nucleic acid can be administered in vivo to promote expression of its encoded antibody or fragment, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, the disclosed compositions include a prophylactically or therapeutically effective amount of antibody or fusion protein and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with antibody or antigen binding fragment. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more antibodies or antigen binding fragments. In another embodiment, a kit further comprises one or more other prophylactic or therapeutic agents useful for the treatment of Ebola infection, in one or more containers.

Diagnostic Methods

The Ebola antibodies and their antigen-binding fragments disclosed herein can be used for diagnostic purposes, such as to detect, diagnose, or monitor Ebola infections. The invention provides for the detection or diagnosis of infection comprising: (a) assaying a sample for Ebola or in a tissue sample of a subject using one or more antibodies (or fragments thereof) that immunospecifically bind to Ebola particles comprising the epitopes; and (b) comparing the level of the Ebola with a control level, e.g., levels in normal tissue samples, whereby an increase or decrease in the assayed level of Ebola compared to the control level is indicative of the infection. Such antibodies and fragments are preferably employed in immunoassays, such as the enzyme linked immunosorbent assay (ELISA), the radioimmunoassay (RIA) and fluorescence-activated cell sorting (FACS).

One embodiment relates to the use of such antibodies and fragments, and particularly such antibodies and fragments that bind to human Ebola, as reagents for detection of Ebola in a sample or at a site of in vivo dormancy. Thus, the antibodies and fragments of the present invention have utility in the detection and diagnosis of an infection in a human. In one embodiment, such diagnosis comprises: a) administering to a subject (for example, parenterally, subcutaneously, or intraperitoneally) an effective amount of a labeled antibody or antigen-binding fragment that immunospecifically binds to Ebola particles; b) waiting for a time interval following the administration for permitting the labeled molecule to preferentially concentrate at sites in the subject where Ebola is (and for unbound labeled molecule to be cleared to background level); c) determining background level; and d) detecting the labeled antibody in the subject, such that detection of labeled antibody above the background level indicates that the subject has the infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of an infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the disclosed diagnostic methods include, but are not limited to, computed tomography (CT), whole body scan such as position emission tomography (PET), magnetic resonance imaging (MRI), and sonography.

In a specific embodiment, the antibody or antigen binding fragment is labeled with a radioisotope and is detected in the patient using a radiation responsive surgical instrument (Thurston et al., U.S. Pat. No. 5,441,050). In another embodiment, the antibody or antigen binding fragment is labeled with a fluorescent compound and is detected in the patient using a fluorescence responsive scanning instrument. In another embodiment, the antibody or antigen binding fragment is labeled with a positron emitting metal and is detected in the patient using positron emission-tomography. In yet another embodiment, the antibody or antigen binding fragment is labeled with a paramagnetic label and is detected in a patient using magnetic resonance imaging (MRI).

Examples

Disclosed herein are monoclonal antibodies specific for the glycoprotein of Ebola virus that can be used as a neutralizing antibody, prophylactically treating those who have yet to develop symptoms, or for treating patients diagnosed with Ebola virus disease. In order to develop these antibodies, circulating B cells and plasma cells were collected from the blood of patients who had recovered from Ebola infection. The three cell populations (bulk activated B cells, bulk plasmablasts, and Ebola glycoprotein-binding B cells), were sorted so that virus-specific antibodies could be isolated. Antibody heavy and light chain variable region segments were then amplified by PCR from single sorted cells. These gene segments were cloned into expression vectors and the antibodies were produced and evaluated for their ability to neutralize Ebola virus infectivity in vitro. Over 1000 individual sequences were determined in order to identify 200 Ebola glycoprotein-binding antibodies. These were screened to determine their ability to neutralize Ebola virus in vitro.

Through in vitro studies, it was identified that several of the monoclonal antibodies that were generated have high affinity compared to the antibody component of ZMapp, monoclonal antibody for treating Ebola virus disease. Tables below shows data for certain antibodies.

| antibody | ELISA EC50 | specificity | GP constuct used for ELISA |
|---|---|---|---|
| 5.1.10B3 | 5.2 ng/ml (35 pM) | New epitope | Delta mucin |
| 2.1.1D05 | 5.1 ng/ml (34 pM) | New epitope | Delta mucin |
| 5.6.1A2 | 12 ng/ml (80 pM) | Chalice base? | Delta mucin |
| 13C6 | 40 ng/ml (270 pM) | Glycan cap | Delta mucin |
| 2G4 | 100 ng/ml (670 pM) | Chalice base | Delta mucin |
| 1H3 | 400 ng/ml (2.7 nM) | Glycan cap | Delta mucin |
| KZ52 | 40 ng/ml (270 pM) | Chalice base | Delta mucin |
| 13F6 | 4 ng/ml (2.7 pM) | Mucin domain | Full length GP |

| antibody | PRNT50 (ug/ml) for Ebola Zaire (Kikwit strain) |
|---|---|
| 5.6.c2618 (ATK-13) | 0.0061 |
| 9.6.3A06 | 0.0488 |
| 5.1.13G03 | 0.0978 |
| 5.6.1A02 | 0.195 |
| 2.1.7G07 | 1.57 |
| 2.1.1D07 | 6.25 |
| 5.1.10B03 | 3.13 |
| 2.1.1D05 | 3.13 |
| 5.1.7D03 | 1.57 |
| 9.6.1A09 | 0.78125 |
| 9.6.3D06 | 1.57 |
| 2.10.1E06 | 0.78125 |

Neutralizing Antibodies and their Properties are as Follows:

Antibody, 5.6.1A2, neutralizes Ebola virus in vitro with a PRNT50 value of below 100 ng/ml—this is comparable or superior to all previously described antibodies. The mouse protection data for 5.1.10B3 and 5.6.1A2 showed 80-90% protection when the antibodies were given one day prior to infection of the animals with Ebola virus, which is superior to the protection observed in previous studies. PRNT is a plaque reduction neutralization test standard for detecting and measuring antibodies that neutralize viruses; number represents the concentration of serum necessary to reduce the number of infected host cell plaques that form.

5.1.10B3—antibody source: bulk plasmablasts from EVD5 1 month; PRNT*80 of 3 ug/ml and PRNT50 of 25 ug/ml; protected 8/10 mice. Escape mutations map to GP base.

5.6.1A2—antibody source: GP binding cells from EVD5 6 months; PRNT80 of 98 ng/ml and PRNT50 not yet determined but less than 98 ng/ml; protected 9/10 mice. Escape mutations map to fusion loop.

2.1.1D05—antibody source: GP binding cells from EVD2 1 month; in vitro neutralization potency not yet determined; protected 3/10 mice. Escape mutations map to glycan cap.

2.1.1D07—antibody source: GP binding cells from EVD2 1 month.

9.6.3D6—antibody source: GP binding cells from EVD9 6 months; in vitro neutralization.

Strain-relevant binding affinity:
Ebola Zaire (Mayinga) GP—all
Bundibugyo GP—5.6.1A2, 9.6.3D6
Reston GP—2.1.1D05, 2.1.1D07, 5.6.1A2
Sudan GP—2.1.1D07

TABLE

Data for Select Antibodies

| mAb name | epitope location | 50% plaque reduction neutralization titer (PRNT50) for Ebola Zaire | 50% plaque reduction neutralization titer (PRNT50) for Ebola Sudan | % of mice protected from 100 p.f.u. Ebola challenge when antibody given 1 day prior to infection |
|---|---|---|---|---|
| 2.1.1B02 | mucin residues 478-490 | non-neutralizing | | 100% protection |
| 5.24.1C11 | fusion loop | <0.36 µg/ml | <0.36 µg/ml | |
| 9.20.1C03 | inner chalice bowl | <0.36 µg/ml | <0.36 µg/ml | |
| 5.24.1B03 Binds all filoviruses | glycan cap | non-neutralizing | | |

TABLE-continued

Data for Select Antibodies

| mAb name | epitope location | 50% plaque reduction neutralization titer (PRNT50) for Ebola Zaire | 50% plaque reduction neutralization titer (PRNT50) for Ebola Sudan | % of mice protected from 100 p.f.u. Ebola challenge when antibody given 1 day prior to infection |
|---|---|---|---|---|
| 9.20.1D09 | chalice base | <0.36 µg/ml | 0.78 µg/ml | |
| 5.24.2A03 Binds all filoviruses | glycan cap | non-neutralizing | | |
| 9.20.1A02 | inner chalice bowl | <0.36 µg/ml | non-neutralizing | |
| 5.24.2C05 | chalice base | <0.36 µg/ml | 6.25 µg/ml | |
| 5.24.2B07 | inner chalice bowl | 1.56 µg/ml | 12.5 µg/ml | |

Methods for Production of the Antibodies Utilized Protocols Provided in the Following References.

Wrammert et al. report using immunoglobulin variable regions isolated from sorted single ASCs to produce human monoclonal antibodies (mAbs) that bound with high affinity. Nature. 2008 May 29; 453(7195): 667-671. Smith et al. report a protocol for the production of antigen-specific human monoclonal antibodies (hmAbs) wherein antibody-secreting cells (ASCs) are isolated from whole blood collected after vaccination and sorted by flow cytometry into single cell plates. The antibody genes of the ASCs are then amplified by RT-PCR and nested PCR, cloned into expression vectors and transfected into a human cell line. See FIG. 1.

The complete sequence for a cloning vector for generating a chimeric antibody heavy chain with a human immunoglobulin G1 (AbVec-hIgG1) is found in GenBank ACCESSION FJ475055 which comprises a CMV promotor, murine IgG1 signal peptide, cloning site, Cgamma-1 (IgG1) constant region derived from Homo sapiens (SEQ ID NO: 66), followed by beta-lactamase which confers resistance to ampicillin.

In certain embodiments, antibodies or antigen binding fragments disclosed herein comprise a heavy chain constant region of with a sequence below or with a sequence having at least 80, 85, 90, 95, 98, 99%, or more identity or similarity. Heavy chain constant region sequence:

(SEQ ID NO: 66)
RSTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In certain embodiments, antibody or antigen binding fragment comprises the N297A mutation:

(SEQ ID NO: 67)
RSTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

In certain embodiments, antibody or antigen binding fragment comprises the triple mutation M252Y/S254T/T256E mutation:

(SEQ ID NO: 68)
RSTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLYITREPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

The invention claimed is:

1. A non-naturally occurring chimeric antibody or antigen binding fragment comprising six complementarity determining regions (CDRs) of antibody 5.24.1C11,
   wherein the CDRs comprise the three light chain CDRs, wherein light chain CDR 1 comprises the amino acid sequence of

QSLLHSNGYNY; (SEQ ID NO: 134)

light chain CDR2 comprises the amino acid sequence of

LGSS; (SEQ ID NO: 135)

light chain CDR3 comprises the amino acid sequence of

MQGLQTPLT; (SEQ ID NO: 136)

and,
   wherein the CDRs comprise the three heavy chain CDRs, wherein heavy chain CDR 1 comprises the amino acid sequence of

GYTFSSYNIH; (SEQ ID NO: 138)

CDR 2 comprises the amino acid sequence of

PYGRSTT, (SEQ ID NO: 139)

and CDR 3 comprises the amino acid sequence of

GRLYSGAPYGLDV, (SEQ ID NO: 140)

and
   wherein the antibody or antigen binding fragment thereof binds to an epitope expressed in an Ebola virus particle.

2. The antibody or antigen binding fragment of claim 1 comprising a human constant domain from an immunoglobulin constant region (Fc) having one or more of the following mutations: G236A, S239D, A330L, I332E, S267E, L328F, P238D, H268F, S324T, S228P, G236R, L328R, L234A, L235A, M252Y, S254T, T256E, M428L, N434S, A330L, N297A, and N297Q wherein the Fc mutations are in reference to positions in amino acid sequence (SEQ ID NO: 50)
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDE, wherein the N-terminal amino acid serine (S) is position 119.

3. The antibody or antigen fragment of claim 1 comprising at least one amino acid substitution in the heavy chain constant region that is not present in naturally occurring antibodies comprising the six CDRs.

4. The antibody of claim 1, wherein the heavy chain comprises a sequence in a constant region that is different from any sequences present in naturally occurring antibodies for which the light chain variable region comprise the three light chain CDRs and the heavy chain variable region comprise the three heavy chain CDRs.

5. The antibody or antigen binding fragment thereof of claim 1, wherein the epitope expressed on an Ebola virus particle is arrayed on a surface, expressed on the surface of a cell, or expressed at an endogenous or transfected concentration, and the antibody or antigen binding fragment is bound to the epitope.

6. A nucleic acid molecule encoding an antibody or antigen binding fragment of claim 1.

7. An expression vector comprising a nucleic acid molecule encoding the antibody or the antigen binding fragment of claim 1.

8. A recombinant protein expression system comprising isolated host cells expressing the nucleic acid molecule of the expression vector of claim 7, wherein the isolated host cells are prokaryotic cells or eukaryotic cells.

9. A pharmaceutical composition comprising the antibody or antigen binding fragment thereof of claim 1, and a physiologically acceptable carrier or excipient.

10. A method of detection Ebola virus infection, comprising: (a) assaying the expression of Ebola virus epitope in cells or in a tissue sample of a subject using the antibody or antigen binding fragment thereof of claim 1 and (b) comparing the level of the Ebola virus epitope with a control level, wherein an increase in the assayed level of Ebola virus compared to the control level is indicative of the infection.

11. A method of treating an Ebola virus infection comprising administering an effective amount of a pharmaceutical composition of claim 8 to a subject in need thereof.

12. A non-naturally occurring chimeric antibody or antigen binding fragment comprising six complementarity determining regions (CDRs) of antibody 9.20.1C03, wherein the CDRs comprise the three light chain CDRs, wherein light chain CDR 1 comprises the amino acid sequence of (SEQ ID NO: 142)
HSVLYSSNNKDF;

CDR2 comprises the amino acid sequence of (SEQ ID NO: 143)
WAST;

and comprises the amino acid sequence of CDR3

(SEQ ID NO: 144)
QQYFSSPIT;

and
wherein the CDRs comprise the three heavy chain CDRs, wherein heavy chain CDR 1 comprises the amino acid sequence of (SEQ ID NO: 146)
GGTFSSYT;

and CDR 2 comprises the amino acid sequence of (SEQ ID NO: 147)
IIPSFGVG;

and CDR 3 comprises the amino acid sequence of (SEQ ID NO: 148)
AILGTFNWKSGGNYFGP, and
wherein the antibody or antigen binding fragment thereof binds to an epitope expressed in an Ebola virus particle.

13. The antibody or antigen binding fragment of claim 12 comprising a human constant domain from an immunoglobulin constant region (Fc) having one or more of the following mutations: G236A, S239D, A330L, I332E, S267E, L328F, P238D, H268F, S324T, S228P, G236R, L328R, L234A, L235A, M252Y, S254T, T256E, M428L, N434S, A330L, N297A, and N297Q wherein the Fc mutations are in reference to positions in amino acid sequence (SEQ ID NO: 50)
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDE, wherein the N-terminal amino acid serine (S) is position 119.

14. The antibody or antigen fragment of claim 12 comprising at least one amino acid substitution in the heavy chain constant region that is not present in naturally occurring antibodies comprising the six CDRs.

15. The antibody of claim 12, wherein the heavy chain comprises a sequence in a constant region that is different from any sequences present in naturally occurring antibodies for which the light chain variable region comprise the three light chain CDRs and the heavy chain variable region comprise the three heavy chain CDRs.

16. The antibody or antigen binding fragment thereof of claim 12, wherein the epitope expressed on an Ebola virus particle is arrayed on a surface, expressed on the surface of a cell, or expressed at an endogenous or transfected concentration, and the antibody or antigen binding fragment is bound to the epitope.

17. A nucleic acid molecule encoding an antibody or antigen binding fragment of claim 12.

18. An expression vector comprising a nucleic acid molecule encoding the antibody or the antigen binding fragment of claim 12.

19. A recombinant protein expression system comprising isolated host cells expressing the nucleic acid molecule of the expression vector of claim 18, wherein the isolated host cells are prokaryotic cells or eukaryotic cells.

20. A pharmaceutical composition comprising the antibody or antigen binding fragment thereof of claim 12, and a physiologically acceptable carrier or excipient.

* * * * *

SEQUENCE LISTING

<160> NUMBER OF SEQ ID NOS: 218

<210> SEQ ID NO 1
<211> LENGTH: 107
<212> TYPE: PRT
<213> ORGANISM: Artificial
<220> FEATURE:
<223> OTHER INFORMATION: Synthetic

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe

```
                20                  25                  30
Leu Asn Trp His Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ser Tyr Ile Ser Pro Phe
                85                  90                  95

Thr Phe Gly Pro Gly Thr Lys Val Asp Ile Lys
            100                 105
```

<210> SEQ ID NO 2
<211> LENGTH: 118
<212> TYPE: PRT
<213> ORGANISM: Artificial
<220> FEATURE:
<223> OTHER INFORMATION: Synthetic

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Val Arg Phe Gly Asp Thr Ala Val Asp Tyr Trp Gly Gln Gly Thr
            100                 105                 110

Leu Val Thr Val Ser Ser
        115
```

<210> SEQ ID NO 3
<211> LENGTH: 113
<212> TYPE: PRT
<213> ORGANISM: Artificial
<220> FEATURE:
<223> OTHER INFORMATION: Synthetic

<400> SEQUENCE: 3

```
Asp Ile Val Met Thr Gln Ser Pro Arg Ser Leu Ser Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Leu Gln Thr Pro Ser Trp Thr Phe Gly Gln Gly Thr Lys Val Glu Ile
                100                 105                 110

Lys

<210> SEQ ID NO 4
<211> LENGTH: 122
<212> TYPE: PRT
<213> ORGANISM: Artificial
<220> FEATURE:
<223> OTHER INFORMATION: Synthetic

<400> SEQUENCE: 4

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ala Val Arg Ser Asn
            20                  25                  30

Tyr Leu Ser Trp Val Arg Gln Ala Pro Gly Lys Gly Leu Glu Trp Val
        35                  40                  45

Ser Leu Ile Tyr Ser Gly Gly Leu Thr Ala Tyr Ala Asp Ser Val Glu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Val Glu Asp Thr Ala Leu Tyr Tyr Cys Ala
                85                  90                  95

Arg Val Ala Ser Ser Ala Gly Thr Phe Tyr Tyr Gly Met Asp Val Trp
            100                 105                 110

Gly Gln Gly Thr Thr Val Thr Val Ser Ser
        115                 120

<210> SEQ ID NO 5
<211> LENGTH: 112
<212> TYPE: PRT
<213> ORGANISM: Artificial
<220> FEATURE:
<223> OTHER INFORMATION: Synthetic

<400> SEQUENCE: 5

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val Tyr Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Phe Asp Ser Ser
                85                  90                  95

Leu Arg Asp Ser Trp Val Phe Gly Gly Gly Thr Lys Leu Thr Val Leu
            100                 105                 110

<210> SEQ ID NO 6
<211> LENGTH: 120
<212> TYPE: PRT
<213> ORGANISM: Artificial
<220> FEATURE:
<223> OTHER INFORMATION: Synthetic

<400> SEQUENCE: 6

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Ala Ala Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Phe Cys Thr Thr Val Tyr Arg Tyr Asn Tyr Asp Ser Val Trp Gly Gln
            100                 105                 110

Gly Thr Leu Val Thr Val Ser Ser
            115                 120
```

```
<210> SEQ ID NO 7
<211> LENGTH: 108
<212> TYPE: PRT
<213> ORGANISM: Artificial
<220> FEATURE:
<223> OTHER INFORMATION: Synthetic

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Tyr Gly Ser Ser Pro
                85                  90                  95

Trp Thr Phe Gly Gln Gly Thr Lys Val Glu Ile Lys
            100                 105
```

```
<210> SEQ ID NO 8
<211> LENGTH: 120
<212> TYPE: PRT
<213> ORGANISM: Artificial
<220> FEATURE:
<223> OTHER INFORMATION: Synthetic

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Ile Thr Tyr Tyr Ala Asp Ser Val
    50                  55                  60

Arg Gly Arg Phe Thr Ile Ser Arg Asp Asn Ser Lys Asn Thr Leu Tyr
```

```
                65                  70                  75                  80
Leu Arg Met Asn Ser Leu Arg Ala Glu Asp Thr Ala Val Tyr Tyr Cys
                85                  90                  95

Ala Lys Val Gly Glu Tyr Tyr Asp Phe Trp Ser Gly Tyr Ser Pro Phe
            100                 105                 110

Glu Tyr Trp Gly Gln Gly Thr Leu
        115                 120
```

<210> SEQ ID NO 9
<211> LENGTH: 108
<212> TYPE: PRT
<213> ORGANISM: Artificial
<220> FEATURE:
<223> OTHER INFORMATION: Synthetic

<400> SEQUENCE: 9

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Arg Ile Asn Asn Leu
            20                  25                  30

Val Ala Trp Tyr Gln Gln Lys Pro Gly Lys Ala Pro Lys Val Met Ile
        35                  40                  45

Tyr Asp Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Asp Thr Asp Ser Gly
                85                  90                  95

Trp Thr Phe Gly Gln Gly Thr Lys Val Glu Ile Lys
            100                 105
```

<210> SEQ ID NO 10
<211> LENGTH: 129
<212> TYPE: PRT
<213> ORGANISM: Artificial
<220> FEATURE:
<223> OTHER INFORMATION: Synthetic

<400> SEQUENCE: 10

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ala Met Ile Trp Val Arg Gln Ala Pro Gly Lys Gly Leu Gln Trp Val
        35                  40                  45

Ala Gly Ile Asn Lys Ser Gly Arg Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Lys Ser Leu Arg Ala Asp Thr Ala Met Tyr Tyr Cys
                85                  90                  95

Ala Lys Glu Gly Ser Pro Leu Ser Asp Val Leu Leu Val Ala Ala Pro
            100                 105                 110

Phe Gly Trp Phe Asp Pro Trp Gly Gln Gly Thr Leu Val Thr Val Ser
        115                 120                 125

Ser
```

```
<210> SEQ ID NO 11
<211> LENGTH: 11
<212> TYPE: PRT
<213> ORGANISM: Artificial
<220> FEATURE:
<223> OTHER INFORMATION: Synthetic

<400> SEQUENCE: 11

Arg Ala Ser Gln Ser Ile Ser Ser Phe Leu Asn
1               5                   10

<210> SEQ ID NO 12
<211> LENGTH: 7
<212> TYPE: PRT
<213> ORGANISM: Artificial
<220> FEATURE:
<223> OTHER INFORMATION: Synthetic

<400> SEQUENCE: 12

Ala Ala Ser Ser Leu Gln Ser
1               5

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

Gln Gln Ser Tyr Ile Ser Pro Phe Thr
1               5

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Phe Thr Phe Arg Ser Tyr Asp Met His
1               5

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

Ile Gly Thr Ala Gly Asp Thr Tyr Tyr Pro
1               5                   10

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Val Arg Phe Gly Asp Thr Ala Val Asp Tyr
1               5                   10

<210> SEQ ID NO 17
```

```
<211> LENGTH: 16
<212> TYPE: PRT
<213> ORGANISM: Artificial
<220> FEATURE:
<223> OTHER INFORMATION: Synthetic

<400> SEQUENCE: 17

Arg Ser Ser Gln Ser Leu Leu His Arg Asn Gly Tyr Asn Tyr Leu Asp
1               5                   10                  15

<210> SEQ ID NO 18
<211> LENGTH: 7
<212> TYPE: PRT
<213> ORGANISM: Artificial
<220> FEATURE:
<223> OTHER INFORMATION: Synthetic

<400> SEQUENCE: 18

Leu Gly Ser Asn Arg Ala Ser
1               5

<210> SEQ ID NO 19
<211> LENGTH: 10
<212> TYPE: PRT
<213> ORGANISM: Artificial
<220> FEATURE:
<223> OTHER INFORMATION: Synthetic

<400> SEQUENCE: 19

Met Gln Ala Leu Gln Thr Pro Ser Trp Thr
1               5                   10

<210> SEQ ID NO 20
<211> LENGTH: 9
<212> TYPE: PRT
<213> ORGANISM: Artificial
<220> FEATURE:
<223> OTHER INFORMATION: Synthetic

<400> SEQUENCE: 20

Phe Ala Val Arg Ser Asn Tyr Leu Ser
1               5

<210> SEQ ID NO 21
<211> LENGTH: 16
<212> TYPE: PRT
<213> ORGANISM: Artificial
<220> FEATURE:
<223> OTHER INFORMATION: Synthetic

<400> SEQUENCE: 21

Leu Ile Tyr Ser Gly Gly Leu Thr Ala Tyr Ala Asp Ser Val Glu Gly
1               5                   10                  15

<210> SEQ ID NO 22
<211> LENGTH: 14
<212> TYPE: PRT
<213> ORGANISM: Artificial
<220> FEATURE:
<223> OTHER INFORMATION: Synthetic

<400> SEQUENCE: 22

Val Ala Ser Ser Ala Gly Thr Phe Tyr Tyr Gly Met Asp Val
1               5                   10

<210> SEQ ID NO 23
<211> LENGTH: 14
```

```
<212> TYPE: PRT
<213> ORGANISM: Artificial
<220> FEATURE:
<223> OTHER INFORMATION: Synthetic

<400> SEQUENCE: 23

Thr Gly Ser Ser Ser Asn Ile Gly Ala Gly Tyr Asp Val Tyr
1               5                   10

<210> SEQ ID NO 24
<211> LENGTH: 7
<212> TYPE: PRT
<213> ORGANISM: Artificial
<220> FEATURE:
<223> OTHER INFORMATION: Synthetic

<400> SEQUENCE: 24

Gly Asn Ser Asn Arg Pro Ser
1               5

<210> SEQ ID NO 25
<211> LENGTH: 12
<212> TYPE: PRT
<213> ORGANISM: Artificial
<220> FEATURE:
<223> OTHER INFORMATION: Synthetic

<400> SEQUENCE: 25

Gln Ser Phe Asp Ser Ser Leu Arg Asp Ser Trp Val
1               5                   10

<210> SEQ ID NO 26
<211> LENGTH: 9
<212> TYPE: PRT
<213> ORGANISM: Artificial
<220> FEATURE:
<223> OTHER INFORMATION: Synthetic

<400> SEQUENCE: 26

Phe Thr Phe Ser Asn Ala Trp Met Asn
1               5

<210> SEQ ID NO 27
<211> LENGTH: 19
<212> TYPE: PRT
<213> ORGANISM: Artificial
<220> FEATURE:
<223> OTHER INFORMATION: Synthetic

<400> SEQUENCE: 27

Arg Ile Lys Ser Lys Thr Asp Gly Gly Ala Ala Asp Tyr Ala Ala Pro
1               5                   10                  15

Val Lys Gly

<210> SEQ ID NO 28
<211> LENGTH: 9
<212> TYPE: PRT
<213> ORGANISM: Artificial
<220> FEATURE:
<223> OTHER INFORMATION: Synthetic

<400> SEQUENCE: 28

Val Tyr Arg Tyr Asn Tyr Asp Ser Val
1               5

<210> SEQ ID NO 29
```

```
<211> LENGTH: 12
<212> TYPE: PRT
<213> ORGANISM: Artificial
<220> FEATURE:
<223> OTHER INFORMATION: Synthetic

<400> SEQUENCE: 29

Arg Ala Ser Gln Ser Val Ser Ser Ser Tyr Leu Ala
1               5                   10

<210> SEQ ID NO 30
<211> LENGTH: 7
<212> TYPE: PRT
<213> ORGANISM: Artificial
<220> FEATURE:
<223> OTHER INFORMATION: Synthetic

<400> SEQUENCE: 30

Gly Ala Phe Asn Arg Ala Thr
1               5

<210> SEQ ID NO 31
<211> LENGTH: 9
<212> TYPE: PRT
<213> ORGANISM: Artificial
<220> FEATURE:
<223> OTHER INFORMATION: Synthetic

<400> SEQUENCE: 31

Gln Leu Tyr Gly Ser Ser Pro Trp Thr
1               5

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Phe Thr Phe Ser Thr Tyr Gly Met Ser
1               5

<210> SEQ ID NO 33
<211> LENGTH: 17
<212> TYPE: PRT
<213> ORGANISM: Artificial
<220> FEATURE:
<223> OTHER INFORMATION: Synthetic

<400> SEQUENCE: 33

Gly Ile Ser Gly Ser Gly Gly Ile Thr Tyr Tyr Ala Asp Ser Val Arg
1               5                   10                  15

Gly

<210> SEQ ID NO 34
<211> LENGTH: 16
<212> TYPE: PRT
<213> ORGANISM: Artificial
<220> FEATURE:
<223> OTHER INFORMATION: Synthetic

<400> SEQUENCE: 34

Val Gly Glu Tyr Tyr Asp Phe Trp Ser Gly Tyr Ser Pro Phe Glu Tyr
1               5                   10                  15
```

```
<210> SEQ ID NO 35
<211> LENGTH: 11
<212> TYPE: PRT
<213> ORGANISM: Artificial
<220> FEATURE:
<223> OTHER INFORMATION: Synthetic

<400> SEQUENCE: 35

Arg Ala Ser Gln Arg Ile Asn Asn Leu Val Ala
1               5                   10

<210> SEQ ID NO 36
<211> LENGTH: 7
<212> TYPE: PRT
<213> ORGANISM: Artificial
<220> FEATURE:
<223> OTHER INFORMATION: Synthetic

<400> SEQUENCE: 36

Asp Ala Ser Ser Leu Lys Ser
1               5

<210> SEQ ID NO 37
<211> LENGTH: 10
<212> TYPE: PRT
<213> ORGANISM: Artificial
<220> FEATURE:
<223> OTHER INFORMATION: Synthetic

<400> SEQUENCE: 37

Gln Gln Tyr Asp Thr Asp Ser Gly Trp Thr
1               5                   10

<210> SEQ ID NO 38
<211> LENGTH: 9
<212> TYPE: PRT
<213> ORGANISM: Artificial
<220> FEATURE:
<223> OTHER INFORMATION: Synthetic

<400> SEQUENCE: 38

Phe Thr Phe Ser Lys Tyr Ala Met Ile
1               5

<210> SEQ ID NO 39
<211> LENGTH: 17
<212> TYPE: PRT
<213> ORGANISM: Artificial
<220> FEATURE:
<223> OTHER INFORMATION: Synthetic

<400> SEQUENCE: 39

Gly Ile Asn Lys Ser Gly Gly Arg Thr Tyr Tyr Ala Asp Ser Val Arg
1               5                   10                  15

Gly

<210> SEQ ID NO 40
<211> LENGTH: 20
<212> TYPE: PRT
<213> ORGANISM: Artificial
<220> FEATURE:
<223> OTHER INFORMATION: Synthetic

<400> SEQUENCE: 40

Glu Gly Ser Pro Leu Ser Asp Val Leu Leu Val Ala Ala Pro Phe Gly
1               5                   10                  15
```

```
Trp Phe Asp Pro
            20

<210> SEQ ID NO 41
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(7)
<223> OTHER INFORMATION: X is any amino acid

<400> SEQUENCE: 41

Arg Xaa Ser Gln Xaa Ile Xaa
1               5

<210> SEQ ID NO 42
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(6)
<223> OTHER INFORMATION: X is any amino acid

<400> SEQUENCE: 42

Arg Xaa Ser Gln Ser Xaa
1               5

<210> SEQ ID NO 43
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(6)
<223> OTHER INFORMATION: X is any amino acid

<400> SEQUENCE: 43

Ala Ser Ser Leu Xaa Ser
1               5

<210> SEQ ID NO 44
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(6)
<223> OTHER INFORMATION: X is any amino acid

<400> SEQUENCE: 44

Xaa Ser Asn Arg Xaa Ser
1               5

<210> SEQ ID NO 45
<211> LENGTH: 9
<212> TYPE: PRT
<213> ORGANISM: Artificial
<220> FEATURE:
<223> OTHER INFORMATION: Synthetic
<220> FEATURE:
```

```
<221> NAME/KEY: X
<222> LOCATION: (1)..(9)
<223> OTHER INFORMATION: X is any amino acid

<400> SEQUENCE: 45

Gln Xaa Xaa Xaa Xaa Ser Pro Xaa Thr
1               5

<210> SEQ ID NO 46
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(6)
<223> OTHER INFORMATION: X is any amino acid

<400> SEQUENCE: 46

Phe Xaa Xaa Arg Ser Xaa
1               5

<210> SEQ ID NO 47
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(8)
<223> OTHER INFORMATION: X is any amino acid

<400> SEQUENCE: 47

Phe Thr Phe Xaa Xaa Tyr Xaa Met
1               5

<210> SEQ ID NO 48
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(11)
<223> OTHER INFORMATION: X is any amino acid

<400> SEQUENCE: 48

Gly Xaa Xaa Xaa Tyr Xaa Xaa Ser Val Xaa Gly
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(10)
<223> OTHER INFORMATION: X is any amino acid

<400> SEQUENCE: 49

Val Xaa Xaa Xaa Xaa Xaa Xaa Xaa Xaa Tyr
1               5                   10

<210> SEQ ID NO 50
```

<211> LENGTH: 328
<212> TYPE: PRT
<213> ORGANISM: Homo sapiens

<400> SEQUENCE: 50

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 51
<211> LENGTH: 321
<212> TYPE: DNA
<213> ORGANISM: Artificial
<220> FEATURE:
<223> OTHER INFORMATION: Synthetic

<400> SEQUENCE: 51

```
gacatccaga tgacccagtc tccatcctcc ctgtctgcat ctgtaggaga cagagtcacc    60
atcacttgcc gggcaagtca gagcattagc agcttttaa attggcatca gcagaaacca    120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caatttacta ctgtcaacag agttacattt ccccattcac tttcggccct   300
gggaccaaag tggatatcaa a                                             321
```

<210> SEQ ID NO 52
<211> LENGTH: 356
<212> TYPE: DNA
<213> ORGANISM: Artificial
<220> FEATURE:
<223> OTHER INFORMATION: Synthetic

<400> SEQUENCE: 52

```
gaggtgcagc tggtggagtc tgggggaggc ttggtacagc ctgggggtc cctgagactc     60 tcctgtgcag cctctggatt caccttcaga agctacgaca tgcactgggt ccgccaagct   120
acaggaaaag gtctggagtg ggtctcagct attggtactg ctggtgacac atactatcca   180
ggctccgtga agggccgatt caccatctcc agagaaaatg ccaagaactc cttgtatctt   240
caaatgaaca gcctgagagc cgaggacacg gccgtgtatt actgtgcaag agtccgtttc   300
ggggatacag ccgttgacta ctggggccag ggaaccctgg tcaccgtctc ctcagc       356
```

<210> SEQ ID NO 53
<211> LENGTH: 339
<212> TYPE: DNA
<213> ORGANISM: Artificial
<220> FEATURE:
<223> OTHER INFORMATION: Synthetic

<400> SEQUENCE: 53

```
gatattgtga tgactcagtc tccacgctcc ctgtccgtca cccctggaga gccggcctcc    60
atctcctgca ggtctagtca gagcctcctg catagaaatg gatataacta tttggattgg   120
tatctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgaaga tgttggggtt tattactgca tgcaagctct acaaactccc   300
tcgtggacgt tcggccaagg gaccaaggtg gaaatcaaa                          339
```

<210> SEQ ID NO 54
<211> LENGTH: 368
<212> TYPE: DNA
<213> ORGANISM: Artificial
<220> FEATURE:
<223> OTHER INFORMATION: Synthetic

<400> SEQUENCE: 54

```
gaggtgcagc tggtggagtc aggaggaggc ttgatccagc ctgggggtc cctgagactc     60 tcctgtgcag cctctggttt cgccgtcagg agcaactact tgagctgggt ccgccaggct   120
cctgggaagg gctggagtg gtctcactt atttatagtg gtggtctcac agcctacgca    180
gactccgtgg agggccggtt caccatctcc agagacaatt ctaagaacac actatatctt   240
caaatgaaca gcctgagagt cgaggacacg gccctatatt actgtgcgag agtcgcatca   300
tcggctggaa ccttctacta cggtatggac gtctggggcc aagggaccac ggtcaccgtc   360
tcctcagc                                                            368
```

<210> SEQ ID NO 55
<211> LENGTH: 336
<212> TYPE: DNA
<213> ORGANISM: Artificial
<220> FEATURE:
<223> OTHER INFORMATION: Synthetic

<400> SEQUENCE: 55

```
cagtctgtgc tgacgcagcc gccctcagtg tctggggccc cagggcagag ggtcaccatc      60
tcctgcactg ggagcagttc aacatcggg gcaggttatg atgtatactg gtaccagcag      120
cttccaggaa cagcccccaa actcctcatc tatggtaaca gcaatcggcc ctcaggggtc      180
cctgaccgat tctctggctc caagtctggc acctcagcct ccctggccat cactgggctc      240
caggctgagg atgaggctga ttactactgc cagtcctttg acagcagcct gagagattct      300
tgggtgttcg gcgggggac caagctgacc gtccta                                  336
```

<210> SEQ ID NO 56
<211> LENGTH: 362
<212> TYPE: DNA
<213> ORGANISM: Artificial
<220> FEATURE:
<223> OTHER INFORMATION: Synthetic

<400> SEQUENCE: 56

```
gaggtgcagc tggtggagtc tgggggaggc ttggtaaaac ctggggggtc ccttagactc      60
tcctgtgcag cctctggatt cactttcagt aacgcctgga tgaactgggt ccgccaggct      120
ccagggaagg ggctggagtg ggttggccgt attaagagca aaactgatgg tggggctgca      180
gactacgctg cacccgtgaa gggcagattc accatctcaa gagatgattc aaaaaacacg      240
ctgtatctgc aaatgaacag cctgaaaacc gaggacacag ccgtgtattt ctgtaccaca      300
gtctacagat acaactatga ttccgtctgg ggccagggaa ccctggtcac cgtctcctca      360
gc                                                                       362
```

<210> SEQ ID NO 57
<211> LENGTH: 324
<212> TYPE: DNA
<213> ORGANISM: Artificial
<220> FEATURE:
<223> OTHER INFORMATION: Synthetic

<400> SEQUENCE: 57

```
gaaattgtgt tgacgcagtc tccaggcacc ctgtctttgt ctccagggga aagagccacc      60
ctctcctgca gggccagtca gagtgttagc agcagctact tagcctggta ccagcagaaa      120
cctggccagg ctcccaggct cctcatctat ggtgcattta cagggccac tggcatccca      180 gacaggttca gtggcagtgg gtctgggaca gacttcactc tcaccatcag cagactggag      240
cctgaagatt ttgcagtgta ttactgtcag ctgtatggta gctcaccgtg gacgttcggc      300
caagggacca aggtggaaat caaa                                              324
```

<210> SEQ ID NO 58
<211> LENGTH: 377
<212> TYPE: DNA
<213> ORGANISM: Artificial
<220> FEATURE:
<223> OTHER INFORMATION: Synthetic

<400> SEQUENCE: 58

-continued

```
gaggtgcagc tgttggagtc tggggggaggc ttggtacagc ctggggggtc cctgagactc    60
tcctgtgcag cctctggatt cacctttagc acctatggca tgagctgggt ccgccaggct   120
ccagggaagg ggctggagtg ggtctcaggt attagtggta gtggtggtat cacatactac   180
gcagactccg tgaggggccg gttcaccatc tccagagaca attccaagaa cacgctgtat   240
ctgcgaatga acagcctgag agccgaggac acggccgtat attactgtgc gaaagtgggg   300
gagtattacg attttggag tggttattcc cccttgaat actggggcca gggaaccctg   360
gtcaccgtct cctcagc                                                  377
```

<210> SEQ ID NO 59
<211> LENGTH: 324
<212> TYPE: DNA
<213> ORGANISM: Artificial
<220> FEATURE:
<223> OTHER INFORMATION: Synthetic

<400> SEQUENCE: 59

```
gacatccaga tgacccagtc tccttccacc ctgtctgcat ctgtaggaga cagagtcacc    60
atcacttgcc gggccagtca gaggattaat aatttggtgg cctggtatca gcagaaacca   120
gggaaagccc ctaaggtcat gatctatgat gcctccagtt tgaaaagtgg ggtcccatca   180
aggttcagcg gcagtggatc tgggacagaa ttcactctca ccatcagcag cctgcaacct   240
gatgattttg caacttattt ctgccaacag tatgatactg attcggggtg gacgttcggc   300
caagggacca aggtggaaat caaa                                          324
```

<210> SEQ ID NO 60
<211> LENGTH: 389
<212> TYPE: DNA
<213> ORGANISM: Artificial
<220> FEATURE:
<223> OTHER INFORMATION: Synthetic

<400> SEQUENCE: 60

```
gaggtgcagc tgttggagtc tggggggaggc ctggtacagc cggggggggtc cctgagactc    60 tcctgtgccg cctctggatt cacctttagc aaatatgcca tgatctgggt ccgccaggcc   120
ccagggaagg ggctgcagtg ggtcgcaggt attaataaga gtggtggcag acatactac   180 gcagactccg tgaggggccg gttcaccatc tccagagaca attccaagaa tacgctgtac   240
ctgcaaatga aaagcctgag agccgacgac acggccatgt attactgtgc gaaagaggga   300 tccccttat cagatgtttt actggtagca gctccatttg ggtggttcga tccctggggc   360
cagggaaccc tggtcaccgt ctcctcagc                                     389
```

<210> SEQ ID NO 61
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(16)
<223> OTHER INFORMATION: X is any amino acid

<400> SEQUENCE: 61

Tyr Xaa Xaa Leu Xaa Xaa Xaa Xaa Xaa Xaa Xaa Xaa Tyr Xaa Xaa Leu
1               5                   10                  15

<210> SEQ ID NO 62

<211> LENGTH: 150
<212> TYPE: PRT
<213> ORGANISM: Artificial
<220> FEATURE:
<223> OTHER INFORMATION: Synthetic

<400> SEQUENCE: 62

Ala Gln Leu Pro Ile Thr Glu Ala Gln Ser Phe Gly Leu Leu Asp Pro
1               5                   10                  15

Lys Leu Cys Tyr Leu Leu Asp Gly Ile Leu Phe Ile Tyr Gly Val Ile
            20                  25                  30

Leu Thr Ala Leu Phe Leu Arg Val Lys Phe Ser Arg Ser Ala Asp Ala
        35                  40                  45

Pro Ala Tyr Gln Gln Gly Gln Asn Gln Leu Tyr Asn Glu Leu Asn Leu
    50                  55                  60

Gly Arg Arg Glu Glu Tyr Asp Val Leu Asp Lys Arg Arg Gly Arg Asp
65                  70                  75                  80

Pro Glu Met Gly Gly Lys Pro Arg Arg Lys Asn Pro Gln Glu Gly Leu
                85                  90                  95

Tyr Asn Glu Leu Gln Lys Asp Lys Met Ala Glu Ala Tyr Ser Glu Ile
            100                 105                 110

Gly Met Lys Gly Glu Arg Arg Arg Gly Lys Gly His Asp Gly Leu Tyr
        115                 120                 125

Gln Gly Leu Ser Thr Ala Thr Lys Asp Thr Tyr Asp Ala Leu His Met
    130                 135                 140

Gln Ala Leu Pro Pro Arg
145                 150

<210> SEQ ID NO 63
<211> LENGTH: 151
<212> TYPE: PRT
<213> ORGANISM: Artificial
<220> FEATURE:
<223> OTHER INFORMATION: Synthetic

<400> SEQUENCE: 63

Ala Gln Leu Pro Ile Thr Glu Ala Gln Ser Phe Gly Leu Leu Asp Pro
1               5                   10                  15

Lys Leu Cys Tyr Leu Leu Asp Gly Ile Leu Phe Ile Tyr Gly Val Ile
            20                  25                  30

Leu Thr Ala Leu Phe Leu Arg Val Lys Phe Ser Arg Ser Ala Asp Ala
        35                  40                  45

Pro Ala Tyr Gln Gln Gly Gln Asn Gln Leu Tyr Asn Glu Leu Asn Leu
    50                  55                  60

Gly Arg Arg Glu Glu Tyr Asp Val Leu Asp Lys Arg Arg Gly Arg Asp
65                  70                  75                  80

Pro Glu Met Gly Gly Lys Pro Gln Arg Arg Lys Asn Pro Gln Glu Gly
                85                  90                  95

Leu Tyr Asn Glu Leu Gln Lys Asp Lys Met Ala Glu Ala Tyr Ser Glu
            100                 105                 110

Ile Gly Met Lys Gly Glu Arg Arg Arg Gly Lys Gly His Asp Gly Leu
        115                 120                 125

Tyr Gln Gly Leu Ser Thr Ala Thr Lys Asp Thr Tyr Asp Ala Leu His
    130                 135                 140

Met Gln Ala Leu Pro Pro Arg
145                 150

<210> SEQ ID NO 64
<211> LENGTH: 150
<212> TYPE: PRT
<213> ORGANISM: Artificial
<220> FEATURE:
<223> OTHER INFORMATION: Synthetic

<400> SEQUENCE: 64

```
Ala Gln Leu Pro Ile Thr Glu Ala Gln Ser Phe Gly Leu Leu Asp Pro
1               5                   10                  15
Lys Leu Cys Tyr Leu Leu Asp Gly Ile Leu Phe Ile Tyr Gly Val Ile
                20                  25                  30
Leu Thr Ala Leu Phe Leu Arg Val Lys Phe Ser Arg Ser Ala Glu Pro
            35                  40                  45
Pro Ala Tyr Gln Gln Gly Gln Asn Gln Leu Tyr Asn Glu Leu Asn Leu
        50                  55                  60
Gly Arg Arg Glu Glu Tyr Asp Val Leu Asp Lys Arg Arg Gly Arg Asp
65                  70                  75                  80
Pro Glu Met Gly Gly Lys Pro Arg Arg Lys Asn Pro Gln Glu Gly Leu
                85                  90                  95
Tyr Asn Glu Leu Gln Lys Asp Lys Met Ala Glu Ala Tyr Ser Glu Ile
                100                 105                 110
Gly Met Lys Gly Glu Arg Arg Arg Gly Lys Gly His Asp Gly Leu Tyr
            115                 120                 125
Gln Gly Leu Ser Thr Ala Thr Lys Asp Thr Tyr Asp Ala Leu His Met
        130                 135                 140
Gln Ala Leu Pro Pro Arg
145                 150
```

<210> SEQ ID NO 65
<211> LENGTH: 62
<212> TYPE: PRT
<213> ORGANISM: Artificial
<220> FEATURE:
<223> OTHER INFORMATION: Synthetic

<400> SEQUENCE: 65

```
Glu Pro Gln Leu Cys Tyr Ile Leu Asp Ala Ile Leu Phe Leu Tyr Gly
1               5                   10                  15
Ile Val Leu Thr Leu Leu Tyr Cys Arg Leu Lys Ile Gln Val Arg Lys
                20                  25                  30
Ala Ala Ile Thr Ser Tyr Glu Lys Ser Asp Gly Val Tyr Thr Gly Leu
            35                  40                  45
Ser Thr Arg Asn Gln Glu Thr Tyr Glu Thr Leu Lys His Glu
        50                  55                  60
```

<210> SEQ ID NO 66
<211> LENGTH: 330
<212> TYPE: PRT
<213> ORGANISM: Artificial
<220> FEATURE:
<223> OTHER INFORMATION: Synthetic

<400> SEQUENCE: 66

```
Arg Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 330
<212> TYPE: PRT
<213> ORGANISM: Artificial
<220> FEATURE:
<223> OTHER INFORMATION: Synthetic

<400> SEQUENCE: 67

Arg Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 330
<212> TYPE: PRT
<213> ORGANISM: Artificial
<220> FEATURE:
<223> OTHER INFORMATION: Synthetic

<400> SEQUENCE: 68

Arg Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Gly Gly Pro Ser Val Phe Leu Phe Pro Pro
            115                 120                 125

Lys Pro Lys Asp Thr Leu Tyr Ile Thr Arg Glu Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 69
<211> LENGTH: 108
<212> TYPE: PRT
<213> ORGANISM: Artificial
<220> FEATURE:
<223> OTHER INFORMATION: Synthetic

<400> SEQUENCE: 69

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Phe Thr Phe Gly Pro Gly Thr Lys Val Asp Ile Lys
            100                 105

<210> SEQ ID NO 70
<211> LENGTH: 7
<212> TYPE: PRT
<213> ORGANISM: Artificial
```

```
<220> FEATURE:
<223> OTHER INFORMATION: Synthetic

<400> SEQUENCE: 70

Gln Ser Val Ser Ser Ser Tyr
1               5

<210> SEQ ID NO 71
<211> LENGTH: 7
<212> TYPE: PRT
<213> ORGANISM: Artificial
<220> FEATURE:
<223> OTHER INFORMATION: Synthetic

<400> SEQUENCE: 71

Gly Ala Phe Asn Arg Ala Thr
1               5

<210> SEQ ID NO 72
<211> LENGTH: 9
<212> TYPE: PRT
<213> ORGANISM: Artificial
<220> FEATURE:
<223> OTHER INFORMATION: Synthetic

<400> SEQUENCE: 72

Gln Gln Tyr Gly Arg Ser Pro Phe Thr
1               5

<210> SEQ ID NO 73
<211> LENGTH: 125
<212> TYPE: PRT
<213> ORGANISM: Artificial
<220> FEATURE:
<223> OTHER INFORMATION: Synthetic

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Ala Met Ser Trp Val Arg Gln Ala Pro Gly Lys Gly Leu Glu Trp Val
        35                  40                  45

Ser Ala Ile Thr Gly Ser Gly Tyr Ser Thr Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Val Gly Glu Tyr Tyr Asp Phe Trp Ser Gly Tyr Ser Pro Phe
            100                 105                 110

Asp Ser Trp Gly Gln Gly Thr Leu Val Thr Val Ser Ser
        115                 120                 125

<210> SEQ ID NO 74
<211> LENGTH: 8
<212> TYPE: PRT
<213> ORGANISM: Artificial
<220> FEATURE:
<223> OTHER INFORMATION: Synthetic

<400> SEQUENCE: 74

Gly Phe Ala Phe Ser Thr Tyr Ala
```

```
1               5

<210> SEQ ID NO 75
<211> LENGTH: 8
<212> TYPE: PRT
<213> ORGANISM: Artificial
<220> FEATURE:
<223> OTHER INFORMATION: Synthetic

<400> SEQUENCE: 75

Ile Thr Gly Ser Gly Tyr Ser Thr
1               5

<210> SEQ ID NO 76
<211> LENGTH: 18
<212> TYPE: PRT
<213> ORGANISM: Artificial
<220> FEATURE:
<223> OTHER INFORMATION: Synthetic

<400> SEQUENCE: 76

Ala Lys Val Gly Glu Tyr Tyr Asp Phe Trp Ser Gly Tyr Ser Pro Phe
1               5                   10                  15

Asp Ser

<210> SEQ ID NO 77
<211> LENGTH: 112
<212> TYPE: PRT
<213> ORGANISM: Artificial
<220> FEATURE:
<223> OTHER INFORMATION: Synthetic

<400> SEQUENCE: 77

Asp Ile Val Met Thr Gln Thr Pro Leu Ser Ser Ala Val Thr Leu Gly
1               5                   10                  15

Gln Pro Ala Ser Ile Ser Cys Arg Ser Ser Gln Arg Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Val Ser Leu Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Thr Gln Phe Pro Leu Thr Phe Gly Gly Gly Thr Lys Val Glu Ile Lys
            100                 105                 110

<210> SEQ ID NO 78
<211> LENGTH: 11
<212> TYPE: PRT
<213> ORGANISM: Artificial
<220> FEATURE:
<223> OTHER INFORMATION: Synthetic

<400> SEQUENCE: 78

Gln Arg Leu Val His Ser Asp Gly Asn Thr Tyr
1               5                   10

<210> SEQ ID NO 79
<211> LENGTH: 7
<212> TYPE: PRT
<213> ORGANISM: Artificial
```

```
<220> FEATURE:
<223> OTHER INFORMATION: Synthetic

<400> SEQUENCE: 79

Lys Val Ser Leu Arg Phe Ser
1               5

<210> SEQ ID NO 80
<211> LENGTH: 9
<212> TYPE: PRT
<213> ORGANISM: Artificial
<220> FEATURE:
<223> OTHER INFORMATION: Synthetic

<400> SEQUENCE: 80

Met Gln Ala Thr Gln Phe Pro Leu Thr
1               5

<210> SEQ ID NO 81
<211> LENGTH: 115
<212> TYPE: PRT
<213> ORGANISM: Artificial
<220> FEATURE:
<223> OTHER INFORMATION: Synthetic

<400> SEQUENCE: 81

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Asn Glu Tyr
            20                  25                  30

Met Met Asn Trp Val Arg Gln Pro Pro Gly Lys Gly Leu Glu Trp Val
        35                  40                  45

Ser Ser Ile Ser Gly Thr Ser Thr Tyr Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Asp Asp Thr Ala Met Tyr Tyr Cys
                85                  90                  95

Ala Arg Gly Ser Thr Gly Gly Tyr Trp Gly Gln Gly Thr Leu Ile Thr
            100                 105                 110

Val Ser Ser
    115

<210> SEQ ID NO 82
<211> LENGTH: 8
<212> TYPE: PRT
<213> ORGANISM: Artificial
<220> FEATURE:
<223> OTHER INFORMATION: Synthetic

<400> SEQUENCE: 82

Gly Phe Thr Phe Asn Glu Tyr Met
1               5

<210> SEQ ID NO 83
<211> LENGTH: 8
<212> TYPE: PRT
<213> ORGANISM: Artificial
<220> FEATURE:
<223> OTHER INFORMATION: Synthetic

<400> SEQUENCE: 83

Ile Ser Gly Thr Ser Thr Tyr Ile
```

```
1               5
```

<210> SEQ ID NO 84
<211> LENGTH: 6
<212> TYPE: PRT
<213> ORGANISM: Artificial
<220> FEATURE:
<223> OTHER INFORMATION: Synthetic

<400> SEQUENCE: 84

```
Gly Ser Thr Gly Gly Tyr
1               5
```

<210> SEQ ID NO 85
<211> LENGTH: 107
<212> TYPE: PRT
<213> ORGANISM: Artificial
<220> FEATURE:
<223> OTHER INFORMATION: Synthetic

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ser Ala Phe Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105
```

<210> SEQ ID NO 86
<211> LENGTH: 8
<212> TYPE: PRT
<213> ORGANISM: Artificial
<220> FEATURE:
<223> OTHER INFORMATION: Synthetic

<400> SEQUENCE: 86

```
Gln Ser Ile Ser Ser Tyr Leu Asn
1               5
```

<210> SEQ ID NO 87
<211> LENGTH: 7
<212> TYPE: PRT
<213> ORGANISM: Artificial
<220> FEATURE:
<223> OTHER INFORMATION: Synthetic

<400> SEQUENCE: 87

```
Ser Ala Phe Ser Leu Gln Asn
1               5
```

<210> SEQ ID NO 88
<211> LENGTH: 9
<212> TYPE: PRT
<213> ORGANISM: Artificial
<220> FEATURE:
<223> OTHER INFORMATION: Synthetic

<400> SEQUENCE: 88

Gln Gln Ser Tyr Ser Thr Pro Arg Thr
1               5

<210> SEQ ID NO 89
<211> LENGTH: 116
<212> TYPE: PRT
<213> ORGANISM: Artificial
<220> FEATURE:
<223> OTHER INFORMATION: Synthetic

<400> SEQUENCE: 89

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Thr
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Leu Asp Lys Ser Lys Asp Gln Phe Ser
65                  70                  75                  80

Leu Lys Leu Ser Ser Val Thr Ala Ala Asp Thr Ala Val Tyr Tyr Cys
                85                  90                  95

Ala Tyr Ser Asn Thr Trp Thr Gly Gly Trp Gly Gln Gly Thr Leu Val
            100                 105                 110

Thr Val Ser Ser
        115

<210> SEQ ID NO 90
<211> LENGTH: 10
<212> TYPE: PRT
<213> ORGANISM: Artificial
<220> FEATURE:
<223> OTHER INFORMATION: Synthetic

<400> SEQUENCE: 90

Gly Ser Ile Ser Ser Thr Asn Trp Trp Ser
1               5                   10

<210> SEQ ID NO 91
<211> LENGTH: 6
<212> TYPE: PRT
<213> ORGANISM: Artificial
<220> FEATURE:
<223> OTHER INFORMATION: Synthetic

<400> SEQUENCE: 91

His Ser Gly Ser Thr Asn
1               5

<210> SEQ ID NO 92
<211> LENGTH: 7
<212> TYPE: PRT
<213> ORGANISM: Artificial
<220> FEATURE:
<223> OTHER INFORMATION: Synthetic

<400> SEQUENCE: 92

Ser Asn Thr Trp Thr Gly Gly
1               5

<210> SEQ ID NO 93
<211> LENGTH: 107
<212> TYPE: PRT
<213> ORGANISM: Artificial
<220> FEATURE:
<223> OTHER INFORMATION: Synthetic

<400> SEQUENCE: 93

```
Glu Val Val Leu Thr Gln Ser Pro Val Thr Leu Ser Leu Ser Pro Gly
1               5                   10                  15
Glu Arg Ala Thr Leu Ser Cys Arg Ala Ser Gln Ser Val Ser Gly Tyr
            20                  25                  30
Leu Ala Trp Tyr Gln Gln Lys Pro Gly Gln Val Pro Arg Leu Leu Ile
        35                  40                  45
Tyr Asp Thr Ser Asn Arg Ala Thr Gly Ile Pro Ala Arg Phe Ser Gly
    50                  55                  60
Ser Gly Ser Gly Thr Asp Phe Thr Leu Thr Ile Ser Thr Ile Glu Pro
65                  70                  75                  80
Glu Asp Phe Ala Val Tyr Tyr Cys Gln Gln Arg Ser Lys Trp Gly Val
                85                  90                  95
Thr Phe Gly Gly Gly Thr Lys Val Asp Ile Lys
            100                 105
```

<210> SEQ ID NO 94
<211> LENGTH: 8
<212> TYPE: PRT
<213> ORGANISM: Artificial
<220> FEATURE:
<223> OTHER INFORMATION: Synthetic

<400> SEQUENCE: 94

```
Gln Ser Val Ser Gly Tyr Leu Ala
1               5
```

<210> SEQ ID NO 95
<211> LENGTH: 7
<212> TYPE: PRT
<213> ORGANISM: Artificial
<220> FEATURE:
<223> OTHER INFORMATION: Synthetic

<400> SEQUENCE: 95

```
Asp Thr Ser Asn Arg Ala Thr
1               5
```

<210> SEQ ID NO 96
<211> LENGTH: 9
<212> TYPE: PRT
<213> ORGANISM: Artificial
<220> FEATURE:
<223> OTHER INFORMATION: Synthetic

<400> SEQUENCE: 96

```
Gln Gln Arg Ser Lys Trp Gly Val Thr
1               5
```

<210> SEQ ID NO 97
<211> LENGTH: 124
<212> TYPE: PRT
<213> ORGANISM: Artificial
<220> FEATURE:
<223> OTHER INFORMATION: Synthetic

<400> SEQUENCE: 97

```
Gln Val Gln Leu Val Gln Ser Gly Ala Glu Val Lys Pro Gly Ala
1               5                   10                  15

Ser Val Asn Leu Ser Cys Lys Gly Ser Gly Tyr Ser Phe Arg Thr Tyr
            20                  25                  30

Tyr Ile His Trp Val Arg Gln Ala Pro Gly Gln Gly Leu Glu Trp Met
            35                  40                  45

Gly Ile Ile Asn Ser Ser Gly Gly Thr Thr Tyr Ala Gln Lys Phe
50                  55                  60

Gln Gly Arg Val Thr Met Thr Arg Asp Thr Ser Ser Thr Val Tyr
65                  70                  75                  80

Met Glu Leu Arg Ser Leu Lys Tyr Glu Asp Thr Ala Met Tyr Tyr Cys
                85                  90                  95

Ala Arg Asp Arg Phe Pro Thr Val Ser Gly Glu Pro Phe Ala Met Asp
            100                 105                 110

Val Trp Gly Gln Gly Thr Thr Val Thr Val Ser Ser
        115                 120
```

<210> SEQ ID NO 98
<211> LENGTH: 10
<212> TYPE: PRT
<213> ORGANISM: Artificial
<220> FEATURE:
<223> OTHER INFORMATION: Synthetic

<400> SEQUENCE: 98

```
Gly Tyr Ser Phe Arg Thr Tyr Tyr Ile His
1               5                   10
```

<210> SEQ ID NO 99
<211> LENGTH: 10
<212> TYPE: PRT
<213> ORGANISM: Artificial
<220> FEATURE:
<223> OTHER INFORMATION: Synthetic

<400> SEQUENCE: 99

```
Ile Asn Ser Ser Gly Gly Thr Thr Tyr
1               5
```

<210> SEQ ID NO 100
<211> LENGTH: 15
<212> TYPE: PRT
<213> ORGANISM: Artificial
<220> FEATURE:
<223> OTHER INFORMATION: Synthetic

<400> SEQUENCE: 100

```
Asp Arg Phe Pro Thr Val Ser Gly Glu Pro Phe Ala Met Asp Val
1               5                   10                  15
```

<210> SEQ ID NO 101
<211> LENGTH: 109
<212> TYPE: PRT
<213> ORGANISM: Artificial
<220> FEATURE:
<223> OTHER INFORMATION: Synthetic

<400> SEQUENCE: 101

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Asn
            20                  25                  30
```

```
Tyr Leu Ala Trp Tyr Gln Gln Lys Pro Gly Gln Ala Pro Arg Val Leu
            35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ala Ser Pro
                 85                  90                  95

Pro Tyr Ser Phe Gly Gln Gly Thr Lys Val Glu Ile Lys
            100                 105

<210> SEQ ID NO 102
<211> LENGTH: 9
<212> TYPE: PRT
<213> ORGANISM: Artificial
<220> FEATURE:
<223> OTHER INFORMATION: Synthetic

<400> SEQUENCE: 102

Gln Ser Val Thr Ser Asn Tyr Leu Ala
1               5

<210> SEQ ID NO 103
<211> LENGTH: 7
<212> TYPE: PRT
<213> ORGANISM: Artificial
<220> FEATURE:
<223> OTHER INFORMATION: Synthetic

<400> SEQUENCE: 103

Gly Ala Ser Ser Arg Ala Thr
1               5

<210> SEQ ID NO 104
<211> LENGTH: 10
<212> TYPE: PRT
<213> ORGANISM: Artificial
<220> FEATURE:
<223> OTHER INFORMATION: Synthetic

<400> SEQUENCE: 104

Gln Gln Phe Gly Ala Ser Pro Pro Tyr Ser
1               5                   10

<210> SEQ ID NO 105
<211> LENGTH: 127
<212> TYPE: PRT
<213> ORGANISM: Artificial
<220> FEATURE:
<223> OTHER INFORMATION: Synthetic

<400> SEQUENCE: 105

Glu Val Gln Leu Val Glu Ser Gly Gly Gly Leu Ile Gln Pro Gly Gly
1               5                   10                  15

Ser Leu Arg Leu Ser Cys Thr Ala Ser Gly Phe Thr Phe Ser Lys Phe
             20                  25                  30

Ala Met Ser Trp Val Arg Gln Ala Pro Gly Arg Gly Leu Glu Trp Ile
            35                  40                  45

Ser Tyr Ile Ser Gly Gly Ser Lys Thr Lys Tyr Tyr Ala Asp Ser Val
     50                  55                  60

Arg Gly Arg Phe Thr Ile Ser Arg Asp Asn Ala Lys Gly Ser Leu Phe
 65                  70                  75                  80
```

```
Leu Gln Met Asn Ser Leu Arg Ala Glu Asp Thr Ala Ile Tyr Phe Cys
                85                  90                  95

Ala Lys Lys Gly Trp Gln Ser Thr Phe Leu Gly Met Asp Tyr Phe Tyr
            100                 105                 110

Gly Met Asp Val Trp Gly Lys Gly Thr Thr Val Thr Val Ser Ser
        115                 120                 125
```

<210> SEQ ID NO 106
<211> LENGTH: 10
<212> TYPE: PRT
<213> ORGANISM: Artificial
<220> FEATURE:
<223> OTHER INFORMATION: Synthetic

<400> SEQUENCE: 106

```
Gly Phe Thr Phe Ser Lys Phe Ala Met Ser
1               5                   10
```

<210> SEQ ID NO 107
<211> LENGTH: 9
<212> TYPE: PRT
<213> ORGANISM: Artificial
<220> FEATURE:
<223> OTHER INFORMATION: Synthetic

<400> SEQUENCE: 107

```
Ile Ser Gly Gly Ser Lys Thr Lys Tyr
1               5
```

<210> SEQ ID NO 108
<211> LENGTH: 20
<212> TYPE: PRT
<213> ORGANISM: Artificial
<220> FEATURE:
<223> OTHER INFORMATION: Synthetic

<400> SEQUENCE: 108

```
Ala Lys Lys Gly Trp Gln Ser Thr Phe Leu Gly Met Asp Tyr Phe Tyr
1               5                   10                  15

Gly Met Asp Val
            20
```

<210> SEQ ID NO 109
<211> LENGTH: 113
<212> TYPE: PRT
<213> ORGANISM: Artificial
<220> FEATURE:
<223> OTHER INFORMATION: Synthetic

<400> SEQUENCE: 109

```
Asp Ile Val Met Thr Gln Ser Pro Asp Ser Leu Ala Val Ser Leu Gly
1               5                   10                  15

Glu Arg Ala Ser Ile Asn Cys Lys Ser Ser Gln Ser Val Leu Ser Ser
            20                  25                  30

Ser Asn Thr Lys Asn Tyr Leu Ala Trp Tyr Gln His Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95
```

Tyr Tyr Gly Ala Pro Tyr Thr Phe Gly Gln Gly Thr Lys Val Glu Ile
            100                 105                 110

Lys

<210> SEQ ID NO 110
<211> LENGTH: 12
<212> TYPE: PRT
<213> ORGANISM: Artificial
<220> FEATURE:
<223> OTHER INFORMATION: Synthetic

<400> SEQUENCE: 110

Gln Ser Val Leu Ser Ser Ser Asn Thr Lys Asn Tyr
1               5                   10

<210> SEQ ID NO 111
<211> LENGTH: 7
<212> TYPE: PRT
<213> ORGANISM: Artificial
<220> FEATURE:
<223> OTHER INFORMATION: Synthetic

<400> SEQUENCE: 111

Trp Ala Ser Thr Arg Glu Ser
1               5

<210> SEQ ID NO 112
<211> LENGTH: 9
<212> TYPE: PRT
<213> ORGANISM: Artificial
<220> FEATURE:
<223> OTHER INFORMATION: Synthetic

<400> SEQUENCE: 112

Gln Gln Tyr Tyr Gly Ala Pro Tyr Thr
1               5

<210> SEQ ID NO 113
<211> LENGTH: 118
<212> TYPE: PRT
<213> ORGANISM: Artificial
<220> FEATURE:
<223> OTHER INFORMATION: Synthetic

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Asp Met Asp Trp Phe Arg Gln Ser Thr Gly Lys Gly Leu Glu Trp Val
        35                  40                  45

Ser Ala Ile Gly Ser Ala Gly Asp Thr Tyr Tyr Thr Asp Ser Val Lys
    50                  55                  60

Gly Arg Phe Thr Ile Ser Arg Glu Asn Gly Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Arg Phe Gly Asp Asn Val Phe Asp Leu Trp Gly Arg Gly Thr
            100                 105                 110

Leu Val Thr Val Ser Ser
        115

```
<210> SEQ ID NO 114
<211> LENGTH: 9
<212> TYPE: PRT
<213> ORGANISM: Artificial
<220> FEATURE:
<223> OTHER INFORMATION: Synthetic

<400> SEQUENCE: 114

Phe Thr Phe Arg Ser Tyr Asp Met Asp
1               5

<210> SEQ ID NO 115
<211> LENGTH: 7
<212> TYPE: PRT
<213> ORGANISM: Artificial
<220> FEATURE:
<223> OTHER INFORMATION: Synthetic

<400> SEQUENCE: 115

Ile Gly Ser Ala Gly Asp Thr
1               5

<210> SEQ ID NO 116
<211> LENGTH: 10
<212> TYPE: PRT
<213> ORGANISM: Artificial
<220> FEATURE:
<223> OTHER INFORMATION: Synthetic

<400> SEQUENCE: 116

Ala Arg Phe Gly Asp Asn Val Phe Asp Leu
1               5                   10

<210> SEQ ID NO 117
<211> LENGTH: 108
<212> TYPE: PRT
<213> ORGANISM: Artificial
<220> FEATURE:
<223> OTHER INFORMATION: Synthetic

<400> SEQUENCE: 117

Glu Ile Val Leu Thr Gln Ser Pro Gly Thr Leu Ser Leu Ser Pro Gly
1               5                   10                  15

Glu Arg Ala Ala Leu Ser Cys Arg Ala Ser Gln Ser Val Ser Gly Asn
            20                  25                  30

Tyr Phe Ala Trp Tyr Gln Gln Lys Ser Gly Gln Ala Pro Arg Leu Leu
        35                  40                  45

Ile Ser Ala Ala Ser Ser Arg Ala Thr Gly Val Pro Asp Arg Phe Ser
    50                  55                  60

Ala Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 118
<211> LENGTH: 8
<212> TYPE: PRT
<213> ORGANISM: Artificial
<220> FEATURE:
<223> OTHER INFORMATION: Synthetic

<400> SEQUENCE: 118
```

```
Ser Val Ser Gly Asn Tyr Phe Ala
1               5
```

<210> SEQ ID NO 119
<211> LENGTH: 7
<212> TYPE: PRT
<213> ORGANISM: Artificial
<220> FEATURE:
<223> OTHER INFORMATION: Synthetic

<400> SEQUENCE: 119

```
Ala Ala Ser Ser Arg Ala Thr
1               5
```

<210> SEQ ID NO 120
<211> LENGTH: 9
<212> TYPE: PRT
<213> ORGANISM: Artificial
<220> FEATURE:
<223> OTHER INFORMATION: Synthetic

<400> SEQUENCE: 120

```
Gln Gln Tyr Gly Ser Ser Pro Leu Thr
1               5
```

<210> SEQ ID NO 121
<211> LENGTH: 118
<212> TYPE: PRT
<213> ORGANISM: Artificial
<220> FEATURE:
<223> OTHER INFORMATION: Synthetic

<400> SEQUENCE: 121

```
Glu Val Gln Leu Val Gln Ser Gly Gly Gly Leu Ala Gln Pro Gly Gly
1               5                   10                  15

Ser Leu Arg Leu Ser Cys Ala Ala Ser Gly Phe Thr Phe Arg Ser Tyr
            20                  25                  30

Asp Met His Trp Val Arg Gln Val Thr Gly Lys Gly Leu Glu Trp Val
        35                  40                  45

Ser Ala Ile Gly Thr Ala Gly Asp Thr Tyr Tyr Thr Gly Ser Val Lys
    50                  55                  60

Gly Arg Phe Thr Ile Ser Arg Glu Asn Asp Lys Ser Ser Leu Tyr Leu
65                  70                  75                  80

Gln Met Ser Ser Leu Arg Gly Glu Asp Thr Ala Val Tyr Tyr Cys Ala
                85                  90                  95

Arg Ala Ala Phe Gly Ser His Tyr Phe Asp Tyr Trp Gly Gln Gly Thr
            100                 105                 110

Leu Val Thr Val Ser Ser
        115
```

<210> SEQ ID NO 122
<211> LENGTH: 9
<212> TYPE: PRT
<213> ORGANISM: Artificial
<220> FEATURE:
<223> OTHER INFORMATION: Synthetic

<400> SEQUENCE: 122

```
Phe Thr Phe Arg Ser Tyr Asp Met His
1               5
```

<210> SEQ ID NO 123

```
<211> LENGTH: 10
<212> TYPE: PRT
<213> ORGANISM: Artificial
<220> FEATURE:
<223> OTHER INFORMATION: Synthetic

<400> SEQUENCE: 123

Ile Gly Thr Ala Gly Asp Thr Tyr Tyr Thr
1               5                   10

<210> SEQ ID NO 124
<211> LENGTH: 10
<212> TYPE: PRT
<213> ORGANISM: Artificial
<220> FEATURE:
<223> OTHER INFORMATION: Synthetic

<400> SEQUENCE: 124

Ala Ala Phe Gly Ser His Tyr Phe Asp Tyr
1               5                   10

<210> SEQ ID NO 125
<211> LENGTH: 108
<212> TYPE: PRT
<213> ORGANISM: Artificial
<220> FEATURE:
<223> OTHER INFORMATION: Synthetic

<400> SEQUENCE: 125

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Pro Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ser Asp Ser Ser Gly Thr Tyr
                85                  90                  95

Val Val Phe Gly Gly Gly Thr Lys Leu Thr Val Leu
            100                 105

<210> SEQ ID NO 126
<211> LENGTH: 6
<212> TYPE: PRT
<213> ORGANISM: Artificial
<220> FEATURE:
<223> OTHER INFORMATION: Synthetic

<400> SEQUENCE: 126

Ala Leu Pro Lys Gln Tyr
1               5

<210> SEQ ID NO 127
<211> LENGTH: 4
<212> TYPE: PRT
<213> ORGANISM: Artificial
<220> FEATURE:
<223> OTHER INFORMATION: Synthetic

<400> SEQUENCE: 127

Lys Asp Ser Glu
```

<210> SEQ ID NO 128
<211> LENGTH: 11
<212> TYPE: PRT
<213> ORGANISM: Artificial
<220> FEATURE:
<223> OTHER INFORMATION: Synthetic

<400> SEQUENCE: 128

Gln Ser Ser Asp Ser Ser Gly Thr Tyr Val Val
1               5                   10

<210> SEQ ID NO 129
<211> LENGTH: 120
<212> TYPE: PRT
<213> ORGANISM: Artificial
<220> FEATURE:
<223> OTHER INFORMATION: Synthetic

<400> SEQUENCE: 129

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Asp Ser Ser Gly Tyr Asp Ala Phe Asp Ile Trp Gly Gln
            100                 105                 110

Gly Thr Met Val Thr Val Ser Ser
        115                 120

<210> SEQ ID NO 130
<211> LENGTH: 8
<212> TYPE: PRT
<213> ORGANISM: Artificial
<220> FEATURE:
<223> OTHER INFORMATION: Synthetic

<400> SEQUENCE: 130

Gly Tyr Thr Phe Thr Ser Tyr Tyr
1               5

<210> SEQ ID NO 131
<211> LENGTH: 8
<212> TYPE: PRT
<213> ORGANISM: Artificial
<220> FEATURE:
<223> OTHER INFORMATION: Synthetic

<400> SEQUENCE: 131

Ile Asn Pro Ser Gly Gly Ser Thr
1               5

<210> SEQ ID NO 132
<211> LENGTH: 13
<212> TYPE: PRT

```
<213> ORGANISM: Artificial
<220> FEATURE:
<223> OTHER INFORMATION: Synthetic

<400> SEQUENCE: 132

Ala Arg His Asp Ser Ser Gly Tyr Asp Ala Phe Asp Ile
1               5                   10

<210> SEQ ID NO 133
<211> LENGTH: 112
<212> TYPE: PRT
<213> ORGANISM: Artificial
<220> FEATURE:
<223> OTHER INFORMATION: Synthetic

<400> SEQUENCE: 133

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Val Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Ile Tyr Tyr Cys Met Gln Gly
                85                  90                  95

Leu Gln Thr Pro Leu Thr Phe Gly Gly Gly Thr Lys Val Glu Ile Lys
            100                 105                 110

<210> SEQ ID NO 134
<211> LENGTH: 11
<212> TYPE: PRT
<213> ORGANISM: Artificial
<220> FEATURE:
<223> OTHER INFORMATION: Synthetic

<400> SEQUENCE: 134

Gln Ser Leu Leu His Ser Asn Gly Tyr Asn Tyr
1               5                   10

<210> SEQ ID NO 135
<211> LENGTH: 4
<212> TYPE: PRT
<213> ORGANISM: Artificial
<220> FEATURE:
<223> OTHER INFORMATION: Synthetic

<400> SEQUENCE: 135

Leu Gly Ser Ser
1

<210> SEQ ID NO 136
<211> LENGTH: 9
<212> TYPE: PRT
<213> ORGANISM: Artificial
<220> FEATURE:
<223> OTHER INFORMATION: Synthetic

<400> SEQUENCE: 136

Met Gln Gly Leu Gln Thr Pro Leu Thr
1               5
```

```
<210> SEQ ID NO 137
<211> LENGTH: 121
<212> TYPE: PRT
<213> ORGANISM: Artificial
<220> FEATURE:
<223> OTHER INFORMATION: Synthetic

<400> SEQUENCE: 137

Gln Val Gln Leu Val Gln Ser Gly Ala Glu Val Lys Lys Pro Gly Ala
1               5                   10                  15

Ser Val Lys Val Ser Cys Arg Thr Ser Gly Tyr Thr Phe Ser Ser Tyr
            20                  25                  30

Asn Ile His Trp Val Arg Gln Ala Pro Gly Gln Gly Leu Glu Trp Met
        35                  40                  45

Gly Val Ile Asn Pro Tyr Gly Arg Ser Thr Thr Leu Tyr Ala Arg Arg
    50                  55                  60

Phe Arg Asp Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Phe
                85                  90                  95

Cys Gly Arg Leu Tyr Ser Gly Ala Pro Tyr Gly Leu Asp Val Trp Gly
            100                 105                 110

Gln Gly Ser Thr Val Thr Val Ser Ser
        115                 120

<210> SEQ ID NO 138
<211> LENGTH: 10
<212> TYPE: PRT
<213> ORGANISM: Artificial
<220> FEATURE:
<223> OTHER INFORMATION: Synthetic

<400> SEQUENCE: 138

Gly Tyr Thr Phe Ser Ser Tyr Asn Ile His
1               5                   10

<210> SEQ ID NO 139
<211> LENGTH: 7
<212> TYPE: PRT
<213> ORGANISM: Artificial
<220> FEATURE:
<223> OTHER INFORMATION: Synthetic

<400> SEQUENCE: 139

Pro Tyr Gly Arg Ser Thr Thr
1               5

<210> SEQ ID NO 140
<211> LENGTH: 13
<212> TYPE: PRT
<213> ORGANISM: Artificial
<220> FEATURE:
<223> OTHER INFORMATION: Synthetic

<400> SEQUENCE: 140

Gly Arg Leu Tyr Ser Gly Ala Pro Tyr Gly Leu Asp Val
1               5                   10

<210> SEQ ID NO 141
<211> LENGTH: 113
<212> TYPE: PRT
<213> ORGANISM: Artificial
<220> FEATURE:
```

<223> OTHER INFORMATION: Synthetic

<400> SEQUENCE: 141

Asp Ile Val Leu Thr Gln Ser Pro Asp Ser Leu Ala Ala Ser Leu Gly
1               5                   10                  15

Glu Arg Ala Thr Ile Ser Cys Lys Ser Ser His Ser Val Leu Tyr Ser
            20                  25                  30

Ser Asn Asn Lys Asp Phe Phe Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Val Arg Phe Asn Gly Gly Ser Gly Thr His Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Ser Pro Ile Thr Phe Gly Gln Gly Thr Arg Leu Glu Ile
                100                 105                 110

Lys

<210> SEQ ID NO 142
<211> LENGTH: 12
<212> TYPE: PRT
<213> ORGANISM: Artificial
<220> FEATURE:
<223> OTHER INFORMATION: Synthetic

<400> SEQUENCE: 142

His Ser Val Leu Tyr Ser Ser Asn Asn Lys Asp Phe
1               5                   10

<210> SEQ ID NO 143
<211> LENGTH: 4
<212> TYPE: PRT
<213> ORGANISM: Artificial
<220> FEATURE:
<223> OTHER INFORMATION: Synthetic

<400> SEQUENCE: 143

Trp Ala Ser Thr
1

<210> SEQ ID NO 144
<211> LENGTH: 9
<212> TYPE: PRT
<213> ORGANISM: Artificial
<220> FEATURE:
<223> OTHER INFORMATION: Synthetic

<400> SEQUENCE: 144

Gln Gln Tyr Phe Ser Ser Pro Ile Thr
1               5

<210> SEQ ID NO 145
<211> LENGTH: 124
<212> TYPE: PRT
<213> ORGANISM: Artificial
<220> FEATURE:
<223> OTHER INFORMATION: Synthetic

<400> SEQUENCE: 145

Gln Val Gln Leu Val Gln Ser Gly Ala Glu Val Lys Lys Pro Gly Ser
1               5                   10                  15

-continued

Ser Val Lys Val Ala Cys Lys Val Ser Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ser Phe Gly Val Gly His Tyr Ser Gln Lys Phe
    50                  55                  60

Arg Asp Arg Val Thr Leu Thr Ala Asp Lys Ser Thr Thr Thr Ala Phe
65                  70                  75                  80

Leu Glu Leu Ser Ser Val Arg Ser Glu Asp Thr Ala Leu Tyr Tyr Cys
                85                  90                  95

Ala Ile Leu Gly Thr Phe Asn Trp Lys Ser Gly Gly Asn Tyr Phe Gly
            100                 105                 110

Pro Trp Gly Gln Gly Thr Leu Val Thr Val Ser Ser
        115                 120

<210> SEQ ID NO 146
<211> LENGTH: 8
<212> TYPE: PRT
<213> ORGANISM: Artificial
<220> FEATURE:
<223> OTHER INFORMATION: Synthetic

<400> SEQUENCE: 146

Gly Gly Thr Phe Ser Ser Tyr Thr
1               5

<210> SEQ ID NO 147
<211> LENGTH: 8
<212> TYPE: PRT
<213> ORGANISM: Artificial
<220> FEATURE:
<223> OTHER INFORMATION: Synthetic

<400> SEQUENCE: 147

Ile Ile Pro Ser Phe Gly Val Gly
1               5

<210> SEQ ID NO 148
<211> LENGTH: 17
<212> TYPE: PRT
<213> ORGANISM: Artificial
<220> FEATURE:
<223> OTHER INFORMATION: Synthetic

<400> SEQUENCE: 148

Ala Ile Leu Gly Thr Phe Asn Trp Lys Ser Gly Gly Asn Tyr Phe Gly
1               5                   10                  15

Pro

<210> SEQ ID NO 149
<211> LENGTH: 107
<212> TYPE: PRT
<213> ORGANISM: Artificial
<220> FEATURE:
<223> OTHER INFORMATION: Synthetic

<400> SEQUENCE: 149

Glu Ile Val Leu Thr Gln Ser Pro Asn Thr Leu Ser Leu Ser Pro Gly
1               5                   10                  15

Glu Arg Ala Thr Leu Ser Cys Arg Ala Ser Gln Ser Leu Arg Thr Asn
            20                  25                  30

Gln Leu Ala Trp Tyr Gln Gln Lys Pro Gly Gln Ala Pro Arg Leu Leu

```
                35                  40                  45
Ile His Thr Ser Thr Arg Ala Thr Gly Ile Pro Asp Arg Phe Ser Gly
    50                  55                  60
Ser Gly Ser Gly Thr Asp Phe Thr Leu Thr Ile Ser Gly Leu Glu Ala
65                  70                  75                  80
Glu Asp Phe Ala Val Tyr Tyr Cys Gln Ala Ser Asp Thr Ser Ser Leu
                85                  90                  95
Thr Phe Gly Gly Gly Thr Lys Leu Glu Ile Arg
            100                 105
```

<210> SEQ ID NO 150
<211> LENGTH: 6
<212> TYPE: PRT
<213> ORGANISM: Artificial
<220> FEATURE:
<223> OTHER INFORMATION: Synthetic

<400> SEQUENCE: 150

```
Gln Ser Leu Arg Thr Asn
1               5
```

<210> SEQ ID NO 151
<211> LENGTH: 4
<212> TYPE: PRT
<213> ORGANISM: Artificial
<220> FEATURE:
<223> OTHER INFORMATION: Synthetic

<400> SEQUENCE: 151

```
His Thr Ser Thr
1
```

<210> SEQ ID NO 152
<211> LENGTH: 9
<212> TYPE: PRT
<213> ORGANISM: Artificial
<220> FEATURE:
<223> OTHER INFORMATION: Synthetic

<400> SEQUENCE: 152

```
Gln Ala Ser Asp Thr Ser Ser Leu Thr
1               5
```

<210> SEQ ID NO 153
<211> LENGTH: 125
<212> TYPE: PRT
<213> ORGANISM: Artificial
<220> FEATURE:
<223> OTHER INFORMATION: Synthetic

<400> SEQUENCE: 153

```
Gln Val Gln Leu Gln Glu Ser Gly Pro Gly Leu Val Lys Pro Ser Glu
1               5                   10                  15
Ser Leu Ser Leu Thr Cys Thr Ile Ser Gly Gly Ser Ile Arg Asp Tyr
            20                  25                  30
Tyr Trp Ser Trp Ile Arg Gln Ala Pro Gly Lys Gly Leu Glu Trp Ile
        35                  40                  45
Gly Tyr Lys Tyr His Ala Ala Arg Gly Asn Ser Asn Pro Ser Leu Glu
    50                  55                  60
Ser Arg Val Thr Met Ser Ile Asp Thr Ser Arg Ser Glu Phe Ser Leu
65                  70                  75                  80
Arg Leu Thr Ser Val Thr Ala Ala Asp Thr Ala Val Tyr Tyr Cys Ala
```

```
                85                  90                  95
Arg Val Gln Tyr Gly Pro Gly Gly Tyr Tyr Ser Gly Asn Trp Leu
            100                 105                 110

Asp Leu Trp Gly Gln Gly Thr Leu Val Thr Val Ser Ser
        115                 120                 125
```

<210> SEQ ID NO 154
<211> LENGTH: 8
<212> TYPE: PRT
<213> ORGANISM: Artificial
<220> FEATURE:
<223> OTHER INFORMATION: Synthetic

<400> SEQUENCE: 154

```
Gly Gly Ser Ile Arg Asp Tyr Tyr
1               5
```

<210> SEQ ID NO 155
<211> LENGTH: 7
<212> TYPE: PRT
<213> ORGANISM: Artificial
<220> FEATURE:
<223> OTHER INFORMATION: Synthetic

<400> SEQUENCE: 155

```
Lys Tyr His Ala Ala Arg Gly
1               5
```

<210> SEQ ID NO 156
<211> LENGTH: 19
<212> TYPE: PRT
<213> ORGANISM: Artificial
<220> FEATURE:
<223> OTHER INFORMATION: Synthetic

<400> SEQUENCE: 156

```
Ala Arg Val Gln Tyr Gly Pro Gly Gly Tyr Tyr Ser Gly Asn Trp
1               5                   10                  15

Leu Asp Leu
```

<210> SEQ ID NO 157
<211> LENGTH: 106
<212> TYPE: PRT
<213> ORGANISM: Artificial
<220> FEATURE:
<223> OTHER INFORMATION: Synthetic

<400> SEQUENCE: 157

```
Glu Ile Val Met Thr Gln Ser Pro Ala Thr Leu Ser Leu Ser Pro Gly
1               5                   10                  15

Glu Arg Ala Ser Leu Ser Cys Arg Ala Ser Gln Ser Ile Ala Thr Asn
            20                  25                  30

Leu Ala Trp Tyr Gln Gln Lys Pro Gly Gln Pro Arg Val Leu Ile
        35                  40                  45

Tyr Gly Ala Ser Thr Arg Ala Thr Gly Ile Pro Thr Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys His Gln Tyr His Ser Trp Arg Thr
                85                  90                  95

Phe Gly Gln Gly Thr Lys Val Glu Met Lys
            100                 105
```

<210> SEQ ID NO 158
<211> LENGTH: 6
<212> TYPE: PRT
<213> ORGANISM: Artificial
<220> FEATURE:
<223> OTHER INFORMATION: Synthetic

<400> SEQUENCE: 158

Gln Ser Ile Ala Thr Asn
1               5

<210> SEQ ID NO 159
<211> LENGTH: 4
<212> TYPE: PRT
<213> ORGANISM: Artificial
<220> FEATURE:
<223> OTHER INFORMATION: Synthetic

<400> SEQUENCE: 159

Gly Ala Ser Thr
1

<210> SEQ ID NO 160
<211> LENGTH: 8
<212> TYPE: PRT
<213> ORGANISM: Artificial
<220> FEATURE:
<223> OTHER INFORMATION: Synthetic

<400> SEQUENCE: 160

His Gln Tyr His Ser Trp Arg Thr
1               5

<210> SEQ ID NO 161
<211> LENGTH: 122
<212> TYPE: PRT
<213> ORGANISM: Artificial
<220> FEATURE:
<223> OTHER INFORMATION: Synthetic

<400> SEQUENCE: 161

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ala Ser Ser
            20                  25                  30

Asn Asp Tyr Trp Gly Trp Ile Arg Gln Pro Pro Gly Lys Gly Pro Glu
        35                  40                  45

Trp Ile Gly Thr Ile Phe Tyr Arg Gly Thr Thr Asp Tyr Asn Pro Ser
    50                  55                  60

Leu Lys Ser Arg Leu Thr Met Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Pro Leu Trp Phe Ser Glu Leu Gly His Asp Tyr Trp
            100                 105                 110

Gly Gln Gly Thr Leu Val Thr Val Ser Ser
        115                 120

<210> SEQ ID NO 162
<211> LENGTH: 10
<212> TYPE: PRT
<213> ORGANISM: Artificial

```
<220> FEATURE:
<223> OTHER INFORMATION: Synthetic

<400> SEQUENCE: 162

Gly Gly Ser Val Ala Ser Ser Asn Asp Tyr
1               5                   10

<210> SEQ ID NO 163
<211> LENGTH: 7
<212> TYPE: PRT
<213> ORGANISM: Artificial
<220> FEATURE:
<223> OTHER INFORMATION: Synthetic

<400> SEQUENCE: 163

Ile Phe Tyr Arg Gly Thr Thr
1               5

<210> SEQ ID NO 164
<211> LENGTH: 14
<212> TYPE: PRT
<213> ORGANISM: Artificial
<220> FEATURE:
<223> OTHER INFORMATION: Synthetic

<400> SEQUENCE: 164

Ala Arg Leu Pro Leu Trp Phe Ser Glu Leu Gly His Asp Tyr
1               5                   10

<210> SEQ ID NO 165
<211> LENGTH: 111
<212> TYPE: PRT
<213> ORGANISM: Artificial
<220> FEATURE:
<223> OTHER INFORMATION: Synthetic

<400> SEQUENCE: 165

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Val Tyr
                20                  25                  30

Asn Ser Val Ser Trp Tyr Arg Gln His Pro Gly Lys Val Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Asp Asp Glu Gly Asp Tyr Tyr Cys Cys Ser Cys Ser Gly Thr
                85                  90                  95

Asn Ser Leu Cys Val Phe Gly Thr Gly Thr Lys Val Thr Val Leu
                100                 105                 110

<210> SEQ ID NO 166
<211> LENGTH: 9
<212> TYPE: PRT
<213> ORGANISM: Artificial
<220> FEATURE:
<223> OTHER INFORMATION: Synthetic

<400> SEQUENCE: 166

Ser Ser Asp Val Gly Val Tyr Asn Ser
1               5
```

```
<210> SEQ ID NO 167
<211> LENGTH: 4
<212> TYPE: PRT
<213> ORGANISM: Artificial
<220> FEATURE:
<223> OTHER INFORMATION: Synthetic

<400> SEQUENCE: 167

Glu Val Ser Lys
1

<210> SEQ ID NO 168
<211> LENGTH: 11
<212> TYPE: PRT
<213> ORGANISM: Artificial
<220> FEATURE:
<223> OTHER INFORMATION: Synthetic

<400> SEQUENCE: 168

Cys Ser Cys Ser Gly Thr Asn Ser Leu Cys Val
1               5                   10

<210> SEQ ID NO 169
<211> LENGTH: 124
<212> TYPE: PRT
<213> ORGANISM: Artificial
<220> FEATURE:
<223> OTHER INFORMATION: Synthetic

<400> SEQUENCE: 169

Gln Val Gln Leu His Glu Ser Gly Pro Gly Leu Val Gln Pro Ser Glu
1               5                   10                  15

Thr Leu Ser Leu Thr Cys Thr Val Ser Gly Asp Ser Ile Thr Asn Tyr
            20                  25                  30

Tyr Trp Ser Trp Ile Arg Gln Pro Pro Gly Lys Gly Leu Glu Trp Ile
        35                  40                  45

Gly Tyr Met Tyr Tyr Ser Ala Ser Ala His Tyr Asn Pro Ser Leu Gln
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Val Asp Tyr Ser Ser Ser Ser Tyr Tyr Ser Gly Asn Trp Phe Asp
            100                 105                 110

Pro Trp Gly Gln Gly Thr Leu Val Thr Val Ser Ser
        115                 120

<210> SEQ ID NO 170
<211> LENGTH: 8
<212> TYPE: PRT
<213> ORGANISM: Artificial
<220> FEATURE:
<223> OTHER INFORMATION: Synthetic

<400> SEQUENCE: 170

Gly Asp Ser Ile Thr Asn Tyr Tyr
1               5

<210> SEQ ID NO 171
<211> LENGTH: 7
<212> TYPE: PRT
<213> ORGANISM: Artificial
<220> FEATURE:
<223> OTHER INFORMATION: Synthetic
```

<400> SEQUENCE: 171

Met Tyr Tyr Ser Ala Ser Ala
1               5

<210> SEQ ID NO 172
<211> LENGTH: 18
<212> TYPE: PRT
<213> ORGANISM: Artificial
<220> FEATURE:
<223> OTHER INFORMATION: Synthetic

<400> SEQUENCE: 172

Ala Arg Val Asp Tyr Ser Ser Ser Tyr Tyr Ser Gly Asn Trp Phe
1               5                   10                  15

Asp Pro

<210> SEQ ID NO 173
<211> LENGTH: 112
<212> TYPE: PRT
<213> ORGANISM: Artificial
<220> FEATURE:
<223> OTHER INFORMATION: Synthetic

<400> SEQUENCE: 173

Gln Ser Val Leu Thr Gln Pro Pro Ser Val Ser Gly Ala Pro Gly Gln
1               5                   10                  15

Thr Val Thr Ile Ser Cys Thr Gly Ser Tyr Ser Asn Ile Gly Ala Gly
                20                  25                  30

Tyr Asp Val Gln Trp Tyr Gln His Leu Pro Gly Thr Ala Pro Lys Leu
            35                  40                  45

Leu Ile Tyr Asp Asn Val His Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Thr Glu Asp Glu Ala Asp Tyr Tyr Cys Gln Ser Tyr Asp Ser Arg
                85                  90                  95

Leu Arg Asp Gln Trp Val Phe Gly Gly Gly Thr Lys Leu Thr Val Leu
            100                 105                 110

<210> SEQ ID NO 174
<211> LENGTH: 9
<212> TYPE: PRT
<213> ORGANISM: Artificial
<220> FEATURE:
<223> OTHER INFORMATION: Synthetic

<400> SEQUENCE: 174

Tyr Ser Asn Ile Gly Ala Gly Tyr Asp
1               5

<210> SEQ ID NO 175
<211> LENGTH: 4
<212> TYPE: PRT
<213> ORGANISM: Artificial
<220> FEATURE:
<223> OTHER INFORMATION: Synthetic

<400> SEQUENCE: 175

Asp Asn Val His
1

<210> SEQ ID NO 176
<211> LENGTH: 12
<212> TYPE: PRT
<213> ORGANISM: Artificial
<220> FEATURE:
<223> OTHER INFORMATION: Synthetic

<400> SEQUENCE: 176

Gln Ser Tyr Asp Ser Arg Leu Arg Asp Gln Trp Val
1               5                   10

<210> SEQ ID NO 177
<211> LENGTH: 122
<212> TYPE: PRT
<213> ORGANISM: Artificial
<220> FEATURE:
<223> OTHER INFORMATION: Synthetic

<400> SEQUENCE: 177

Glu Val Gln Leu Val Glu Ser Gly Gly Asp Leu Val Gln Pro Gly Gly
1               5                   10                  15

Ser Leu Arg Leu Ser Cys Ala Ala Ser Gly Ile Thr Leu Ser Gly Val
            20                  25                  30

Trp Met Asn Trp Val Arg Gln Ala Pro Gly Lys Gly Leu Glu Trp Ile
        35                  40                  45

Gly Arg Ile Lys Ser Thr Ser Asp Gly Arg Ala Asp Phe Ala Ala
    50                  55                  60

Pro Ala Arg Gly Arg Phe Thr Met Ser Arg Asp Glu Ser Lys Asn Lys
65                  70                  75                  80

Leu Phe Leu Gln Met Asn Asn Leu Gly Ile Glu Asp Thr Gly Met Tyr
                85                  90                  95

Tyr Cys Phe Thr Arg Val Gln Arg Asp Gly Thr Lys Asp Asp Phe Trp
            100                 105                 110

Gly Arg Gly Thr Leu Val Thr Val Ser Ser
        115                 120

<210> SEQ ID NO 178
<211> LENGTH: 8
<212> TYPE: PRT
<213> ORGANISM: Artificial
<220> FEATURE:
<223> OTHER INFORMATION: Synthetic

<400> SEQUENCE: 178

Gly Ile Thr Leu Ser Gly Val Trp
1               5

<210> SEQ ID NO 179
<211> LENGTH: 10
<212> TYPE: PRT
<213> ORGANISM: Artificial
<220> FEATURE:
<223> OTHER INFORMATION: Synthetic

<400> SEQUENCE: 179

Ile Lys Ser Thr Ser Asp Gly Gly Arg Ala
1               5                   10

<210> SEQ ID NO 180
<211> LENGTH: 13
<212> TYPE: PRT
<213> ORGANISM: Artificial
<220> FEATURE:
<223> OTHER INFORMATION: Synthetic

<400> SEQUENCE: 180

Phe Thr Arg Val Gln Arg Asp Gly Thr Lys Asp Phe
1               5                   10

<210> SEQ ID NO 181
<211> LENGTH: 107
<212> TYPE: PRT
<213> ORGANISM: Artificial
<220> FEATURE:
<223> OTHER INFORMATION: Synthetic

<400> SEQUENCE: 181

Gln Ser Ala Leu Thr Gln Pro Ala Ser Val Ser Gly Ser Pro Gly Gln
1               5                   10                  15

Ser Ile Thr Leu Ser Cys Thr Val Gly Gly Asn Lys Phe Val Ser Trp
            20                  25                  30

Tyr Gln Gln His Pro Gly Lys Ala Pro Lys Leu Ile Ile Ser Asp Phe
        35                  40                  45

Thr Asp Arg Pro Ser Gly Val Ser Ser Arg Phe Ser Gly Ser Lys Ser
    50                  55                  60

Gly Asn Thr Ala Ser Leu Thr Ile Ser Gly Leu Gln Pro Asp Asp Glu
65                  70                  75                  80

Ala Thr Tyr Phe Cys Ser Ser Tyr Ala Ser Thr Ser Thr Ser Leu Trp
                85                  90                  95

Val Phe Gly Gly Gly Thr Lys Leu Thr Val Leu
            100                 105

<210> SEQ ID NO 182
<211> LENGTH: 8
<212> TYPE: PRT
<213> ORGANISM: Artificial
<220> FEATURE:
<223> OTHER INFORMATION: Synthetic

<400> SEQUENCE: 182

Cys Thr Val Gly Gly Asn Lys Phe
1               5

<210> SEQ ID NO 183
<211> LENGTH: 4
<212> TYPE: PRT
<213> ORGANISM: Artificial
<220> FEATURE:
<223> OTHER INFORMATION: Synthetic

<400> SEQUENCE: 183

Asp Phe Thr Asp
1

<210> SEQ ID NO 184
<211> LENGTH: 12
<212> TYPE: PRT
<213> ORGANISM: Artificial
<220> FEATURE:
<223> OTHER INFORMATION: Synthetic

<400> SEQUENCE: 184

Ser Ser Tyr Ala Ser Thr Ser Thr Ser Leu Trp Val
1               5                   10

<210> SEQ ID NO 185
<211> LENGTH: 125

<212> TYPE: PRT
<213> ORGANISM: Artificial
<220> FEATURE:
<223> OTHER INFORMATION: Synthetic

<400> SEQUENCE: 185

Gln Glu Gln Leu Gln Glu Ser Gly Pro Gly Leu Val Lys Pro Ser Gly
1               5                   10                  15

Thr Leu Ser Leu Thr Cys Thr Val Ser Gly Val Ser Val Ser Gly Ser
            20                  25                  30

Tyr Phe Trp Asn Trp Val Arg Gln Pro Pro Gly Lys Gly Leu Glu Trp
        35                  40                  45

Leu Gly Phe Ile His Ser Thr Gly Ser Thr Asn Thr Asn Pro Ser Leu
    50                  55                  60

Lys Ser Arg Val Thr Ile Ser Val Asp Thr Ser Lys Asn Gln Phe Ser
65                  70                  75                  80

Leu Arg Leu Thr Ser Val Ser Ala Ala Asp Thr Ala Val Tyr Tyr Cys
                85                  90                  95

Ala Arg Ala Ala Trp Leu Val Gly Gly Glu Tyr Tyr Asn Tyr Gly Met
            100                 105                 110

Asp Leu Trp Gly Gln Gly Thr Thr Val Thr Val Ser Ser
        115                 120                 125

<210> SEQ ID NO 186
<211> LENGTH: 9
<212> TYPE: PRT
<213> ORGANISM: Artificial
<220> FEATURE:
<223> OTHER INFORMATION: Synthetic

<400> SEQUENCE: 186

Gly Val Ser Val Ser Gly Ser Tyr Phe
1               5

<210> SEQ ID NO 187
<211> LENGTH: 7
<212> TYPE: PRT
<213> ORGANISM: Artificial
<220> FEATURE:
<223> OTHER INFORMATION: Synthetic

<400> SEQUENCE: 187

Ile His Ser Thr Gly Ser Thr
1               5

<210> SEQ ID NO 188
<211> LENGTH: 18
<212> TYPE: PRT
<213> ORGANISM: Artificial
<220> FEATURE:
<223> OTHER INFORMATION: Synthetic

<400> SEQUENCE: 188

Ala Arg Ala Ala Trp Leu Val Gly Gly Glu Tyr Tyr Asn Tyr Gly Met
1               5                   10                  15

Asp Leu

<210> SEQ ID NO 189
<211> LENGTH: 107
<212> TYPE: PRT
<213> ORGANISM: Artificial
<220> FEATURE:
<223> OTHER INFORMATION: Synthetic

<400> SEQUENCE: 189

Gly Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Tyr Thr Tyr
            20                  25                  30

Leu Ala Trp Tyr Gln Gln Lys Pro Gly Lys Ala Pro Lys Leu Leu Val
        35                  40                  45

Tyr Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gln Gly Thr Lys Leu Glu Ile Lys
            100                 105

<210> SEQ ID NO 190
<211> LENGTH: 6
<212> TYPE: PRT
<213> ORGANISM: Artificial
<220> FEATURE:
<223> OTHER INFORMATION: Synthetic

<400> SEQUENCE: 190

Gln Gly Ile Tyr Thr Tyr
1               5

<210> SEQ ID NO 191
<211> LENGTH: 4
<212> TYPE: PRT
<213> ORGANISM: Artificial
<220> FEATURE:
<223> OTHER INFORMATION: Synthetic

<400> SEQUENCE: 191

Val Ala Ser Tyr
1

<210> SEQ ID NO 192
<211> LENGTH: 9
<212> TYPE: PRT
<213> ORGANISM: Artificial
<220> FEATURE:
<223> OTHER INFORMATION: Synthetic

<400> SEQUENCE: 192

Gln Gln Leu Asn Ser Tyr Pro Leu Thr
1               5

<210> SEQ ID NO 193
<211> LENGTH: 127
<212> TYPE: PRT
<213> ORGANISM: Artificial
<220> FEATURE:
<223> OTHER INFORMATION: Synthetic

<400> SEQUENCE: 193

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Trp Tyr Asp Gly Thr Ile Gln Tyr Tyr Gly Asp Ser Val
 50                  55                  60

Lys Gly Arg Phe Ile Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Thr Leu Tyr Arg Asn Gly Asp Tyr Gly Ser Gly Ser Arg Thr
            100                 105                 110

Pro Asp Asp Tyr Trp Gly Gln Gly Thr Leu Val Thr Val Ser Ser
            115                 120                 125

<210> SEQ ID NO 194
<211> LENGTH: 8
<212> TYPE: PRT
<213> ORGANISM: Artificial
<220> FEATURE:
<223> OTHER INFORMATION: Synthetic

<400> SEQUENCE: 194

Gly Phe Thr Phe Ser Ser Tyr Gly
1               5

<210> SEQ ID NO 195
<211> LENGTH: 8
<212> TYPE: PRT
<213> ORGANISM: Artificial
<220> FEATURE:
<223> OTHER INFORMATION: Synthetic

<400> SEQUENCE: 195

Ile Trp Tyr Asp Gly Thr Ile Gln
1               5

<210> SEQ ID NO 196
<211> LENGTH: 20
<212> TYPE: PRT
<213> ORGANISM: Artificial
<220> FEATURE:
<223> OTHER INFORMATION: Synthetic

<400> SEQUENCE: 196

Ala Ser Thr Leu Tyr Arg Asn Gly Asp Tyr Gly Ser Gly Ser Arg Thr
1               5                   10                  15

Pro Asp Asp Tyr
            20

<210> SEQ ID NO 197
<211> LENGTH: 360
<212> TYPE: DNA
<213> ORGANISM: Artificial
<220> FEATURE:
<223> OTHER INFORMATION: Synthetic

<400> SEQUENCE: 197
gaggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag ggcttgagtg gatgggaata atcaacccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc taggcatgat     300

```
agtagtggtt atgatgcttt tgatatctgg ggccaaggga caatggtcac cgtctcttca    360
```

<210> SEQ ID NO 198
<211> LENGTH: 324
<212> TYPE: DNA
<213> ORGANISM: Artificial
<220> FEATURE:
<223> OTHER INFORMATION: Synthetic

<400> SEQUENCE: 198

```
tcctatgagc tgacacagcc accctcggtg tcagtgtccc caggacagac ggccaggatc     60
acctgctctg gagatgcatt gccaaagcaa tatgcttatt ggtaccagca gaagccaggc    120
caggcccctg tgccggtgat atataaagac agtgagaggc cctcagggat ccctgagcga    180
ttctctggct ccagctcagg gacaacagtg acgttgacca tcagtggagt ccaggcagaa    240
gacgaggctg actattactg tcaatcatca gacagcagtg gtacttatgt ggtattcggc    300
ggagggacca agctgaccgt ccta                                           324
```

<210> SEQ ID NO 199
<211> LENGTH: 363
<212> TYPE: DNA
<213> ORGANISM: Artificial
<220> FEATURE:
<223> OTHER INFORMATION: Synthetic

<400> SEQUENCE: 199

```
caggtgcaac tggtgcagtc aggggctgag gtgaagaagc ctggggcctc agtgaaggtt     60
tcctgcagga catctggata cacattctcc agctacaata tacattgggt gcgacaggcc    120
cctggacaag tcttgagtg gatgggagtt attaatcctt atggccgtag taccacactt    180
tacgcacgga ggttccggga cagagtcacc atgaccaggg acacgtccac gagcacagtt    240
tacatggaac tgagcagcct gagatccgag gacacggccg tatacttctg tggaaggctt    300
tacagtggtg caccctatgg tttggacgtc tggggccaag ggagcacggt caccgtctct    360
tca                                                                  363
```

<210> SEQ ID NO 200
<211> LENGTH: 336
<212> TYPE: DNA
<213> ORGANISM: Artificial
<220> FEATURE:
<223> OTHER INFORMATION: Synthetic

<400> SEQUENCE: 200

```
gatattgtga tgactcagtc tccactctcc ctgcccgtca cccctggaga gccggcctcc     60
atctcctgca ggtctagtca gagcctcctg catagtaatg gatacaacta tgtggattgg    120
tacctgcaga agccagggca gtctccacag ctcctgatct atttgggttc tagtcgggcc    180
tccggggtcc ctgacaggtt cagtggcagt ggatcaggca cagattttac actgaaaatc    240
agcagagtgg agactgagga tgttggcatt tattactgca tgcaaggtct acaaactccc    300
ctcactttcg gcggagggac caaggtggag atcaaa                              336
```

<210> SEQ ID NO 201
<211> LENGTH: 372
<212> TYPE: DNA
<213> ORGANISM: Artificial
<220> FEATURE:
<223> OTHER INFORMATION: Synthetic

<400> SEQUENCE: 201

```
caggtgcagc tggtgcagtc tggggctgaa gtgaagaagc ctgggtcctc ggtgaaggtc      60
gcctgcaagg tttctggagg caccttcagc agctatacta ttagttgggt gcgacaggcc     120
cctggacaag gcttgagtg gatgggaggg atcatcccctt cctttggtgt gggacactac     180
tcacagaagt tccgggacag agtcacgcta accgcggaca atccacgac cacagccttc      240
ttggaactga gcagcgtgag atctgaagac acggccctat attactgtgc gatactgggg     300
acttttaact ggaagtccgg gggcaactac ttcggcccct ggggccaggg gaccctggtc     360
accgtctctt ca                                                          372
```

<210> SEQ ID NO 202
<211> LENGTH: 339
<212> TYPE: DNA
<213> ORGANISM: Artificial
<220> FEATURE:
<223> OTHER INFORMATION: Synthetic

<400> SEQUENCE: 202

```
gacatcgtgc tgacccagtc tccagactcc ctggctgcgt ctctgggcga gagggccacc      60
atcagctgca agtccagcca cagtgtttta tacagctcca acaataagga cttctttgcc     120
tggtaccagc agaaaccagg acagcctccc aaactgctca tttcctgggc atctacccgg     180
gaatccgggg tccctgtccg attcaatggc ggcgggtctg ggacacattt cactctcacc     240
atcagcagcc tgcaggctga agatgtggca gtttactact gtcagcaata ttttagttct     300
ccgatcaccct tcggccaagg gacacgactg gagattaaa                            339
```

<210> SEQ ID NO 203
<211> LENGTH: 375
<212> TYPE: DNA
<213> ORGANISM: Artificial
<220> FEATURE:
<223> OTHER INFORMATION: Synthetic

<400> SEQUENCE: 203

```
caggtgcagc tgcaggagtc gggcccagga ctggtgaagc cttcggagag cctgtccctc      60
acatgcacta tctctggcgg ctccataagg gactattact ggagctggat tcggcaggcc     120
ccagggaagg gactggagtg gatcggatat aagtatcacg ctgcgcgcgg caactccaat     180
cccctccctcg agagtcgagt caccatgtcc atcgacacgt ccaggagcga gttctccctg     240
aggctgactt ctgtgaccgc tgcggacacg gccgtctatt attgtgcgag agttcaatac     300
ggtcctgggg gcggttacta ttcggggaac tggttggacc tctggggcca gggaaccctg     360
gtcaccgtct cttca                                                       375
```

<210> SEQ ID NO 204
<211> LENGTH: 321
<212> TYPE: DNA
<213> ORGANISM: Artificial
<220> FEATURE:
<223> OTHER INFORMATION: Synthetic

<400> SEQUENCE: 204

```
gaaattgtgt tgacacagtc tccaaacacc ctgtctttgt ctccagggga aagagccacc      60
ctctcctgca gggccagtca gagtcttcgt accaaccagt tagcctggta ccagcaaaaa     120
cctggccagg ctcccaggct cctcatccat acatccacca gggccactgg catcccagac     180
aggttcagtg gcagtgggtc tgggacagac ttcactctca ccatcagcgg actggaggct     240
```

```
gaagactttg cagtgtatta ctgtcaggcg tctgatacct catcgctcac tttcggcgga    300
gggaccaagt tagagatcag a                                              321

<210> SEQ ID NO 205
<211> LENGTH: 366
<212> TYPE: DNA
<213> ORGANISM: Artificial
<220> FEATURE:
<223> OTHER INFORMATION: Synthetic

<400> SEQUENCE: 205
cagctgcagc tgcaggagtc gggcccagga ctggtgaagc cttcggagac cctgtccctc    60
acctgcactg tctctggtgg ctccgtcgcc agtagtaatg actactgggg ctggatccgc    120
cagcccccag ggaaggggcc ggagtggatt gggactatct tttatagagg gaccaccgac    180
tacaacccgt ccctcaagag tcgactcact atgtccgtgg acacgtccag gaaccagttc    240
tccctgaagc tgagctctgt gaccgccgca gacacggctg tctattactg tgcgagactg    300
cccctatggt tcagtgagtt aggtcatgac tactggggcc agggaaccct ggtcaccgtc    360
tcctca                                                               366

<210> SEQ ID NO 206
<211> LENGTH: 407
<212> TYPE: DNA
<213> ORGANISM: Artificial
<220> FEATURE:
<223> OTHER INFORMATION: Synthetic

<400> SEQUENCE: 206
gaaatagtga tgacgcagtc tccagccacc ctgtctctgt ctccaggaga aagagcctcc    60
ctgtcctgca gggccagtca gagtattgcc accaacttag cctggtacca gcaaaaacct    120
ggccagcctc ccagggtcct catctatggt gcatccacaa gggcaactgg tatcccaacc    180
aggttcagtg gcagtggatc tgggacagag ttcactctca ccatcagcag cctgcagtct    240
gaagattttg caatttatta ctgtcaccag tatcatagct ggcggacgtt cggccaaggg    300
accaaggtag aaatgaaagt gcgagagtgg actacagttc gagtagttat tattcgggaa    360
actggttcga cccctggggc agggaaccc ttgtcaccgt ctcctca                   407

<210> SEQ ID NO 207
<211> LENGTH: 372
<212> TYPE: DNA
<213> ORGANISM: Artificial
<220> FEATURE:
<223> OTHER INFORMATION: Synthetic

<400> SEQUENCE: 207
caggtgcagc tgcatgagtc gggcccaggg ctggtgcagc cttcggagac cctgtccctc    60
acctgcactg tctctggtga ctccatcact aattactact ggagctggat ccggcagccc    120
ccagggaagg gactggagtg gattggatat atgtattaca gtgcgagcgc ccactacaat    180 ccctcccctcc agagtcgagt caccatttca gtggacacgt ccaagaacca gttctccctg    240
aaactgagct ctgtgaccgc tgcggacacg gccgtgtatt tctgtgcgag agtggactac    300
agttcgagta gttattattc gggaaactgg ttcgacccct ggggccaggg aacccttgtc    360
accgtctcct ca                                                        372

<210> SEQ ID NO 208
```

```
<211> LENGTH: 333
<212> TYPE: DNA
<213> ORGANISM: Artificial
<220> FEATURE:
<223> OTHER INFORMATION: Synthetic

<400> SEQUENCE: 208
cagtctgccc tgactcagcc tccctccgcg tccgggtctc ctggacagtc agtcaccatc      60
tcctgcactg gaaccagcag tgacgttggt gtttataatt ctgtctcctg gtaccgacag     120
cacccaggca aagtccccaa actcatgatt tatgaggtca gtaagcggcc ctcagggctc     180
cctgatcgct tctctggctc caagtccggc aacacggcct ccctgaccgt ctctgggctc     240
caggctgacg atgagggtga ttattactgc tgctcatgtt caggcaccaa cagcctctgt     300
gtcttcggaa ctgggaccaa ggtcaccgtc ctg                                  333

<210> SEQ ID NO 209
<211> LENGTH: 366
<212> TYPE: DNA
<213> ORGANISM: Artificial
<220> FEATURE:
<223> OTHER INFORMATION: Synthetic

<400> SEQUENCE: 209
gaggtgcagc tggtggagtc tgggggagac ttagtacagc ctgggggctc cctcagactc      60
tcctgtgcag cctctggaat caccttgagt ggagtttgga tgaactgggt ccgccaggct     120
ccagggaagg ggctggagtg gattggccgt attaaaagca aagtgacgg tgggagagca     180 gacttcgccg cacccgcgag aggcagattc accatgtcaa gagatgagtc aaagaataag     240
ctgtttctgc aaatgaacaa cctgggaatc gaagacacag gcatgtatta ttgtttcacg     300
agagtccaaa gagacggaac taaagatgac ttctggggcc ggggaaccct ggtcaccgtc     360
tcttca                                                                366

<210> SEQ ID NO 210
<211> LENGTH: 336
<212> TYPE: DNA
<213> ORGANISM: Artificial
<220> FEATURE:
<223> OTHER INFORMATION: Synthetic

<400> SEQUENCE: 210
cagtctgtgc tgacgcagcc gccctcagtg tctggggccc cagggcagac ggtcaccatc      60
tcctgcactg ggagctactc caacatcggg gcaggttatg atgtacagtg gtaccagcac     120
cttcctggaa cagccccaa actcctcatt tatgataatg tccatcggcc ctcagggttc     180
cctgaccgat tctctggctc caagtctggc acctcagcct ccctggccat cactgggctc     240
cagactgaag atgaggctga ttattattgc cagtcctatg acagcagact gagggatcaa     300
tgggtgttcg gcggagggac caagctgacc gtccta                               336

<210> SEQ ID NO 211
<211> LENGTH: 375
<212> TYPE: DNA
<213> ORGANISM: Artificial
<220> FEATURE:
<223> OTHER INFORMATION: Synthetic

<400> SEQUENCE: 211
caggagcagc tgcaagagtc gggcccagga ctggtgaagc cttcgggac cctgtccctc      60 acctgcactg tctccggcgt ctccgtcagt gggagttact tctggaattg gtccgccag     120
```

```
cccccaggga agggactgga gtggcttgga tttattcata gcactgggag caccaacacc    180
aacccctccc tcaagagtcg agtcaccatt tcagtagaca cgtccaagaa ccagttctcc    240
ctgaggctga cttctgtgag cgctgcggac acggccgttt attactgtgc gagagccgct    300
tggttagtag gggggagta ctacaactac ggtatggacc tttggggcca agggaccacg    360
gttaccgtct cctca                                                     375
```

```
<210> SEQ ID NO 212
<211> LENGTH: 321
<212> TYPE: DNA
<213> ORGANISM: Artificial
<220> FEATURE:
<223> OTHER INFORMATION: Synthetic

<400> SEQUENCE: 212
cagtctgccc tgactcagcc cgcctccgtt tctgggtctc ctggacagtc gatcaccctc     60
tcctgcactg taggcggtaa taagtttgtc tcttggtatc aacaacccc aggcaaagcc    120 cccaaactca ttatttctga tttcactgat cggccctcag gggtctctag tcgcttctct    180
ggctccaagt ctggcaacac ggcctccctg accatctctg gctccagcc tgacgacgag    240 gctacttatt tctgcagttc ttacgcaagc accagcactt ctctttgggt cttcggcggg    300
gggaccaagc tgaccgtcct a                                              321
```

```
<210> SEQ ID NO 213
<211> LENGTH: 381
<212> TYPE: DNA
<213> ORGANISM: Artificial
<220> FEATURE:
<223> OTHER INFORMATION: Synthetic

<400> SEQUENCE: 213
caggtgcagc tggtggaatc tgggggaggc gtggtccagc ctgggaggtc cctgagactc     60
tcctgtgtag cgtctggatt caccttcagt agttatggca tgcactgggt ccgccaggct    120
ccaggcaagg gctggagtg gtggcattt atatggtatg atggaactat tcaatactat    180
ggagactccg tgaagggccg attcatcatc tccagagaca attccaggaa tacgctgtat    240
ctacaaatga acagcctgag agccgaggac acggctgtgt attactgtgc gagcactctt    300
taccgaaacg gtgactacgg gtcagggtcc cggaccccgg acgactactg ggccaggga    360 accctggtca ccgtctcttc a                                              381
```

```
<210> SEQ ID NO 214
<211> LENGTH: 321
<212> TYPE: DNA
<213> ORGANISM: Artificial
<220> FEATURE:
<223> OTHER INFORMATION: Synthetic

<400> SEQUENCE: 214
ggcatccagt tgacccagtc tccatccttc ctgtctgcat ctgtaggaga cagagtcacc     60
atcacttgcc gggccagtca gggcattac acttatttag cctggtatca gcaaaaacca    120
gggaaagccc ctaagctcct ggtctatgtt gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctctcac ttttggccag    300
gggaccaagc tggagatcaa a                                              321
```

```
<210> SEQ ID NO 215
<211> LENGTH: 6
<212> TYPE: PRT
<213> ORGANISM: Artificial
<220> FEATURE:
<223> OTHER INFORMATION: Synthetic construct

<400> SEQUENCE: 215

Gly Gly Gly Gly Gly Gly
1               5

<210> SEQ ID NO 216
<211> LENGTH: 5
<212> TYPE: PRT
<213> ORGANISM: Artificial
<220> FEATURE:
<223> OTHER INFORMATION: Synthetic construct

<400> SEQUENCE: 216

Gly Gly Gly Gly Thr
1               5

<210> SEQ ID NO 217
<211> LENGTH: 6
<212> TYPE: PRT
<213> ORGANISM: Artificial
<220> FEATURE:
<223> OTHER INFORMATION: Synthetic construct

<400> SEQUENCE: 217

Gly Gly Gly Pro Pro Pro
1               5

<210> SEQ ID NO 218
<211> LENGTH: 7
<212> TYPE: PRT
<213> ORGANISM: Artificial
<220> FEATURE:
<223> OTHER INFORMATION: Synthetic construct

<400> SEQUENCE: 218

Gly Gly Gly Ala Pro Pro Pro
1               5
```